United States Patent [19]

Lee

[11] Patent Number: 5,750,533

[45] Date of Patent: May 12, 1998

[54] 14-SUBSTITUTED MARCFORTINES AND DERIVATIVES USEFUL AS ANTIPARASITIC AGENTS

[75] Inventor: Byung H. Lee, Kalamazoo, Mich.

[73] Assignee: Pharmacia & Upjohn Company, Kalamazoo, Mich.

[21] Appl. No.: 557,033

[22] PCT Filed: Jun. 7, 1994

[86] PCT No.: PCT/US94/06037

§ 371 Date: Dec. 7, 1995

§ 102(e) Date: Dec. 7, 1995

[87] PCT Pub. No.: WO94/29319

PCT Pub. Date: Dec. 22, 1994

[51] Int. Cl.$^6$ ............... C07D 453/06; C07D 491/20; A61K 31/435

[52] U.S. Cl. ............... 514/278; 546/18; 544/230; 514/250

[58] Field of Search ............... 546/18; 544/230; 514/278, 250

[56] References Cited

U.S. PATENT DOCUMENTS

| | | | |
|---|---|---|---|
| 4,873,247 | 10/1989 | Goegelman et al. | 514/257 |
| 4,923,867 | 5/1990 | Blizzard et al. | 514/250 |
| 4,978,190 | 12/1990 | Blizzard et al. | 514/63 |
| 5,075,307 | 12/1991 | Matas et al. | 514/250 |
| 5,164,389 | 11/1992 | Chen | 514/250 |

*Primary Examiner*—Alan L. Rotman
*Attorney, Agent, or Firm*—William G. Jameson

[57] ABSTRACT

There are disclosed 14α-hydroxymarcfortine derivatives of the natural products marcfortine A, B, C, and D useful in the treatment and prevention of helminth and arthropod infections of animals and plants. The synthetic derivatives are of Formula (I).

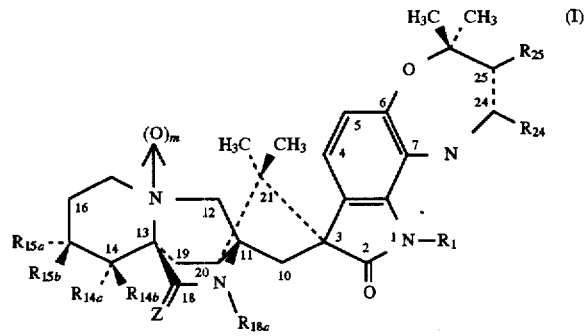

17 Claims, No Drawings

14-SUBSTITUTED MARCFORTINES AND DERIVATIVES USEFUL AS ANTIPARASITIC AGENTS

CROSS-REFERENCE

This application is a 371 of PCT/US94/06037 filed Jun. 7, 1994.

BACKGROUND OF THE INVENTION

The marcfortines are known compounds and are disclosed by Polonsky et al. in Journal of the Chemical Society Chemical Communications 1980 601–602 (Marcfortine A) and Tetrahedron Letters 1981 22 1977–1980 (Marcfortines B and C). The compounds are fungal metabolites of *Penicillium roqueforti*. The marcfortines are structurally related to the paraherquamides which are also known compounds. The paraherquamides are disclosed by Yamazaki et al. in Tetrahedron Letters 1981 22 135–136, and by Blanchflower et al., Journal of Antibiotics, 1991, 44, 492–497. U.S. Pat. Nos. 4,866,060 and 4,923,867 disclose the use of the marcfortines A, B, and C, and certain derivatives thereof as useful for the treatment and prevention of parasitic diseases in animals.

WO 92/22555 (published 23 Dec. 1992) generically describes a marcfortine or paraherquamide derivative (i.e. partial formula (III) substituted at position 14 with methyl or methyl and hydroxy, however no description of how to prepare such 14-methyl-14-hydroxymarcfortine compounds is provided.

Paraherquamide has the following structure:

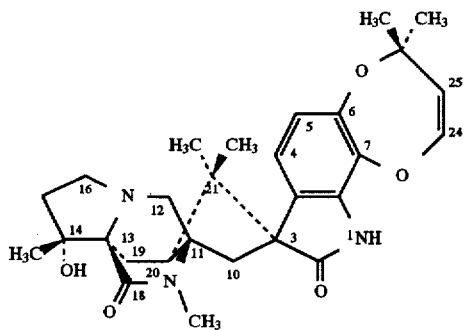

Marcfortine A has the following structure:

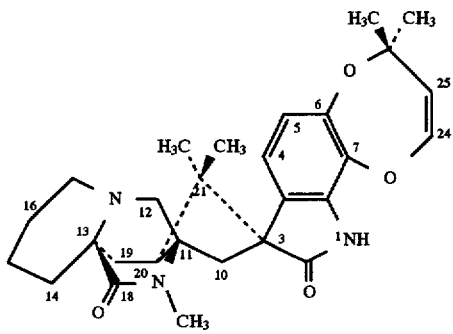

Marcfortine B has the following structure:

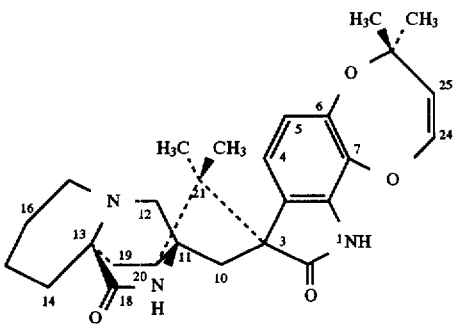

Marcfortine C has the following structure:

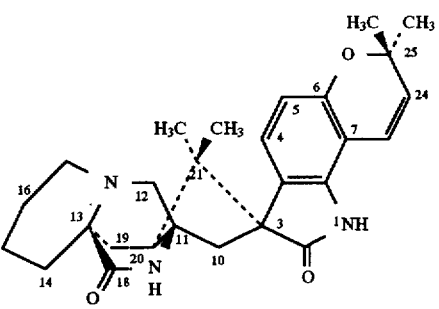

Marcfortine D has the following structure:

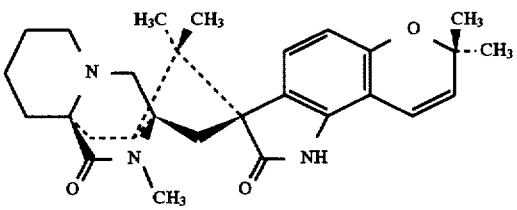

WO 91/09961 (published 11 Jul. 1991) discloses various derivatives of marcfortine and paraherquamide, and 12a-N-oxides thereof, as well as the production the production of VM 29919 (paraherquamide) and VM 55596 (the 12a-N-oxide of paraherquamide) inter alia from Penicillium Sp. IMI 332995.

U.S. Pat. No. 4,873,247 discloses derivatives of paraherquamide and a strain of *Penicillium charlessi* MF 5123 (ATCC 20841) for the production of paraherquamide. U.S. Pat. No. 4,978,656 (as well as EP 390532-A, EP-301742-A) discloses various synthetic derivatives of paraherquamide as well as the production of paraherquamide from *Penicillium charlessi* MF 5123 (ATCC 20841).

SmithKline Beecham in International Publication No. WO 92/22555 (published 23 Dec. 1992) generically discloses 14α-hydroxy-marcfortine compounds and a process which uses the 14-hydroxy-14-methylmarcfortine compounds for the production of antiparasitic drugs. However, no enabling description of any means of preparation of 14α-hydroxy-marcfortine or 14α-hydroxy-14β-methyl-marcfortine compounds is provided.

SUMMARY OF THE INVENTION

This invention is concerned with the synthesis of 14-substituted marcfortines A, B, C, and D and derivatives thereof and the use of these compounds as antiparasitic agents. Thus it is an object of this invention to describe these marcfortine derivatives. A further object of this invention is to describe processes for the preparation of these compounds. A still further object is to describe the use of the instant compounds as antiparasitic agents in the treatment and prevention of parasitic diseases. A still further object is to describe compositions for the treatment of parasitic diseases which contain the novel compounds of this invention as the active ingredient thereof. Further objects will become apparent from a reading of the following description.

DESCRIPTION OF THE INVENTON

The compounds of the instant invention are represented by Formula I:

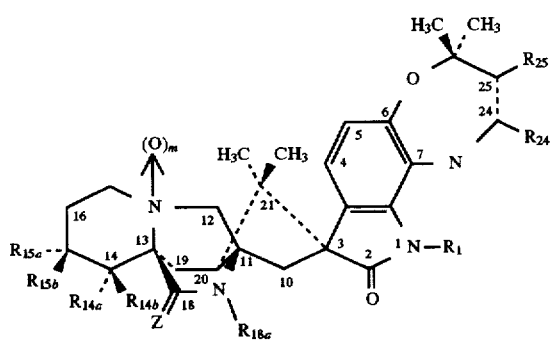

wherein:
m is 0 or 1;
Z is O or S;
Y is an oxygen atom (—O—) or a bond;
$R_1$ is hydrogen, $C_1$-$C_7$ alkyl, cyclo $C_3$-$C_8$alkyl, benzyl, $C_2$-$C_7$ alkanoyl (—C(O)$C_2$-$C_7$alkyl) {optionally substituted with carboxy (—COOH), $C_1$-$C_7$ alkanoyl, carbo$C_1$-$C_7$alkoxy (—C(O)O$C_1$-$C_7$alkyl), —NR$_4$R$_5$, aminocarbonyl (—C(O)NR$_4$R$_5$)}, $C_{10}$-$C_{24}$ alkanoyl (—C(O) $C_{10}$-$C_{24}$alkyl, cyclo $C_3$-$C_8$alkanoyl {optionally substituted with carboxy, $C_1$-$C_7$ alkanoyl, carbo$C_1$-$C_7$alkoxy, —NR$_4$R$_5$, aminocarbonyl}, alkanoyloxymethylene (—CH$_2$OC(O)—$C_2$-$C_7$alkyl), benzoyloxymethlene (—CH$_2$OCO(O)phenyl) {optionally substituted with 1 or 2 groups selected from halogen, $C_1$-$C_4$ alkyl, halo$C_1$-$C_7$alkyl, nitro, cyano and $C_1$-$C_7$alkoxy}, $C_{10}$-$C_{24}$alkenoyl (—C(O) $C_9$-$C_{23}$alkenyl), benzenesulfonyl (—SO$_2$CH$_2$phenyl) {optionally substituted with 1 or 2 groups selected from halogen, $C_1$-$C_4$ alkyl, halo$C_1$-$C_7$alkyl, nitro, cyano and $C_1$-$C_7$alkoxy}, $C_1$-$C_4$alkylaminocarbonyl (—C(O)N ($C_1$-$C_4$alkyl)$_2$), $C_1$-$C_4$alkylaminothiocarbonyl (—C(S)N ($C_1$-$C_4$alkyl)$_2$), $C_1$-$C_7$ alkoxycarbonyl, phenoxycarbonyl {optionally substituted with 1 or 2 groups selected from halogen, $C_1$-$C_4$ alkyl, halo$C_1$-$C_7$alkyl, nitro, cyano and $C_1$-$C_7$alkoxy}, —C(O)NR'$_4$R'$_5$, —P(=X)(R$_2$)(R$_3$), —SR$_6$, —SO$_2$NR$_4$R5, benzoyl substituted at the 3 or 4 position with —CH$_2$NR$_4$R$_5$ or bicyclo$C_8$-$C_{12}$alkanoyl;

$R_4$ and $R_5$, being the same or different, are selected from hydrogen, $C_1$-$C_7$ alkyl, phenyl {optionally substituted with 1 or 2 groups selected from halogen, $C_1$-$C_4$ alkyl, halo$C_1$-$C_7$alkyl, nitro, cyano and $C_1$-$C_7$alkoxy} or when taken together with N, form a saturated or unsaturated heterocyclic amine ring;

R'$_4$ and R'$_5$, being the same or different, are selected from $C_1$-$C_7$ alkyl, cyclo($C_3$-$C_8$)alkyl, phenyl {optionally substituted with 1 or 2 groups selected from halogen, $C_1$-$C_4$ alkyl, halo$C_1$-$C_7$alkyl, nitro, cyano and $C_1$-$C_7$alkoxy} or when taken together with N, form a saturated heterocyclic amine ring optionally containing 1 or 2 additional heteroatoms selected from N, O or S;

X is O or S;

$R_2$ and $R_3$, being the same or different, are selected from $C_1$-$C_7$ alkyl, phenyl {optionally substituted with 1 or 2 groups selected from halogen, $C_{1-4}$ alkyl, halo$C_1$-$C_7$alkyl, nitro, cyano and $C_1$-$C_7$alkoxy}, $C_1$-$C_7$ alkoxy, thio($C_1$-$C_7$) alkoxy, phenoxy, thophenoxy, —NR$_7$R$_8$ {where $R_7$ and $R_8$, being the same or different, are selected from H, $C_1$-$C_7$ alkyl or taken together with N, form a saturated heterocyclic ring}, or taken together with P form a 4- to 7-membered heterocyclic ring;

$R_6$ is $C_1$-$C_7$, alkyl, halo$C_1$-$C_7$alkyl, carbo$C_1$-$C_7$alkoxy, —NR$_9$R$_{10}$ where $R_9$ and $R_{10}$, being the same or different, are $C_1$-$C_7$ alkyl or phenyl (optionally substituted with 1 or 2 groups selected from halo, lower alkyl, halo$C_1$-$C_7$alkyl, nitro, cyano, $C_1$-$C_7$ alkoxy);

$R_{24}$ is hydrogen, halogen or $C_1$-$C_7$ alkoxy;

$R_{25}$ is hydrogen or halogen;

$R_{18a}$ is hydrogen, $C_1$-$C_7$ alkyl, $C_2$-$C_8$ alkoxyalkyl, $C_2$-$C_8$ alkenyl, $C_2$-$C_8$ alkynyl or benzyl;

$R_{14a}$ is hydroxyl, hydrogen, $C_1$-$C_7$ alkyl, $C_2$-$C_8$ alkoxyalkyl, cyclo($C_3$-$C_8$)alkyl or benzyl (optionally substituted with 1 or 2 groups selected from halo, lower alkyl, halo$C_1$-$C_7$alkyl, nitro, cyano, $C_1$-$C_7$ alkoxy);

$R_{14b}$ is hydrogen, hydroxyl, $C_1$-$C_7$ alkoxy, cyclo($C_3$-$C_8$) alkyl or benzoxyl (optionally substituted with 1 or 2 groups selected from halo, lower alkyl, halo$C_1$-$C_7$alkyl, nitro, cyano, $C_1$-$C_7$ alkoxy);

$R_{15a}$ and $R_{15b}$ are both hydrogen, with the provisio that when one of $R_{14a}$ or $R_{14b}$ is hydroxyl and the other is hydrogen or methyl, $R_{15a}$ and $R_{15b}$ can be hydrogen or methyl;

the broken line between carbons 24 and 25 represents a single or double bond; and with the overall proviso that $R_{14a}$ and $R_{14b}$ are not both hydrogen.

The compounds of this invention include pharmaceutically acceptable salts thereof as well as 12a-N-oxides thereof.

Another aspect of this invention provides 14-substituted marcfortine A, and B compounds of Formula IA:

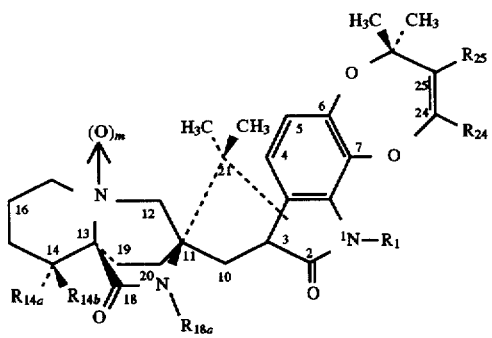

Another aspect of this invention provides 14-substituted thiomarcfortine A, and B compounds of Formula IB:

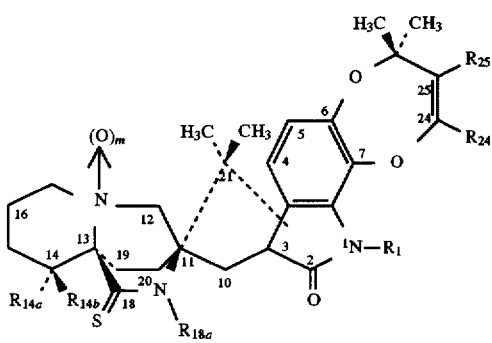

Another aspect of this invention provides an 14-substituted marcfortine C and D compounds of Formula II:

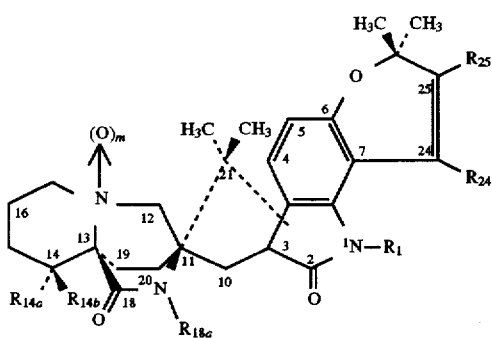

Another aspect of this invention provides an 14-substituted thiomarcfortine C and D compounds of Formula III:

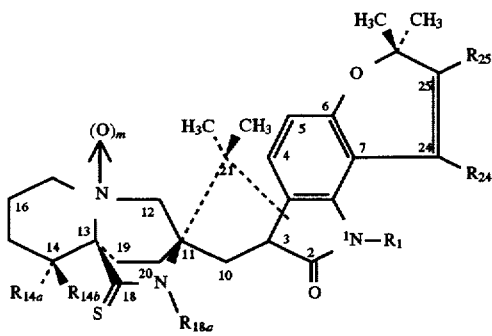

The carbon content of various hydrocarbon containing moieties is indicated by a prefix designating the minimum and maximum numer of carbon atoms in the moiety, i.e., the prefix $C_i$–$C_j$ indicates a carbon atoms content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the above, "$C_1$–$C_7$ alkyl" is intended to include those alkyl groups of from 1 to 7 carbon atoms in either a straight or branched chain. Examples of such lower alkyl groups are methyl, ethyl, propyl, isopropyl, butyl, sec-butyl, tert-butyl, pentyl, hexyl, heptyl and the like.

Cyclo($C_3$–$C_8$)alkyl is intended to include alkyl rings of 3 to 8 members. Examples of cyclo($C_3$–$C_8$)alkyl groups are cyclopropyl, cyclobutyl, cyclopentyl, cyclohexyl, cycloheptyl, bicyclo[2.2.1]heptyl, and the like.

$C_1$–$C_8$ alkoxy is intended to include those alkoxy groups of from 1 to 8 carbon atoms in either a straight or branched chain. Examples of such $C_1$–$C_8$ alkoxy groups are methoxy, ethoxy, propoxy, isopropoxy, butoxy, sec-butoxy, pentoxy, hexoxy, heptoxy, and the like.

$C_2$–$C_7$alkanoyl is intended to include those alkanoyl groups of from 2 to 7 carbon atoms in either a straight or branched chain. Examples of such $C_2$–$C_7$alkanoyl groups include acetyl, propionyl, isopropionyl, butyryl, pentanoyl, hexanoyl and the like.

$C_{10}$–$C_{24}$alkanoyl (—C(O)$C_9$–$C_{23}$alkyl) is intended to include those alkanoyl groups of from 10 to 24 carbon atoms in either a straight or branched chain. Examples of such $C_{10}$–$C_{24}$alkanoyl groups include decanoyl [—C(O)(CH$_2$)$_9$ CH$_3$], lauroyl [—C(O)(CH$_2$)$_{10}$CH$_3$], tridecanoyl [—C(O) (CH$_2$)$_{11}$CH$_3$], myristoyl [—C(O)(CH$_2$)$_{12}$CH$_3$], pentadecanoyl [—C(O)(CH$_2$)$_{13}$CH$_3$], palmitoyl [—C(O)(CH$_2$)$_{14}$ CH$_3$], magaroyl [—C(O)(CH$_2$)$_{15}$CH$_3$], stearoyl [—C(O) (CH$_2$)$_{16}$CH$_3$], arachidoyl [—C(O)(CH$_2$)$_{18}$CH$_3$], heneicosanoyl [—C(O)(CH$_2$)$_{19}$CH$_3$], behenoyl [—C(O)(CH$_2$)$_{20}$ CH$_3$], tricosanoyl [—C(O)(CH$_2$)$_{21}$ CH$_3$], tetracosanoyl [—C(O)(CH$_2$)$_{22}$CH$_3$], and the like.

$C_{10}$–$C_{24}$alkenoyl (—C(O)$C_9$–$C_{23}$alkenyl) is intended to include those unsaturated groups of from 10 to 24 carbon atoms in either a straight or branched chain. Examples of such $C_{10}$–$C_{24}$alkenoyl groups include undecylenoyl [—C(O)(CH$_2$)$_7$CH:CHCH$_3$], oleoyl [—C(O)(CH$_2$)$_7$CH:CH (CH$_2$)$_7$CH$_3$], linoloyl [—C(O)(CH$_2$)$_7$CH:CH.CH$_2$.CH:CH (CH$_2$)$_4$CH$_3$], and the like.

The term "$C_2$–$C_8$ alkoxyalkyl" is intended to include those lower alkoxy substituted lower alkyl groups containing from 2 to 8 carbon atoms and from 1 to 3 oxygen atoms in either a straight or branched chain. Examples of such $C_2$–$C_8$ alkoxyalkyl groups include methoxymethyl, methoxyethoxymethyl, methoxyethoxyethoxymethyl, ethoxyethyl, and the like. Examples of $C_1$–$C_8$ alkoxymethyl are methoxymethyl, ethoxymethyl, propoxymethyl, butoxymethyl, pentoxymethyl, butoxymethyl, pentoxymethyl, hexoxymethyl, and heptoxymethyl, and isomeric forms thereof.

The term alkanoyloxymethylene is intended to include those alkanoyloxy substituted methylenes containing from 2 to 8 carbon atoms in either a straight or branched chain. Examples of such $C_2$–$C_8$ alkanoyloxymethylene groups include acetoxymethyl, tert-butoxymethyl, n-propoxymethyl, valeroxymethyl and the like.

The term "substituted benzoyloxymethylene" is intended to include those benzoyloxymethyl groups in which the benzene ring is substituted with from 0 to 3 substituents selected from lower alkyl, trifluoromethyl, $C_1$–$C_7$ alkoxy, nitro, or cyano groups, and halogen atoms.

The term "substituted benzenesulfonyl" is intended to include those benzenesulfonyl groups in which the benzene ring is substituted with from 0 to 3 substituents selected from lower alkyl, trifluoromethyl, $C_1$–$C_7$ alkoxy, nitro, or cyano groups, and halogen atoms.

The term "halogen" is intended to include the halogen atoms fluorine, chlorine, bromine and iodine.

The term "halo $C_1$–$C_7$alkyl" is intended to include those halogen substituted $C_1$–$C_7$ alkyl groups containing from 1 to 7 carbon atoms in either a straight or branched chain and from 1 to 3 halogen atoms. Examples of halo$C_1$–$C_7$alkyl include fluoromethyl, 2-bromoethyl, 3-chloropropyl, 5-iodopentyl, trifluoromethyl, and the like.

The term "$C_2$–$C_8$ alkenyl" is intended to include those lower alkyl groups containing from 2 to 8 carbon atoms in either a straight or branched chain which contains 1 to 2 carbon-carbon double bonds. Examples of such $C_2$–$C_8$ alkenyl groups include allyl, 3-butenyl, 2,4-pentadienyl, hexenyl, and the like.

The term "$C_2$–$C_8$ alkynyl" is intended to include those alkynyl groups containing from 1 to 8 carbon atoms in either a straight or branched chain which contains 1 to 2 carbon-carbon triple bonds. Examples of such $C_2$–$C_8$ alkynyl groups include propargyl, 2-butynyl, 2,4-pentadiynyl, 5-hexynyl, and the like.

Examples of "alkoxycarbonyl" (—C(=O)O—(CH$_2$)$_p$—$C_1$–$C_7$ alkoxy) include ethoxycarbonyl, isopropoxycarbonyl, methoxycarbonyl, butoxycarbonyl, hexoxycarbonyl and the like. $C_1$–$C_7$ alkanoyl is intended to include alkyl groups of from 1 to 7 carbon atoms in either a straight or branched chain. Examples of $C_1$–$C_7$ alkanoyl include acetyl, propionyl, iso-butyryl, valeryl, 5-methylhexanoyl, and the like.

Examples of aminocarbonyl (—C(=O)NR$_4$R$_5$) include dimethylaminocarbonyl, propylmethylaminocarbonyl, dibutylaminocarbonyl, isopropylaminocarbonyl, hexylaminocarbonyl and the like.

Examples of aminothiocarbnyl (—C(=S)NR$_4$R$_5$) include dimethylaminothiocarbonyl, propylmethylaminothiocarbonyl, dibutylaminothiocarbonyl, isopentylaminothiocarbonyl, hexylaminothiocarbonyl and the like.

Examples of the group —P(=X)(R$_2$)(R$_3$) include diethyl thiophosphoryl, phenylmethoxyphosphonyl, 2-thioxo-1,3,2-dioxaphosphorinanyl, N,N-dimethylmethoxyphosphoramidyl, diphenylphosphinyl and the like.

Examples of —SR$_6$ include 2,4-dinitrobenzenesulfenyl, dimethylaminosulfenyl, ethoxycarbonylsulfenyl, trichloromethylsulfenyl, 4-morpholinosulfenyl and the like.

Examples of —SO$_2$NR$_4$R$_5$ include dimethylsulfamoyl, phenylmethylsulfamoyl, 4-morpholinosulfamoyl, piperidinylsulfamoyl and the like.

The term "P containing heterocyclic ring" is intended to include 1,3-dioxa-2-phosphorinane, 1-aza-3-oxa-2-phospholane, 1,3-diaza-2-phospholane, 1-thia-3-oxa-2-phospholane, and the like.

Examples of heterocyclic amine rings according to —NR$_4$R$_5$, —NR'$_4$R'$_5$ and —NR$_7$R$_8$ are:
4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine
thiazolidine,
4-phenyl-1,2,3,6-tetrahydropyridine,
4-phenylpiperidine,
ethyl prolinate,
tetrahydrofurylamine,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine,
N-carboethoxypiperazine, Pharmaceutically acceptable salts means salts useful for administering the compounds of this invention and include mesylate, hydrochloride, hydrobromide, hydroiodide, sulfate, phosphate, acetate, propionate, lactate, maleate, malate, succinate, tartrate, and the like. These salts may be in hydrated form.

Preferred compounds of this invention are compounds of Formula IA and IB are compounds where R$_{14a}$ is hydroxyl and hydrogen, R$_{14b}$ is hydrogen, methyl, and ethyl; R$_{24}$ and R$_{25}$ are hydrogen; R$_{18a}$ is hydrogen, $C_1$–$C_4$ alkyl, $C_2$–$C_4$ alkoxyalkyl, $C_2$–$C_4$ alkenyl or benzyl; and the broken line between carbons 24 and 25 represents a double bond.

Examples of the preferred compounds of this invention are as follows:

14β-methylmarcfortine A,

14β-ethylmarcfortine A, and

14α-hydroxy-14β-ethylmarcfortine A; more preferably

14α-hydroxy-14β-methylmarcfortine A;

14α-hydroxy-14β-methyl-15α-methylmarcfortine A; and most preferably

14α-hydroxymarcfortine A and

14α-hydroxy-15α-methylmarcfortine A.

The following compounds can be prepared from 14α-hydroxymarcfortines, 14α-hydroxy-14β-methylmarcfortines, 14β-methylmarcfortines, 14β-ethylmarcfortines, or 14α-hydroxy-14β-ethylmarcfortines, 14α-hydroxy-14β-methyl-15α-methylmarcfortines, and 14α-hydroxy-15α-methylmarcfortines by employing procedures described in EP 0 354 615 A1 (published 14 Feb 90), and PCT/US92/09483 (WO 93/10120, published 27 May 93), both of which are incorporated herein by reference:

1-acetoxymethyl-14α-hydroxymarcfortine A;

1-diethoxyphosphoryl-14α-hydroxymarcfortine A;

1-dimethylsulfamoyl-14α-hydroxymarcfortine A;

1-cyclopropylcarbonyl-14α-hydroxymarcfortine A;

2-bicyclo[2.2.1]heptanoyl-14α-hydroxymarcfortine A;

1(1-piperidinyl)thiocarbonyl-14α-hydroxymarcfortine A;

1-succinoyl-14α-hydroxymarcfortine A;

1(4-morpholinosulfenyl)-14α-hydroxymarcfortine A;

1(2,4-dinitrobenzenesulfenyl)-14α-hydroxymarcfortine A;

24-propoxy-24,25-dihydro-14α-hydroxymarcfortine A;

1(p-toluenesulfonyl)-14α-hydroxymarcfortine A;

1-acetyl-14α-hydroxymarcfortine A;

1-methyl-14α-hydroxymarcfortine A;

1-benzyl-14α-hydroxymarcfortine A;

1-dimethylcarbamoyl-14α-hydroxymarcfortine A;

1-methoxycarbonyl-14α-hydroxymarcfortine A;

14α-hydroxymarcfortine B;

24,25-dihydro-14α-hydroxymarcfortine B;

24-methoxy-24,25-dihydro-14α-hydroxymarcfortine B;

1-(p-toluenesulfonyl)-14α-hydroxymarcfortine B;

1-ethyl-14α-hydroxymarcfortine B;

1-benzyl-14α-hydroxymarcfortine B;

18a-ethyl-14α-hydroxymarcfortine B;

18a-benzyl-14α-hydroxymarcfortine B;

18a-methoxyethoxymethyl-14α-hydroxymarcfortine B;

18a-allyl-14α-hydroxymarcfortine B;

18a-propargyl-14α-hydroxymarcfortine B;

18a-ethyl-24-methoxy-24,25-dihydro-14α-hydroxymarcfortine B;

1,18a-bis-ethyl-14α-hydroxymarcfortine B;

1,18a-bis-benzyl-14α-hydroxymarcfortine B;

18a-ethyl-24-methoxy-14α-hydroxymarcfortine B;
1-(2,4-dinitrobenzene sulfonyl)-18a-ethyl-24-methoxy-24,25-dihydro-14α-hydroxymarcfortine B;
18a-ethyl-24,25 dihydro-14α-hydroxymarcfortine B;
24,25 dihydro-14α-hydroxymarcfortine C;
1-(p-bromobenzene sulfonyl)-14α-hydroxymarcfortine C;
1-propionyl-14α-hydroxymarcfortine C;
1-propyl-14α-hydroxymarcfortine C;
1-benzyl-14α-hydroxymarcfortine C;
18a-propyl-14α-hydroxymarcfortine C;
18a-benzyl-14α-hydroxymarcfortine C;
18a-methoxyethoxymethyl-14α-hydroxymarcfortine C;
18-allyl-14α-hydroxymarcfortine C;
18a-propargyl-14α-hydroxymarcfortine C;
1,18a-bis-propyl-14α-hydroxymarcfortine C;
1,18a-bis-benzyl-14α-hydroxymarcfortine C;
14α-hydroxymarcfortine C;
1-(4-carbethoxy-1,3-thiazolidinin-3-yl)carbonyl-14α-hydroxymarcfortine A;
1-palmitoyl-14α-hydroxymarcfortine A;
1-(4-morpholinocarbonyl)14α-hydroxymarcfortine A;
1-palmitoyl-14α-hydroxymarcfortine D;
1-(4-morpholinocarbonyl)-14α-hydroxymarcfortine D;
14α-hydroxymarcfortine D;
1-acetoxymethyl-14α-hydroxymarcfortine D;
1-diethoxyphosphoryl-14α-hydroxymarcfortine D;
1-dimethylsulfamoyl-14α-hydroxymarcfortine D;
1-cyclopropylcarbonyl-14α-hydroxymarcfortine D;
2-bicyclo[2.2.1]heptanoyl-14α-hydroxymarcfortine D;
1-(1-piperidinyl)thiocarbonyl-14α-hydroxymarcfortine D;
1-succinoyl-14α-hydroxymarcfortine D;
1-(4-morpholinosulfenyl)-14α-hydroxymarcfortine D;
1-(2,4-dinitrobenzenesulfenyl)-14α-hydroxymarcfortine D;
24-propoxy-24,25-dihydro-14α-hydroxymarcfortine D;
1-(p-toluenesulfonyl)-14α-hydroxymarcfortine D;
1-acetyl-14α-hydroxymarcfortine D;
1-methyl-14α-hydroxymarcfortine D;
1-benzyl-14α-hydroxymarcfortine D;
1-dimethylcarbamoyl-14α-hydroxymarcfortine D;
1-methoxycarbonyl-14α-hydroxymarcfortine D;
1-acetoxymethyl-14α-hydroxy-14β-methylmarcfortine A;
1-diethoxyphosphoryl-14α-hydroxy-14β-methylmarcfortine A;
1-dimethylsulfamoyl-14α-hydroxy-14β-methylmarcfortine A;
1-cyclopropylcarbonyl-14α-hydroxy-14β-methylmarcfortine A;
2-bicyclo[2.2.1]heptanoyl-14α-hydroxy-14β-methylmarcfortine A;
1-(1-piperidinyl)thiocarbonyl-14α-hydroxy-14β-methylmarcfortine A;
1-succinoyl-14α-hydroxy-14β-methylmarcfortine A;
1-(4-morpholinosulfenyl)-14α-hydroxy-14β-methylmarcfortine A;
1-(2,4-dinitrobenzenesulfenyl)-14α-hydroxy-14β-methylmarcfortine A;
24-propoxy-24,25-dihydro-14α-hydroxy-14β-methylmarcfortine A;
1-(p-toluenesulfonyl)-14α-hydroxy-14β-methylmarcfortine A;
1-acetyl-14α-hydroxy-14β-methylmarcfortine A;
1-methyl-14α-hydroxy-14β-methylmarcfortine A;
1-benzyl-14α-hydroxy-14β-methylmarcfortine A;
1-dimethylcarbamoyl-14α-hydroxy-14β-methylmarcfortine A;
1-methoxycarbonyl-14α-hydroxy-14β-methylmarcfortine A;
14α-hydroxy-14β-methylmarcfortine B;
24,25-dihydro-14α-hydroxy-14β-methylmarcfortine B;
24-methoxy-24,25-dihydro-14α-hydroxy-14β-methylmarcfortine B;
1-(p-toluenesulfonyl)-14α-hydroxy-14β-methylmarcfortine B;
1-ethyl-14α-hydroxy-14β-methylmarcfortine B;
1-benzyl-14α-hydroxy-14β-methylmarcfortine B;
18a-ethyl-14α-hydroxy-14β-methylmarcfortine B;
18a-benzyl-14α-hydroxy-14β-methylmarcfortine B;
18a-methoxyethoxymethyl-14α-hydroxy-14β-methylmarcfortine B;
18a-allyl-14α-hydroxy-14β-methylmarcfortine B;
18a-propargyl-14α-hydroxy-14β-methylmarcfortine B;
18a-ethyl-24-methoxy-24,25-dihydro-14α-hydroxy-14β-methylmarcfortine B;
1,18a-bis-ethyl-14α-hydroxy-14β-methylmarcfortine B;
1,18a-bis-benzyl-14α-hydroxy-14β-methylmarcfortine B;
18a-ethyl-24-methoxy-14α-hydroxy-14β-methylmarcfortine B;
1-(2,4-dinitrobenzene sulfonyl)-18a-ethyl-24-methoxy-24,25-dihydro-14α-hydroxy-14β-methylmarcfortine B;
18a-ethyl-24,25 dihydro-14α-hydroxy-14β-methylmarcfortine B;
24,25-dihydro-14α-hydroxy-14β-methylmarcfortine C;
1-(p-bromobenzene sulfonyl)-14α-hydroxy-14β-methylmarcfortine C;
1-propionyl-14α-hydroxy-14β-methylmarcfortine C;
1-propyl-14α-hydroxy-14β-methylmarcfortine C;
1-benzyl-14α-hydroxy-14β-methylmarcfortine C;
18a-propyl-14α-hydroxy-14β-methylmarcfortine C;
18a-benzyl-14α-hydroxy-14β-methylmarcfortine C;
18a-methoxyethoxymethyl-14α-hydroxy-14β-methylmarcfortine C;
18-allyl-14α-hydroxy-14β-methylmarcfortine C;
18a-propargyl-14α-hydroxy-14β-methylmarcfortine C;
1,18a-bis-propyl-14α-hydroxy-14β-methylmarcfortine C;
1,18a-bis-benzyl-14α-hydroxy-14β-methylmarcfortine C;
14α-hydroxy-14β-methylmarcfortine C;
1-palmitoyl-14α-hydroxy-14β-methylmarcfortine A;
1-(4-morpholinocarbonyl)-14α-hydroxy-14β-methylmarcfortine A;
1-palmitoyl-14α-hydroxy-14β-methylmarcfortine D;

1-(4-morpholinocarbonyl)-14α-hydroxy-14β-methylmarcfortine D;

14α-hydroxy-14β-methylmarcfortine D;

1-acetoxymethyl-14α-hydroxy-14β-methylmarcfortine D;

1-diethoxyphosphoryl-14α-hydroxy-14β-methylmarcfortine D;

1-dimethylsulfamoyl-14α-hydroxy-14β-methylmarcfortine D;

1-cyclopropylcarbonyl-14α-hydroxy-14β-methylmarcfortine D;

2-bicyclo[2.2.1]heptanoyl-14α-hydroxy-14β-methylmarcfortine D;

1-(1-piperidinyl)thiocarbonyl-14α-hydroxy-14β-methylmarcfortine D;

1-succinoyl-14α-hydroxy-14β-methylmarcfortine D;

1-(4-morpholinosulfenyl)-14α-hydroxy-14β-methylmarcfortine D;

1-(2,4-dinitrobenzenesulfenyl)-14α-hydroxy-14β-methylmarcfortine D;

24-propoxy-24,25-dihydro-14α-hydroxy-14β-methylmarcfortine D;

1-(p-toluenesulfonyl)-14α-hydroxy-14β-methylmarcfortine D;

1-acetyl-14α-hydroxy-14β-methylmarcfortine D;

1-methyl-14α-hydroxy-14β-methylmarcfortine D;

1-benzyl-14α-hydroxy-14β-methylmarcfortine D;

1-dimethylcarbamoyl-14α-hydroxy-14β-ethylmarcfortine D;

1-methoxycarbonyl-14α-hydroxy-14β-ethylmarcfortine D;

1-acetoxymethyl-14α-hydroxy-14β-ethylmarcfortine A;

1-diethoxyphosphoryl-14α-hydroxy-14β-ethylmarcfortine A;

1-dimethylsulfamoyl-14α-hydroxy-14β-ethylmarcfortine A;

1-cyclopropylcarbonyl-14α-hydroxy-14β-ethylmarcfortine A;

2-bicyclo[2.2.1]heptanoyl-14α-hydroxy-14β-ethylmarcfortine A;

1-(1-piperidinyl)thiocarbonyl-14α-hydroxy-14β-ethylmarcfortine A;

1-succinoyl-14α-hydroxy-14β-ethylmarcfortine A;

1-(4-morpholinosulfenyl)-14α-hydroxy-14β-ethylmarcfortine A;

1-(2,4-dinitrobenzenesulfenyl)-14α-hydroxy-14β-ethylmarcfortine A;

24-propoxy-24,25-dihydro-14α-hydroxy-14β-ethylmarcfortine A;

1-(p-toluenesulfonyl)-14α-hydroxy-14β-ethylmarcfortine A;

1-acetyl-14α-hydroxy-14β-ethylmarcfortine A;

1-methyl-14α-hydroxy-14β-ethylmarcfortine A;

1-benzyl-14α-hydroxy-14β-ethylmarcfortine A;

1-dimethylcarbamoyl-14α-hydroxy-14β-ethylmarcfortine A;

1-methoxycarbonyl-14α-hydroxy-14β-ethylmarcfortine A;

14α-hydroxy-14β-ethylmarcfortine B;

24,25-dihydro-14α-hydroxy-14β-ethylmarcfortine B;

24-methoxy-24,25-dihydro-14α-hydroxy-14β-ethylmarcfortine B;

1-(p-toluenesulfonyl)-14α-hydroxy-14β-ethylmarcfortine B;

1-ethyl-14α-hydroxy-14β-ethylmarcfortine B;

1-benzyl-14α-hydroxy-14β-ethylmarcfortine B;

18a-ethyl-14α-hydroxy-14β-ethylmarcfortine B;

18a-benzyl-14α-hydroxy-14β-ethylmarcfortine B;

18a-methoxyethoxymethyl-14α-hydroxy-14β-ethylmarcfortine B;

18a-allyl-14α-hydroxy-14β-ethylmarcfortine B;

18a-propargyl-14α-hydroxy-14β-ethylmarcfortine B;

18a-ethyl-24-methoxy-24,25-dihydro-14α-hydroxy-14β-ethylmarcfortine B;

1,18a-bis-ethyl-14α-hydroxy-14β-ethylmarcfortine B;

1,18a-bis-benzyl-14α-hydroxy-14β-ethylmarcfortine B;

18a-ethyl-24-methoxy-14α-hydroxy-14β-ethylmarcfortine B;

1-(2,4-dinitrobenzene sulfonyl)-18a-ethyl-24-methoxy-24,25-dihydro-14α-hydroxy-14β-ethylmarcfortine B;

18a-ethyl-24,25 dihydro-14α-hydroxy-14β-ethylmarcfortine B;

24,25 dihydro-14α-hydroxy-14β-ethylmarcfortine C;

1-(p-bromobenzene sulfonyl)-14α-hydroxy-14β-ethylmarcfortine C;

1-propionyl-14α-hydroxy-14β-ethylmarcfortine C;

1-propyl-14α-hydroxy-14β-ethylmarcfortine C;

1-benzyl-14α-hydroxy-14β-ethylmarcfortine C;

18a-propyl-14α-hydroxy-14β-ethylmarcfortine C;

18a-benzyl-14α-hydroxy-14β-ethylmarcfortine C;

18a-methoxyethoxymethyl-14α-hydroxy-14β-ethylmarcfortine C;

18-allyl-14α-hydroxy-14β-ethylmarcfortine C;

18a-propargyl-14α-hydroxy-14β-ethylmarcfortine C;

1,18a-bis-propyl-14α-hydroxy-14β-ethylmarcfortine C;

1,18a-bis-benzyl-14α-hydroxy-14β-ethylmarcfortine C;

14α-hydroxy-14β-ethylmarcfortine C;

1-palmitoyl-14α-hydroxy-14β-ethylmarcfortine A;

1-(4-morpholinocarbonyl)-14α-hydroxy-14β-ethylmarcfortine A;

1-palmitoyl-14α-hydroxy-14β-ethylmarcfortine D;

1-(4-morpholinocarbonyl)-14α-hydroxy-14β-ethylmarcfortine D;

14α-hydroxy-14β-ethylmarcfortine D;

1-acetoxymethyl-14α-hydroxy-14β-ethylmarcfortine D;

1-diethoxyphosphoryl-14α-hydroxy-14β-ethylmarcfortine D;

1-dimethylsulfamoyl-14α-hydroxy-14β-ethylmarcfortine D;

1-cyclopropylcarbonyl-14α-hydroxy-14β-ethylmarcfortine D;

2-bicyclo[2.2.1]heptanoyl-14α-hydroxy-14β-ethylmarcfortine D;

1-(1-piperidinyl)thiocarbonyl-14α-hydroxy-14β-ethylmarcfortine D;

1-succinoyl-14α-hydroxy-14β-ethylmarcfortine D;

1-(4-morpholinosulfenyl)-14α-hydroxy-14β-ethylmarcfortine D;

1-(2,4-dinitrobenzenesulfenyl)-14α-hydroxy-14β-ethylmarcfortine D;

24-propoxy-24,25-dihydro-14α-hydroxy-14β-ethylmarcfortine D;
1-(p-toluenesulfonyl)-14α-hydroxy-14β-ethylmarcfortine D;
1-acetyl-14α-hydroxy-14β-ethylmarcfortine D;
1-methyl-14α-hydroxy-14β-ethylmarcfortine D;
1-benzyl-14α-hydroxy-14β-ethylmarcfortine D;
1-dimethylcarbamoyl-14α-hydroxy-14β-ethylmarcfortine D;
1-methoxycarbonyl-14α-hydroxy-14β-ethylmarcfortine D;
1-acetoxymethyl-14β-methylmarcfortine A;
1-diethoxyphosphoryl-14β-methylmarcfortine A;
1-dimethylsulfamoyl-14β-methylmarcfortine A;
1-cyclopropylcarbonyl-14β-methylmarcfortine A;
2-bicyclo[2.2.1]heptanoyl-14β-methylmarcfortine A;
1-(1-piperidinyl)thiocarbonyl-14β-methylmarcfortine A;
1-succinoyl-14β-methylmarcfortine A;
1-(4-morpholinosulfenyl)-14β-methylmarcfortine A;
1-(2,4-dinitrobenzenesulfenyl)-14β-methylmarcfortine A;
24-propoxy-24,25-dihydro-14β-methylmarcfortine A;
1-(p-toluenesulfonyl)-14β-methylmarcfortine A;
1-acetyl-14β-methylmarcfortine A;
1-methyl-14β-methylmarcfortine A;
1-benzyl-14β-methylmarcfortine A;
1-dimethylcarbamoyl-14β-methylmarcfortine A;
1-methoxycarbonyl-14β-methylmarcfortine A;
14β-methylmarcfortine B;
24,25-dihydro-14β-methylmarcfortine B;
24-methoxy-24,25-dihydro-14β-methylmarcfortine B;
1-(p-toluenesulfonyl)-14β-methylmarcfortine B;
1-ethyl-14β-methylmarcfortine B;
1-benzyl-14β-methylmarcfortine B;
18a-ethyl-14β-methylmarcfortine B;
18a-benzyl-14β-methylmarcfortine B;
18a-methoxyethoxymethyl-14β-methylmarcfortine B;
18a-allyl-14β-methylmarcfortine B;
18a-propargyl-14β-methylmarcfortine B;
18a-ethyl-24-methoxy-24,25-dihydro-14β-methylmarcfortine B;
1,18a-bis-ethyl-14β-methylmarcfortine B;
1,18a-bis-benzyl-14β-methylmarcfortine B;
18a-ethyl-24-methoxy-14β-methylmarcfortine B;
1-(2,4-dinitrobenzene sulfonyl)-18a-ethyl-24-methoxy-24,25-dihydro-14β-methylmarcfortine B;
18a-ethyl-24,25 dihydro-14β-methylmarcfortine B;
24,25 dihydro-14β-methylmarcfortine C;
1-(p-bromobenzene sulfonyl)-14β-methylmarcfortine C;
1-propionyl-14β-methylmarcfortine C;
1-propyl-14β-methylmarcfortine C;
1-benzyl-14β-methylmarcfortine C;
18a-propyl-14β-methylmarcfortine C;
18a-benzyl-14β-methylmarcfortine C;
18a-methoxyethoxymethyl-14β-methylmarcfortine C;
18-allyl-14β-methylmarcfortine C;
18a-propargyl-14β-methylmarcfortine C;
1,18a-bis-propyl-14β-methylmarcfortine C;
1,18a-bis-benzyl-14β-methylmarcfortine C;
14β-methylmarcfortine C;
1-palmitoyl-14β-methylmarcfortine A;
1-(4-morpholinocarbonyl)-14β-methylmarcfortine A;
1-palmitoyl-14β-methylmarcfortine D;
1-(4-morpholinocarbonyl)-14β-methylmarcfortine D;
14β-methylmarcfortine D;
1-acetoxymethyl-14β-methylmarcfortine D;
1-diethoxyphosphoryl-14β-methylmarcfortine D;
1-dimethylsulfamoyl-14β-methylmarcfortine D;
1-cyclopropylcarbonyl-14β-methylmarcfortine D;
2-bicyclo[2.2.1]heptanoyl-14β-methylmarcfortine D;
1-(1-piperidinyl)thiocarbonyl-14β-methylmarcfortine D;
1-succinoyl-14β-methylmarcfortine D;
1-(4-morpholinosulfenyl)-14β-methylmarcfortine D;
1-(2,4-dinitrobenzenesulfenyl)-14β-methylmarcfortine D;
24-propoxy-24,25-dihydro-14β-methylmarcfortine D;
1-(p-toluenesulfonyl)-14β-methylmarcfortine D;
1-acetyl-14β-methylmarcfortine D;
1-methyl-14β-methylmarcfortine D;
1-benzyl-14β-methylmarcfortine D;
1-dimethylcarbamoyl-14β-methylmarcfortine D;
1-methoxycarbonyl-14β-methylmarcfortine D;
1-acetoxymethyl-14β-ethylmarcfortine A;
1-diethoxyphosphoryl-14β-ethylmarcfortine A;
1-dimethylsulfamoyl-14β-ethylmarcfortine A;
1-cyclopropylcarbonyl-14β-ethylmarcfortine A;
2-bicyclo[2.2.1]heptanoyl-14β-ethylmarcfortine A;
1-(1-piperidinyl)thiocarbonyl-14β-ethylmarcfortine A;
1-succinoyl-14β-ethylmarcfortine A;
1-(4-morpholinosulfenyl)-14β-ethylmarcfortine A;
1-(2,4-dinitrobenzenesulfenyl)-14β-ethylmarcfortine A;
24-propoxy-24,25-dihydro-14β-ethylmarcfortine A;
1-(p-toluenesulfonyl)-14β-ethylmarcfortine A;
1-acetyl-14β-ethylmarcfortine A;
1-methyl-14β-ethylmarcfortine A;
1-benzyl-14β-ethylmarcfortine A;
1-dimethylcarbamoyl-14β-ethylmarcfortine A;
1-methoxycarbonyl-14β-ethylmarcfortine A;
14β-ethylmarcfortine B;
24,25-dihydro-14β-ethylmarcfortine B;
24-methoxy-24,25-dihydro-14β-ethylmarcfortine B;
1-(p-toluenesulfonyl)-14β-ethylmarcfortine B;
1-ethyl-14β-ethylmarcfortine B;
1-benzyl-14β-ethylmarcfortine B;
18a-ethyl-14β-ethylmarcfortine B;
18a-benzyl-14β-ethylmarcfortine B;
18a-methoxyethoxymethyl-14β-ethylmarcfortine B;
18a-ally-14β-ethylmarcfortine B;
18a-propargyl-14β-ethylmarcfortine B;
18a-ethyl-24-methoxy-24,25-dihydro-14β-ethylmarcfortine B;
1,18a-bis-ethyl-14β-ethylmarcfortine B;
1,18a-bis-benzyl-14β-ethylmarcfortine B;
18a-ethyl-24-methoxy-14β-ethylmarcfortine B;
1-(2,4-dinitrobenzene sulfonyl)-18a-ethyl-24-methoxy-24,25-dihydro-14β-ethylmarcfortine B;

18a-ethyl-24,25 dihydro-14β-ethylmarcfortine B;
24,25 dihydro-14β-ethylmarcfortine C;
1-(p-bromobenzene sulfonyl)-14β-ethylmarcfortine C;
1-propionyl-14β-ethylmarcfortine C;
1-propyl-14β-ethylmarcfortine C;
1-benzyl-14β-ethylmarcfortine C;
18a-propyl-14β-ethylmarcfortine C;
18a-benzyl-14β-ethylmarcfortine C;
18a-methoxyethoxymethyl-14β-ethylmarcfortine C;
18-allyl-14β-ethylmarcfortine C;
18a-propargyl-14β-ethylmarcfortine C;
1,18a-bis-propyl-14β-ethylmarcfortine C;
1,18a-bis-benzyl-14β-ethylmarcfortine C;
14β-ethylmarcfortine C;
1-palmitoyl-14β-ethylmarcfortine A;
1-(4-morpholinocarbonyl)-14β-ethylmarcfortine A;
1-palmitoyl-14β-ethylmarcfortine D;
1-(4-morpholinocarbonyl)-14β-ethylmarcfortine D;
14β-ethylmarcfortine D;
1-acetoxymethyl-14β-ethylmarcfortine D;
1-diethoxyphosphoryl-14β-ethylmarcfortine D;
1-dimethylsulfamoyl-14β-ethylmarcfortine D;
1-cyclopropylcarbonyl-14β-ethylmarcfortine D;
2-bicyclo[2.2.1]heptanoyl-14β-ethylmarcfortine D;
1-(1-piperidinyl)thiocarbonyl-14β-ethylmarcfortine D;
1-succinoyl-14β-ethylmarcfortine D;
1-(4-morpholinosulfenyl)-14β-ethylmarcfortine D;
1-(2,4-dinitrobenzenesulfenyl)-14β-ethylmarcfortine D;
24-propoxy-24,25-dihydro-14β-ethylmarcfortine D;
1-(p-toluenesulfonyl)-14β-ethylmarcfortine D;
1-acetyl-14β-ethylmarcfortine D;
1-methyl-14β-ethylmarcfortine D;
1-benzyl-14β-ethylmarcfortine D;
1-dimethylcarbamoyl-14β-ethylmarcfortine D;
1-methoxycarbonyl-14β-ethylmarcfortine D;
1-acetoxymethyl-14α-O-methylmarcfortine A;
14α-O-methylmarcfortine A;
14α-O-methyl-14β-methylmarcfortine A;
14α-O-methyl-14β-ethylmarcfortine A;
1-diethoxyphosphoryl-14α-O-methylmarcfortine A;
1-dimethylsulfamoyl-14α-O-methylmarcfortine A;
1-cyclopropylcarbonyl-14α-O-methylmarcfortine A;
2-bicyclo[2.2.1]heptanoyl-14α-O-methylmarcfortine A;
1-(1-piperidinyl)thiocarbonyl-14α-O-methylmarcfortine A;
1-succinoyl-14α-O-methylmarcfortine A;
1-(4-morpholinosulfenyl)-14α-O-methylmarcfortine A;
1-(2,4-dinitrobenzenesulfenyl)-14α-O-methylmarcfortine A;
24-propoxy-24,25-dihydro-14α-O-methylmarcfortine A;
1-(p-toluenesulfonyl)-14α-O-methylmarcfortine A;
1-acetyl-14α-O-methylmarcfortine A;
1-methyl-14α-O-methylmarcfortine A;
1-benzyl-14α-O-methylmarcfortine A;
1-dimethylcarbamoyl-14α-O-methylmarcfortine A;
1-methoxycarbonyl-14α-O-methylmarcfortine A;
14α-O-methylmarcfortine B;

24,25-dihydro-14α-O-methylmarcfortine B;
24-methoxy-24,25-dihydro-14α-O-methylmarcfortine B;
1-(p-toluenesulfonyl)-14α-O-methylmarcfortine B;
1-ethyl-14α-O-methylmarcfortine B;
1-benzyl-14α-O-methylmarcfortine B;
18a-ethyl-14α-O-methylmarcfortine B;
18a-benzyl-14α-O-methylmarcfortine B;
18a-methoxyethoxymethyl-14α-O-methylmarcfortine B;
18a-allyl-14α-O-methylmarcfortine B;
18a-propargyl-14α-O-methylmarcfortine B;
18a-ethyl-24-methoxy-24,25-dihydro-14α-O-methylmarcfortine B;
1,18a-bis-ethyl-14α-O-methylmarcfortine B;
1,18a-bis-benzyl-14α-O-methylmarcfortine B;
18a-ethyl-24-methoxy-14α-O-methylmarcfortine B;
1(2,4-dinitrobenzene sulfonyl)-18a-ethyl-24-methoxy-24,25-dihydro-14α-O-methylmarcfortine B;
18a-ethyl-24,25 dihydro-14α-O-methylmarcfortine B;
24,25 dihydro-14α-O-methylmarcfortine C;
1-(p-bromobenzene sulfonyl)-14α-O-methylmarcfortine C;
1-propionyl-14α-O-methylmarcfortine C;
1-propyl-14α-O-methylmarcfortine C;
1-benzyl-14α-O-methylmarcfortine C;
18a-propyl-14α-O-methylmarcfortine C;
18a-benzyl-14α-O-methylmarcfortine C;
18a-methoxyethoxymethyl-14α-O-methylmarcfortine C;
18-allyl-14α-O-methylmarcfortine C;
18-propargyl-14α-O-methylmarcfortine C;
1,18a-bis-propyl-14α-O-methylmarcfortine C;
1,18a-bis-benzyl-14α-O-methylmarcfortine C;
14α-O-methylmarcfortine C;
1-palmitoyl-14α-O-methylmarcfortine A;
1-(4-morpholinocarbonyl)-14α-O-methylmarcfortine A;
1-palmitoyl-14α-O-methylmarcfortine D;
1-(4-morpholincarbonyl)-14α-O-methylmarcfortine D;
14α-O-methylmarcfortine D;
1-acetoxymethyl-14α-O-methylmarcfortine D;
1-diethoxyphosphoryl-14α-O-methylmarcfortine D;
1-dimethylsulfamoyl-14α-O-methylmarcfortine D;
1-cyclopropylcarbonyl-14α-O-methylmarcfortine D;
2-bicyclo[2.2.1]-heptanoyl-14α-O-methylmarcfortine D;
1-(1-piperidinyl)thiocarbonyl-14α-O-methylmarcfortine D;
1-succinoyl-14α-O-methylmarcfortine D;
1-(4-morpholinosulfenyl)-14α-O-methylmarcfortine D;
1-(2,4-dinitrobenzenesulfenyl)-14α-O-methylmarcfortine D;
24-propoxy-24,25-dihydro-14α-O-methylmarcfortine D;
1-(p-toluenesulfonyl)-14α-O-methylmarcfortine D;
1-acetyl-14α-O-methylmarcfortine D;
1-methyl-14α-O-methylmarcfortine D;
1-benzyl-14α-O-methylmarcfortine D;
1-dimethylcarbamoyl-14α-O-methylmarcfortine D;
1-methoxycarbonyl-14α-O-methylmarcfortine D;
1-acetoxymethyl-14α-O-methyl-14β-methylmarcfortine A;

1-diethoxyphosphoryl-14α-O-methyl-14β-methylmarcfortine A;
1-dimethylsulfamoyl-14α-O-methyl-14β-methylmarcfortine A;
1-cyclopropylcarbonyl-14α-O-methyl-14β-methylmarcfortine A;
2-bicyclo[2.2.1]heptanoyl-14α-O-methyl-14β-methylmarcfortine A;
1-(1-piperidinyl)thiocarbonyl-14α-O-methyl-14β-methylmarcfortine A;
1-succinoyl-14α-O-methyl-14β-methylmarcfortine A;
1-(4-morpholinosulfenyl)-14α-O-methyl-14β-methylmarcfortine A;
1-(2,4-dinitrobenzenesulfenyl)-14α-O-methyl-14β-methylmarcfortine A;
24-propoxy-24,25-dihydro-14α-O-methyl-14β-methylmarcfortine A;
1-(p-toluenesulfonyl)-14α-O-methyl-14β-methylmarcfortine A;
1-acetyl-14α-O-methyl-14β-methylmarcfortine A;
1-methyl-14α-O-methyl-14β-methylmarcfortine A;
1-benzyl-14α-O-methyl-14β-methylmarcfortine A;
1-dimethylcarbamoyl-14α-O-methyl-14β-methylmarcfortine A;
1-methoxycarbonyl-14α-O-methyl-14β-methylmarcfortine A;
14α-O-methyl-14β-methylmarcfortine B;
24,25-dihydro-14α-O-methyl-14β-methylmarcfortine B;
24-methoxy-24,25-dihydro-14α-O-methyl-14β-methylmarcfortine B;
1-(p-toluenesulfonyl)-14α-O-methyl-14β-methylmarcfortine B;
1-ethyl-14α-O-methyl-14β-methylmarcfortine B;
1-benzyl-14α-O-methyl-14β-methylmarcfortine B;
18a-ethyl-14α-O-methyl-14β-methylmarcfortine B;
18a-benzyl-14α-O-methyl-14β-methylmarcfortine B;
18a-methoxyethoxymethyl-14α-O-methyl-14β-methylmarcfortine B;
18a-allyl-14α-O-methyl-14β-methylmarcfortine B;
18a-propargyl-14α-O-methyl-14β-methylmarcfortine B;
18a-ethyl-24-methoxy-24,25-dihydro-14α-O-methyl-14β-methylmarcfortine B;
1,18a-bis-ethyl-14α-O-methyl-14β-methylmarcfortine B;
1,18a-bis-benzyl-14α-O-methyl-14β-methylmarcfortine B;
18a-ethyl-24-methoxy-14α-O-methyl-14β-methylmarcfortine B;
1-(2,4-dinitrobenzene sulfonyl)-18a-ethyl-24-methoxy-24,25-dihydro-14α-O-methyl-14β-methylmarcfortine B;
18a-ethyl-24,25 dihydro-14α-O-methyl-14β-methylmarcfortine B;
24,25 dihydro-14α-O-methyl-14β-methylmarcfortine C;
1-(p-bromobenzene sulfonyl)-14α-O-methyl-14β-methylmarcfortine C;
1-propionyl-14α-O-methyl-14β-methylmarcfortine C;
1-propyl-14α-O-methyl-14β-methylmarcfortine C;
1-benzyl-14α-O-methyl-14β-methylmarcfortine C;
18a-propyl-14α-O-methyl-14β-methylmarcfortine C;
18a-benzyl-14α-O-methyl-14β-methylmarcfortine C;
18a-methoxyethoxymethyl-14α-O-methyl-14β-methylmarcfortine C;
18-allyl-14α-O-methyl-14β-methylmarcfortine C;
18a-propargyl-14α-O-methyl-14β-methylmarcfortine C;
1,18a-bis-propyl-14α-O-methyl-14β-methylmarcfortine C;
1,18a-bis-benzyl-14α-O-methyl-14β-methylmarcfortine C;
14α-O-methyl-14β-methylmarcfortine C;
1-palmitoyl-14α-O-methyl-14β-methylmarcfortine A;
1-(4-morpholinocarbonyl)-14α-O-methyl-14β-methylmarcfortine A;
1-palmitoyl-14α-O-methyl-14β-methylmarcfortine D;
1-(4-morpholinocarbonyl)-14α-O-methyl-14β-methylmarcfortine D;
14α-O-methyl-14β-methylmarcfortine D;
1-acetoxymethyl-14α-O-methyl-14β-methylmarcfortine D;
1-diethoxyphosphoryl-14α-O-methyl-14β-methylmarcfortine D;
1-dimethylsulfamoyl-14α-O-methyl-14β-methylmarcfortine D;
1-cyclopropylcarbonyl-14α-O-methyl-14β-methylmarcfortine D;
2-bicyclo[2.2.1]heptanoyl-14α-O-methyl-14β-methylmarcfortine D;
1-(1-piperidinyl)thiocarbonyl-14α-O-methyl-14β-methylmarcfortine D;
1-succinoyl-14α-O-methyl-14β-methylmarcfortine D;
1-(4-morpholinosulfenyl)-14α-O-methyl-14β-methylmarcfortine D;
1-(2,4-dinitrobenzenesulfenyl)-14α-O-methyl-14β-methylmarcfortine D;
24-propoxy-24,25-dihydro-14α-O-methyl-14β-methylmarcfortine D;
1-(p-toluenesulfonyl)-14α-O-methyl-14β-methylmarcfortine D;
1-acetyl-14α-O-methyl-14β-methylmarcfortine D;
1-methyl-14α-O-methyl-14β-methylmarcfortine D;
1-benzyl-14α-O-methyl-14β-methylmarcfortine D;
1-dimethylcarbamoyl-14α-O-methyl-14β-ethylmarcfortine D;
1-methoxycarbonyl-14α-O-methyl-14β-ethylmarcfortine D;
1-acetoxymethyl-14α-O-methyl-14β-ethylmarcfortine A;
1-diethoxyphosphoryl-14α-O-methyl-14β-ethylmarcfortine A;
1-dimethylsulfamoyl-14α-O-methyl-14β-ethylmarcfortine A;
1-cyclopropylcarbonyl-14α-O-methyl-14β-ethylmarcfortine A;
2-bicyclo[2.2.1]heptanoyl-14α-O-methyl-14β-ethylmarcfortine A;
1-(1-piperidinyl)thiocarbonyl-14α-O-methyl-14β-ethylmarcfortine A;
1-succinoyl-14α-O-methyl-14β-ethylmarcfortine A;
1-(4-morpholinosulfenyl)-14α-O-methyl-14β-ethylmarcfortine A;
1-(2,4-dinitrobenzenesulfenyl)-14α-O-methyl-14β-ethylmarcfortine A;

24-propoxy-24,25-dihydro-14α-O-methyl-14β-ethylmarcfortine A;

1-(p-toluenesulfonyl)-14α-O-methyl-14β-ethylmarcfortine A;

1-acetyl-14α-O-methyl-14β-ethylmarcfortine A;

1-methyl-14α-O-methyl-14β-ethylmarcfortine A;

1-benzyl-14α-O-methyl-14β-ethylmarcfortine A;

1-dimethylcarbamoyl-14α-O-methl-14β-ethylmarcfortine A;

1-methoxycarbonyl-14α-O-methyl-14β-ethylmarcfortine A;

14α-O-methyl-14β-ethylmarcfortine B;

24,25-dihydro-14α-O-methyl-14β-ethylmarcfortine B;

24-methoxy-24,25-dihydro-14α-O-methyl-14β-ethylmarcfortine B;

1-(p-toluenesulfonyl)-14α-O-methyl-14β-ethylmarcfortine B;

1-ethyl-14α-O-methyl-14β-ethylmarcfortine B;

1-benzyl-14α-O-methyl-14β-ethylmarcfortine B;

18a-ethyl-14α-O-methyl-14β-ethylmarcfortine B;

18a-benzyl-14α-O-methyl-14β-ethylmarcfortine B;

18a-methoxyethoxymethyl-14α-O-methyl-14β-ethylmarcfortine B;

18a-allyl-14α-O-methyl-14β-ethylmarcfortine B;

18a-propargyl-14α-O-methyl-14β-ethylmarcfortine B;

18a-ethyl-24-methoxy-24,25-dihydro-14α-O-methyl-14β-ethylmarcfortine B;

1,18a-bis-ethyl-14α-O-methyl-14β-ethylmarcfortine B;

1,18a-bis-benzyl-14α-O-methyl-14β-ethylmarcfortine B;

18a-ethyl-24-methoxy-14α-O-methyl-14β-ethylmarcfortine B;

1-(2,4-dinitrobenzene sulfonyl)-18a-ethyl-24-methoxy-24,25-dihydro-14α-O-methyl-14β-ethylmarcfortine B;

18a-ethyl-24,25 dihydro-14α-O-methyl-14β-ethylmarcfortine B;

24,25 dihydro-14α-O-methyl-14β-ethylmarcfortine C;

1-(p-bromobenzene sulfonyl)-14α-O-methyl-14β-ethylmarcfortine C;

1-propionyl-14α-O-methyl-14β-ethylmarcfortine C;

1-propyl-14α-O-methyl-14β-ethylmarcfortine C;

1-benzyl-14α-O-methyl-14β-ethylmarcfortine C;

18a-propyl-14α-O-methyl-14β-ethylmarcfortine C;

18a-benzyl-14α-O-methyl-14β-ethylmarcfortine C;

18a-methoxyethoxymethyl-14α-O-methyl-14β-ethylmarcfortine C;

18-allyl-14α-O-methyl-14β-ethylmarcfortine C;

18a-propargyl-14α-O-methyl-14β-ethylmarcfortine C;

1,18a-bis-propyl-14α-O-methyl-14β-ethylmarcfortine C;

1,18a-bis-benzyl-14α-O-methyl-14β-ethylmarcfortine C;

14α-O-methyl-14β-ethylmarcfortine C;

1-palmitoyl-14α-O-methyl-14β-ethylmarcfortine A;

1-(4-morpholinocarbonyl)-14α-O-methyl-14β-ethylmarcfortine A;

1-palmitoyl-14α-O-methyl-14β-ethylmarcfortine D;

1-(4-morpholinocarbonyl)-14α-O-methyl-14β-ethylmarcfortine D;

14α-O-methyl-14β-ethylmarcfortine D;

1-acetoxymethyl-14α-O-methyl-14β-ethylmarcfortine D;

1-diethoxyphosphoryl-14α-O-methyl-14β-ethylmarcfortine D;

1-dimethylsulfamoyl-14α-O-methyl-14β-ethylmarcfortine D;

1-cyclopropylcarbonyl-14α-O-methyl-14β-ethylmarcfortine D;

2-bicyclo[2.2.1]heptanoyl-14α-O-methyl-14β-ethylmarcfortine D;

1-(1-piperidinyl)thiocarbonyl-14α-O-methyl-14β-ethylmarcfortine D;

1-succinoyl-14α-O-methyl-14β-ethylmarcfortine D;

1-(4-morpholinosulfenyl)-14α-O-methyl-14β-ethylmarcfortine D;

1-(2,4-dinitrobenzenesulfenyl)-14α-O-methyl-14β-ethylmarcfortine D;

24-propoxy-24,25-dihydro-14α-O-methyl-14β-ethylmarcfortine D;

1-(p-toluenesulfonyl)-14α-O-methyl-14β-ethylmarcfortine D;

1-acetyl-14α-O-methyl-14β-ethylmarcfortine D;

1-methyl-14α-O-methyl-14β-ethylmarcfortine D;

1-benzyl-14α-O-methyl-14β-ethylmarcfortine D;

1-dimethylcarbamoyl-14α-O-methyl-14β-ethylmarcfortine D;

1-methoxycarbonyl-14α-O-methyl-14β-ethylmarcfortine D;

1-acetoxymethyl-14α-O-allylmarcfortine A;

14α-O-allylmarcfortine A;

14α-O-allyl-14β-methylmarcfortine A;

14α-O-allyl-14β-ethylmarcfortine A;

1-diethoxyphosphoryl-14α-O-allylmarcfortine A;

1-dimethylsulfamoyl-14α-O-allylmarcfortine A;

1-cyclopropylcarbonyl-14α-O-allylmarcfortine A;

2-bicyclo[2.2.1]heptanoyl-14α-O-allylmarcfortine A;

1-(1-piperidinyl)thiocarbonyl-14α-O-allylmarcfortine A;

1-succinoyl-14α-O-allylmarcfortine A;

1-(4-morpholinosulfenyl)-14α-O-allylmarcfortine A;

1-(2,4-dinitrobenzenesulfenyl)-14α-O-allylmarcfortine A;

24-propoxy-24,25-dihydro-14α-O-allylmarcfortine A;

1-(p-toluenesulfonyl)-14α-O-allylmarcfortine A;

1-acetyl-14α-O-allylmarcfortine A;

1-methyl-14α-O-allylmarcfortine A;

1-benzyl-14α-O-allylmarcfortine A;

1-dimethylcarbamoyl-14α-O-allylmarcfortine A;

1-methoxycarbonyl-14α-O-allylmarcfortine A;

14α-O-allylmarcfortine B;

24,25-dihydro-14α-O-allylmarcfortine B;

24-methoxy-24,25-dihydro-14α-O-allylmarcfortine B;

1-(p-toluenesulfonyl)-14α-O-allylmarcfortine B;

1-ethyl-14α-O-allylmarcfortine B;

1-benzyl-14α-O-allylmarcfortine B;

18a-ethyl-14α-O-allylmarcfortine B;

18a-benzyl-14α-O-allylmarcfortine B;

18a-methoxyethoxymethyl-14α-O-allylmarcfortine B;

18a-allyl-14α-O-allylmarcfortine B;

18a-propargyl-14α-O-allylmarcfortine B;

18a-ethyl-24-methoxy-24,25-dihydro-14α-O-allylmarcfortine B;

1,18a-bis-ethyl-14α-O-allylmarcfortine B;

1,18a-bis-benzyl-14α-O-allylmarcfortine B;
18a-ethyl-24-methoxy-14α-O-allylmarcfortine B;
1-(2,4-dinitrobenzene sulfonyl)-18a-ethyl-24-methoxy-24,25-dihydro-14α-O-allylmarcfortine B;
18a-ethyl-24,25 dihydro-14α-O-allylmarcfortine B;
24,25 dihydro-14α-O-allylmarcfortine C;
1-(p-bromobenzene sulfonyl)-14α-O-allylmarcfortine C;
1-propionyl-14α-O-allylmarcfortine C;
1-propyl-14α-O-allylmarcfortine C;
1-benzyl-14α-O-allylmarcfortine C;
18a-propyl-14α-O-allylmarcfortine C;
18a-benzyl-14α-O-allylmarcfortine C;
18a-methoxyethoxymethyl-14α-O-allylmarcfortine C;
18-allyl-14α-O-allylmarcfortine C;
18a-propargyl-14α-O-allylmarcfortine C;
1,18a-bis-propyl-14α-O-allylmarcfortine C;
1,18a-bis-benzyl-14α-O-allylmarcfortine C;
14α-O-allylmarcfortine C;
1-palmitoyl-14α-O-allylmarcfortine A;
1-(4-morpholinocarbonyl)-14α-O-allylmarcfortine A;
1-palmitoyl-14α-O-allylmarcfortine D;
1-(4-morpholinocarbonyl)-14α-O-allylmarcfortine D;
14α-O-allylmarcfortine D;
1-acetoxymethyl-14α-O-allylmarcfortine D;
1-diethoxyphosphoryl-14α-O-allylmarcfortine D;
1-dimethylsulfamoyl-14α-O-allylmarcfortine D;
1-cyclopropylcarbonyl-14α-O-allylmarcfortine D;
2-bicyclo[2.2.1]heptanoyl-14α-O-allylmarcfortine D;
1-(1-piperidinyl)thiocarbonyl-14α-O-allylmarcfortine D;
1-succinoyl-14α-O-allylmarcfortine D;
1-(4-morpholinosulfenyl)-14α-O-allylmarcfortine D;
1-(2,4-dinitrobenzenesulfenyl)-14α-O-allylmarcfortine D;
24-propoxy-24,25-dihydro-14α-O-allylmarcfortine D;
1-(p-toluenesulfonyl)-14α-O-allylmarcfortine D;
1-acetyl-14α-O-allylmarcfortine D;
1-methyl-14α-O-allylmarcfortine D;
1-benzyl-14α-O-allylmarcfortine D;
1-dimethylcarbamoyl-14α-O-allylmarcfortine D;
1-methoxycarbonyl-14α-O-allylmarcfortine D;
1-acetoxymethyl-14α-O-allyl-14β-methylmarcfortine A;
1-diethoxyphosphoryl-14α-O-allyl-14β-methylmarcfortine A;
1-dimethylsulfamoyl-14α-O-allyl-14β-methylmarcfortine A;
1-cyclopropylcarbonyl-14α-O-allyl-14β-methylmarcfortine A;
2-bicyclo[2.2.1]heptanoyl-14α-O-allyl-14β-methylmarcfortine A;
1-(1-piperidinyl)thiocarbonyl-14α-O-allyl-14β-methylmarcfortine A;
1-succinoyl-14α-O-allyl-14β-methylmarcfortine A;
1-(4-morpholinosulfenyl)-14α-O-allyl-14β-methylmarcfortine A;
1-(2,4-dinitrobenzenesulfenyl)-14α-O-allyl-14β-methylmarcfortine A;
24-propoxy-24,25-dihydro-14α-O-allyl-14β-methylmarcfortine A;
1-(p-toluenesulfonyl)-14α-O-allyl-14β-methylmarcfortine A;
1-acetyl-14α-O-allyl-14β-methylmarcfortine A;
1-methyl-14α-O-allyl-14β-methylmarcfortine A;
1-benzyl-14α-O-allyl-14β-methylmarcfortine A;
1-dimethylcarbamoyl-14α-O-allyl-14β-methylmarcfortine A;
1-methoxycarbonyl-14α-O-allyl-14β-methylmarcfortine A;
14α-O-allyl-14β-methylmarcfortine B;
24,25-dihydro-14α-O-allyl-14β-methylmarcfortine B;
24-methoxy-24,25-dihydro-14α-O-allyl-14β-methylmarcfortine B;
1-(p-toluenesulfonyl)-14α-O-allyl-14β-methylmarcfortine B;
1-ethyl-14α-O-allyl-14β-methylmarcfortine B;
1-benzyl-14α-O-allyl-14β-methylmarcfortine B;
18a-ethyl-14α-O-allyl-14β-methylmarcfortine B;
18a-benzyl-14α-O-allyl-14β-methylmarcfortine B;
18a-methoxyethoxymethyl-14α-O-allyl-14β-methylmarcfortine B;
18a-allyl-14α-O-allyl-14β-methylmarcfortine B;
18a-propargyl-14α-O-allyl-14β-methylmarcfortine B;
18a-ethyl-24-methoxy-24,25-dihydro-14α-O-allyl-14β-methylmarcfortine B;
1,18a-bis-ethyl-14α-O-allyl-14β-methylmarcfortine B;
1,18a-bis-benzyl-14α-O-allyl-14β-methylmarcfortine B;
18a-ethyl-24-methoxy-14α-O-allyl-14β-methylmarcfortine B;
1-(2,4-dinitrobenzene sulfonyl)-18a-ethyl-24-methoxy-24,25-dihydro-14α-O-allyl-14β-methylmarcfortine B;
18a-ethyl-24,25 dihydro-14α-O-allyl-14β-methylmarcfortine B;
24,25 dihydro-14α-O-allyl-14β-methylmarcfortine C;
1-(p-bromobenzene sulfonyl)-14α-O-allyl-14β-methylmarcfortine C;
1-propionyl-14α-O-allyl-14β-methylmarcfortine C;
1-propyl-14α-O-allyl-14β-methylmarcfortine C;
1-benzyl-14α-O-allyl-14β-methylmarcfortine C;
18a-propyl-14α-O-allyl-14β-methylmarcfortine C;
18a-benzyl-14α-O-allyl-14β-methylmarcfortine C;
18a-methoxyethoxymethyl-14α-O-allyl-14β-methylmarcfortine C;
18-allyl-14α-O-allyl-14β-methylmarcfortine C;
18a-propargyl-14α-O-allyl-14β-methylmarcfortine C;
1,18a-bis-propyl-14α-O-allyl-14β-methylmarcfortine C;
1,18-a-bis-benzyl-14α-O-allyl-14β-methylmarcfortine C;
14α-O-allyl-14β-methylmarcfortine C;
1-palmitoyl-14α-O-allyl-14β-methylmarcfortine A;
1-(4-morpholinocarbonyl)-14α-O-allyl-14β-methylmarcfortine A;
1-palmitoyl-14α-O-allyl-14β-methylmarcfortine D;
1-(4-morpholinocarbonyl)-14α-O-allyl-14β-methylmarcfortine D;
14α-O-allyl-14β-methylmarcfortine D;
1-acetoxymethyl-14α-O-allyl-14β-methylmarcfortine D;
1-diethoxyphosphoryl-14α-O-allyl-14β-methylmarcfortine D;
1-dimethylsulfamoyl-14α-O-allyl-14β-methylmarcfortine D;

1-cyclopropylcarbonyl-14α-O-allyl-14β-methylmarcfortine D;
2-bicyclo[2.2.1]heptanoyl-14α-O-allyl-14β-methylmarcfortine D;
1-(1-piperidinyl)thiocarbonyl-14α-O-allyl-14β-methylmarcfortine D;
1-succinoyl-14α-O-allyl-14β-methylmarcfortine D;
1(4-morpholinosulfenyl)-14α-O-allyl-14β-methylmarcfortine D;
1-(2,4-dinitrobenzenesulfenyl)-14α-O-allyl-14β-methylmarcfortine D;
24-propoxy-24,25-dihydro-14α-O-allyl-14β-methylmarcfortine D;
1-(p-toluenesulfonyl)-14α-O-allyl-14β-methylmarcfortine D;
1-acetyl-14α-O-allyl-14β-methylmarcfortine D;
1-methyl-14α-O-allyl-14β-methylmarcfortine D;
1-benzyl-14α-O-allyl-14β-methylmarcfortine D;
1-dimethylcarbamoyl-14α-O-allyl-14β-ethylmarcfortine D;
1-methoxycarbonyl-14α-O-allyl-14β-ethylmarcfortine D;
1-acetoxymethyl-14α-O-allyl-14β-ethylmarcfortine A;
1-diethoxyphosphoryl-14α-O-allyl-14β-ethylmarcfortine A;
1-dimethylsulfamoyl-14α-O-allyl-14β-ethylmarcfortine A;
1-cyclopropylcarbonyl-14α-O-allyl-14β-ethylmarcfortine A;
2-bicyclo[2.2.1]heptanoyl-14α-O-allyl-14β-ethylmarcfortine A;
1(1-piperidinyl)thiocarbonyl-14α-O-allyl-14β-ethylmarcfortine A;
1-succinoyl-14α-O-allyl-14β-ethylmarcfortine A;
1-(4-morpholinosulfenyl)-14α-O-allyl-14β-ethylmarcfortine A;
1-(2,4-dinitrobenzenesulfenyl)-14α-O-allyl-14β-ethylmarcfortine A;
24-propoxy-24,25-dihydro-14α-O-allyl-14β-ethylmarcfortine A;
1-(p-toluenesulfonyl)-14α-O-allyl-14β-ethylmarcfortine A;
1-acetyl-14α-O-allyl-14β-ethylmarcfortine A;
1-methyl-14α-O-allyl-14β-ethylmarcfortine A;
1-benzyl-14α-O-allyl-14β-ethylmarcfortine A;
1-dimethylcarbamoyl-14α-O-allyl-14β-ethylmarcfortine A;
1-methoxycarbonyl-14α-O-allyl-14β-ethylmarcfortine A;
14α-O-allyl-14β-ethylmarcfortine B;
24,25-dihydro-14α-O-allyl-14β-ethylmarcfortine B;
24-methoxy-24,25-dihydro-14α-O-allyl-14β-ethylmarcfortine B;
1-(p-toluenesulfonyl)-14α-O-allyl-14β-ethylmarcfortine B;
1-ethyl-14α-O-allyl-14β-ethylmarcfortine B;
1-benzyl-14α-O-allyl-14β-ethylmarcfortine B;
18a-ethyl-14α-O-allyl-14β-ethylmarcfortine B;
18a-benzyl-14α-O-allyl-14β-ethylmarcfortine B;
18a-methoxyethoxymethyl-14α-O-allyl-14β-ethylmarcfortine B;
18a-allyl-14α-O-allyl-14β-ethylmarcfortine B;
18a-propargyl-14α-O-allyl-14β-ethylmarcfortine B;
18a-ethyl-24-methoxy-24,25-dihydro-14α-O-allyl-14β-ethylmarcfortine B;
1,18a-bis-ethyl-14α-O-allyl-14β-ethylmarcfortine B;
1,18a-bis-benzyl-14α-O-allyl-14β-ethylmarcfortine B;
18a-ethyl-24-methoxy-14α-O-allyl-14β-ethylmarcfortine B;
1-(2,4-dinitrobenzene sulfonyl)-18a-ethyl-24-methoxy-24,25-dihydro-14α-O-allyl-14β-ethylmarcfortine B;
18a-ethyl-24,25 dihydro-14α-O-allyl-14β-ethylmarcfortine B;
24,25 dihydro-14α-O-allyl-14β-ethylmarcfortine C;
1-(p-bromobenzene sulfonyl)-14α-O-allyl-14β-ethylmarcfortine C;
1-propionyl-14α-O-allyl-14β-ethylmarcfortine C;
1-propyl-14α-O-allyl-14β-ethylmarcfortine C;
1-benzyl-14α-O-allyl-14β-ethylmarcfortine C;
18a-propyl-14α-O-allyl-14β-ethylmarcfortine C;
18a-benzyl-14α-O-allyl-14β-ethylmarcfortine C;
18a-methoxyethoxymethyl-14α-O-allyl-14β-ethylmarcfortine C;
18-allyl-14α-O-allyl-14β-ethylmarcfortine C;
18a-propargyl-14α-O-allyl-14β-ethylmarcfortine C;
1,18a-bis-propyl-14α-O-allyl-14β-ethylmarcfortine C;
1,18a-bis-benzyl-14α-O-allyl-14β-ethylmarcfortine C;
14α-O-allyl-14β-ethylmarcfortine C;
1-palmitoyl-14α-O-allyl-14β-ethylmarcfortine A;
1-(4-morpholinocarbonyl)-14α-O-allyl-14β-ethylmarcfortine A;
1-palmitoyl-14α-O-allyl-14β-ethylmarcfortine D;
1-(4-morpholinocarbonyl)-14α-O-allyl-14β-ethylmarcfortine D;
14α-O-allyl-14β-ethylmarcfortine D;
1-acetoxymethyl-14α-O-allyl-14β-ethylmarcfortine D;
1-diethoxyphosphoryl-14α-O-allyl-14β-ethylmarcfortine D;
1-dimethylsulfamoyl-14α-O-allyl-14β-ethylmarcfortine D;
1-cyclopropylcarbonyl-14α-O-allyl-14β-ethylmarcfortine D;
2-bicyclo[2.2.1]heptanoyl-14α-O-allyl-14β-ethylmarcfortine D;
1-(1-piperidinyl)thiocarbonyl-14α-O-allyl-14β-ethylmarcfortine D;
1-succinoyl-14α-O-allyl-14β-ethylmarcfortine D;
1-(4-morpholinosulfenyl)-14α-O-allyl-14β-ethylmarcfortine D;
1-(2,4-dinitrobenzenesulfenyl)-14α-O-allyl-14β-ethylmarcfortine D;
24-propoxy-24,25-dihydro-14α-O-allyl-14β-ethylmarcfortine D;
1-(p-toluenesulfonyl)-14α-O-allyl-14β-ethylmarcfortine D;
1-acetyl-14α-O-allyl-14β-ethylmarcfortine D;
1-methyl-14α-O-allyl-14β-ethylmarcfortine D;
1-benzyl-14α-O-allyl-14β-ethylmarcfortine D;
1-dimethylcarbamoyl-14α-O-allyl-14β-ethylmarcfortine D;

1-methoxycarbonyl-14α-O-allyl-14β-ethylmarcfortine D;

14α-hydroxy-14β-methyl-15α-methylmarcfortine A;

1-acetoxymethyl-14α-hydroxy-14β-methyl-15α-methylmarcfortine A;

1-diethoxyphosphoryl-14α-hydroxy-14β-methyl-15α-methylxymarcfortine A;

1-dimethylsulfamoyl-14α-hydroxy-14β-methyl-15α-methylmarcfortine A;

1-cyclopropylcarbonyl-14α-hydroxy-14β-methyl-15α-methylmarcfortine A;

2-bicyclo[2.2.1]heptanoyl-14α-hydroxy-14β-methyl-15α-methylmarcfortine A;

1-(1-piperidinyl)thiocarbonyl-14α-hydroxy-14β-methyl-15α-methylmarcfortine A;

1-succinoyl-14α-hydroxy-14β-methyl-15α-methylmarcfortine A;

1-(4-morpholinosulfenyl)-14α-hydroxy-14β-methyl-15α-methylmarcfortine A;

1-(2,4-dinitrobenzenesulfenyl)-14α-hydroxy-14β-methyl-15α-methylmarcfortine A;

24-propoxy-24,25-dihydro-14α-hydroxy-14β-methyl-15α-methylmarcfortine A;

1-(p-toluenesulfonyl)-14α-hydroxy-14β-methyl-15α-methylmarcfortine A;

1-acetyl-14α-hydroxy-14β-methyl-15α-methylmarcfortine A;

1-methyl-14α-hydroxy-14β-methyl-15α-methylmarcfortine A;

1-benzyl-14α-hydroxy-14β-methyl-15α-methylmarcfortine A;

1-dimethylcarbamoyl-14α-hydroxy-14β-methyl-15α-methylmarcfortine A;

1-methoxycarbonyl-14α-hydroxy-14β-methyl-15α-methylmarcfortine A;

14α-hydroxy-14β-methyl-15α-methylmarcfortine B;

24,25-dihydro-14α-hydroxy-14β-methyl-15α-methylmarcfortine B;

24-methoxy-24,25-dihydro-14α-hydroxy-14β-methyl-15α-methylmarcfortine B;

1-(p-toluenesulfonyl)-14α-hydroxy-14β-methyl-15α-methylmarcfortine B;

1-ethyl-14α-hydroxy-14β-methyl-15α-methylmarcfortine B;

1-benzyl-14α-hydroxy-14β-methyl-15α-methylmarcfortine B;

18a-ethyl-14α-hydroxy-14β-methyl-15α-methylmarcfortine B;

18a-benzyl-14α-hydroxy-14β-methyl-15α-methylmarcfortine B;

18a-methoxyethoxymethyl-14α-hydroxy-14β-methyl-15α-methylmarcfortine B;

18a-allyl-14α-hydroxy-14β-methyl-15α-methylmarcfortine B;

18a-propargyl-14α-hydroxy-14β-methyl-15α-methylmarcfortine B;

18a-ethyl-24-methoxy-24,25-dihydro-14α-hydroxy-14β-methyl-15α-methylmarcfortine B;

1,18a-bis-ethyl-14α-hydroxy-14β-methyl-15α-methylmarcfortine B;

1,18a-bis-benzyl-14α-hydroxy-14β-methyl-15α-methylmarcfortine B;

18a-ethyl-24-methoxy-14α-hydroxy-14β-methyl-15α-methylmarcfortine B;

1-(2,4-dinitrobenzene sulfonyl)-18a-ethyl-24-methoxy-24,25-dihydro-14α-hydroxymarcfortine B;

18a-ethyl-24,25 dihydro-14α-hydroxy-14β-methyl-15α-methylmarcfortine B;

24,25 dihydro-14α-hydroxy-14β-methyl-15α-methylmarcfortine C;

1-(p-bromobenzene sulfonyl)-14α-hydroxy-14β-methyl-15α-methylmarcfortine C;

1-propionyl-14α-hydroxy-14β-methyl-15α-methylmarcfortine C;

1-propyl-14α-hydroxy-14β-methyl-15α-methylmarcfortine C;

1-benzyl-14α-hydroxy-14β-methyl-15α-methylmarcfortine C;

18a-propyl-14α-hydroxy-14β-methyl-15α-methylmarcfortine C;

18a-benzyl-14α-hydroxy-14β-methyl-15α-methylmarcfortine C;

18a-methoxyethoxymethyl-14α-hydroxy-14β-methyl-15α-methylmarcfortine C;

18-allyl-14α-hydroxy-14β-methyl-15α-methylmarcfortine C;

18a-propargyl-14α-hydroxy-14β-methyl-15α-methylmarcfortine C;

1,18a-bis-propyl-14α-hydroxy-14β-methyl-15α-methylmarcfortine C;

1,18a-bis-benzyl-14α-hydroxy-14β-methyl-15α-methylmarcfortine C;

14α-hydroxy-14β-methyl-15α-methylmarcfortine C;

1-(4-carbethoxy-1,3-thiazolidinin-3-yl)carbonyl-14α-hydroxy-14β-methyl-15α-methylmarcfortine A;

1-palmitoyl-14α-hydroxy-14β-methyl-15α-methylmarcfortine A;

1-(4-morpholinocarbonyl)-14α-hydroxy-14β-methyl-15α-methylmarcfortine A;

1-palmitoyl-14α-hydroxy-14β-methyl-15α-methylmarcfortine D;

1-(4-morpholinocarbonyl)-14α-hydroxy-14β-methyl-15α-methylmarcfortine D;

14α-hydroxy-14β-methyl-15α-methylmarcfortine D;

1-acetoxymethyl-14α-hydroxy-14β-methyl-15α-methylmarcfortine D;

1-diethoxyphosphoryl-14α-hydroxy-14β-methyl-15α-methylmarcfortine D;

1-dimethylsulfamoyl-14α-hydroxy-14β-methyl-15α-methylmarcfortine D;

1-cyclopropylcarbonyl-14α-hydroxy-14β-methyl-15α-methylmarcfortine D;

2-bicyclo[2.2.1]heptanoyl-14α-hydroxy-14β-methyl-15α-methylmarcfortine D;

1-(1-piperidinyl)thiocarbonyl-14α-hydroxy-14β-methyl-15α-methylmarcfortine D;

1-succinoyl-14α-hydroxy-14β-methyl-15α-methylmarcfortine D;

1-(4-morpholinosulfenyl)-14α-hydroxy-14β-methyl-15α-methylmarcfortine D;

1-(2,4-dinitrobenzenesulfenyl)-14α-hydroxy-14β-methyl-15α-methylmarcfortine D;

24-propoxy-24,25-dihydro-14α-hydroxy-14β-methyl-15α-methylmarcfortine D;

1-(p-toluenesulfonyl)-14α-hydroxy-14β-methyl-15α-methylmarcfortine D;
1-acetyl-14α-hydroxy-14β-methyl-15α-methylmarcfortine D;
1-methyl-14α-hydroxy-14β-methyl-15α-methylmarcfortine D;
1-benzyl-14α-hydroxy-14β-methyl-15α-methylmarcfortine D;
1-dimethylcarbamoyl-14α-hydroxy-14β-methyl-15α-methylmarcfortine D;
1-methoxycarbonyl-14α-hydroxy-14β-methyl-15α-methylmarcfortine D;
-14α-hydroxy-15α-methylmarcfortine A;
1-acetoxymethyl-14α-hydroxy-15α-methylmarcfortine A;
1-diethoxyphosphoryl-14α-hydroxy-15α-methylmarcfortine A;
1-dimethylsulfamoyl-14α-hydroxy-15α-methylmarcfortine A;
1-cyclopropylcarbonyl-14α-hydroxy-15α-methylmarcfortine A;
2-bicyclo[2.2.1]heptanoyl-14α-hydroxy-15α-methylmarcfortine A;
1-(1-piperidinyl)thiocarbonyl-14α-hydroxy-15α-methylmarcfortine A;
1-succinoyl-14α-hydroxy-15α-methylmarcfortine A;
1-(4-morpholinosulfenyl)-14α-hydroxy-15α-methylmarcfortine A;
1-(2,4-dinitrobenzenesulfenyl)-14α-hydroxy-15α-methylmarcfortine A;
24-propoxy-24,25-dihydro-14α-hydroxy-15α-methylmarcfortine A;
1-(p-toluenesulfonyl)-14α-hydroxy-15α-methylmarcfortine A;
1-acetyl-14α-hydroxy-15α-methylmarcfortine A;
1-methyl-14α-hydroxy-15α-methylmarcfortine A;
1-benzyl-14α-hydroxy-15α-methylmarcfortine A;
1-dimethylcarbamoyl-14α-hydroxy-15α-methylmarcfortine A;
1-methoxycarbonyl-14α-hydroxy-15α-methylmarcfortine A;
14α-hydroxy-15α-methylmarcfortine B;
24,25-dihydro-14α-hydroxy-15α-methylmarcfortine B;
24-methoxy-24,25-dihydro-14α-hydroxy-15α-methylmarcfortine B;
1-(p-toluenesulfonyl)-14α-hydroxy-15α-methylmarcfortine B;
1-ethyl-14α-hydroxy-15α-methylmarcfortine B;
1-benzyl-14α-hydroxy-15α-methylmarcfortine B;
18a-ethyl-14α-hydroxy-15α-methylmarcfortine B;
18a-benzyl-14α-hydroxy-15α-methylmarcfortine B;
18a-methoxyethoxymethyl-14α-hydroxy-15α-methylmarcfortine B;
18a-allyl-14α-hydroxy-15α-methylmarcfortine B;
18a-propargyl-14α-hydroxy-15α-methylmarcfortine B;
18a-ethyl-24-methoxy-24,25-dihydro-14α-hydroxy-15α-methylmarcfortine B;
1,18a-bis-ethyl-14α-hydroxy-15α-methylmarcfortine B;
1,18a-bis-benzyl-14α-hydroxy-15α-methylmarcfortine B;
18a-ethyl-24-methoxy-14α-hydroxy-15α-methylmarcfortine B;
1-(2,4-dinitrobenzene sulfonyl)-18a-ethyl-24-methoxy-24,25-dihydro-14α-hydroxymarcfortine B;
18a-ethyl-24,25 dihydro-14α-hydroxy-15α-methylmarcfortine B;
24,25 dihydro-14α-hydroxy-15α-methylmarcfortine C;
1-(p-bromobenzene sulfonyl)-14α-hydroxy-15α-methylmarcfortine C;
1-propionyl-14α-hydroxy-15α-methylmarcfortine C;
1-propyl-14α-hydroxy-15α-methylmarcfortine C;
1-benzyl-14α-hydroxy-15α-methylmarcfortine C;
18a-propyl-14α-hydroxy-15α-methylmarcfortine C;
18a-benzyl-14α-hydroxy-15α-methylmarcfortine C;
18a-methoxyethoxymethyl-14α-hydroxy-15α-methylmarcfortine C;
18-allyl-14α-hydroxy-15α-methylmarcfortine C;
18a-propargyl-14α-hydroxy-15α-methylmarcfortine C;
1,18a-bis-propyl-14α-hydroxy-15α-methylmarcfortine C;
1,18a-bis-benzyl-14α-hydroxy-15α-methylmarcfortine C;
14α-hydroxy-15α-methylmarcfortine C;
1(4-carbethoxy-1,3-thiazolidinin-3-yl)carbonyl-14α-hydroxy-15α-methylmarcfortine A;
1-palmitoyl-14α-hydroxy-15α-methylmarcfortine A;
1-(4-morpholinocarbonyl)-14α-hydroxy-15α-methylmarcfortine A;
1-palmitoyl-14α-hydroxy-15α-methylmarcfortine D;
1-(4-morpholinocarbonyl)-14α-hydroxy-15α-methylmarcfortine D;
14α-hydroxy-15α-methylmarcfortine D;
1-acetoxymethyl-14α-hydroxy-15α-methylmarcfortine D;
1-diethoxyphosphoryl-14α-hydroxy-15α-methylmarcfortine D;
1-dimethylsulfamoyl-14α-hydroxy-15α-methylmarcfortine D;
1-cyclopropylcarbonyl-14α-hydroxy-15α-methylmarcfortine D;
2-bicyclo[2.2.1]heptanoyl-14α-hydroxy-15α-methylmarcfortine D;
1-(1-piperidinyl)thiocarbonyl-14α-hydroxy-15α-methylmarcfortine D;
1-succinoyl-14α-hydroxy-15α-methylmarcfortine D;
1-(4-morpholinosulfenyl)-14α-hydroxy-15α-methylmarcfortine D;
1-(2,4-dinitrobenzenesulfenyl)-14α-hydroxy-15α-methylmarcfortine D;
24-propoxy-24,25-dihydro-14α-hydroxy-15α-methylmarcfortine D;
1-(p-toluenesulfonyl)-14α-hydroxy-15α-methylmarcfortine D;
1-acetyl-14α-hydroxy-15α-methylmarcfortine D;
1-methyl-14α-hydroxy-15α-methylmarcfortine D;
1-benzyl-14α-hydroxy-15α-methylmarcfortine D;
1-dimethylcarbamoyl-14α-hydroxy-15α-methylmarcfortine D; and
1-methoxycarbonyl-14α-hydroxy-15α-methylmarcfortine D.

The novel compounds of this invention are prepared by the following chemical reactions which, as examples, are applied to the preparation of 14α-hydroxymarcfortine A (Formula 10, Chart A), 14α-hydroxy-14β-methylmarcfortine A (Formula 15, Chart C), 14β-hydroxymarcfortine A (Formula 17, Chart D), 14α-hydroxymarcfortine A N-oxide (Formula 18, Chart D), 14α-hydroxy-14β-ethylmarcfortine A (Formula 19, Chart D), 14β-methylmarcfortine A 14α-hydroxy-14β-methyl-14α-methylmarcfortine A, 14α-hydroxy-15α-methylmarcfortine A, and their precursors (Chart A through G).

The novel compounds of this invention are prepared by the following procedures: It has been found, unexpectedly, that treatment of the Marcfortines A, B, C and D, or suitably substituted C-24, C-25, N-1 and N-18a derivatives thereof, with cyanogen iodide provides a means of producing the compounds of the present invention as illustrated by Charts A.

Another aspect of the present invention are the novel intermediates prepared in accordance with Chart A through G, including:

16-iodo-17-cyanomarcfortine A;
1-acetoxymethyl-16-iodo-17-cyanomarcfortine A;
1-diethoxyphosphoryl-16-iodo-17-cyanomarcfortine A;
1-dimethylsulfamoyl-16-iodo-17-cyanomarcfortine A;
1-cyclopropylcarbonyl-16-iodo-17-cyanomarcfortine A;
2-bicyclo[2.2.1]heptanoyl-16-iodo-17-cyanomarcfortine A;
1-(1-piperidinyl)thiocarbonyl-16-iodo-17-cyanomarcfortine A;
1-succinoyl-16-iodo-17-cyanomarcfortine A;
1-(4-morpholinosulfenyl)-16-iodo-17-cyanomarcfortine A;
1-(2,4-dinitrobenzenesulfenyl)-16-iodo-17-cyanomarcfortine A;
24-propoxy-24,25-dihydro-16-iodo-17-cyanomarcfortine A;
1-(p-toluenesulfonyl)-16-iodo-17-cyanomarcfortine A;
1-acetyl-16-iodo-17-cyanomarcfortine A;
1-methyl-16-iodo-17-cyanomarcfortine A;
1-benzyl-16-iodo-17-cyanomarcfortine A;
1-dimethylcarbamoyl-16-iodo-17-cyanomarcfortine A;
1-methoxycarbonyl-16-iodo-17-cyanomarcfortine A;
16-iodo-17-cyanomarcfortine B;
24,25-dihydro-16-iodo-17-cyanomarcfortine B;
24-methoxy-24,25-dihydro-16-iodo-17-cyanomarcfortine B;
1-(p-toluenesulfonyl)-16-iodo-17-cyanomarcfortine B;
1-ethyl-16-iodo-17-cyanomarcfortine B;
1-benzyl-16-iodo-17-cyanomarcfortine B;
18a-ethyl-16-iodo-17-cyanomarcfortine B;
18a-benzyl-16-iodo-17-cyanomarcfortine B;
18a-methoxyethoxymethyl-16-iodo-17-cyanomarcfortine B;
18a-allyl-16-iodo-17-cyanomarcfortine B;
18a-propargyl-16-iodo-17-cyanomarcfortine B;
18a-ethyl-24-methoxy-24,25-dihydro-16-iodo-17-cyanomarcfortine B;
1,18a-bis-ethyl-16-iodo-17-cyanomarcfortine B;
1,18a-bis-benzyl-16-iodo-17-cyanomarcfortine B;
18a-ethyl-24-methoxy-16-iodo-17-cyanomarcfortine B;
1-(2,4-dinitrobenzene sulfonyl)-18a-ethyl-24-methoxy-24,25-dihydro-16-iodo-17-cyanomarcfortine B;
18a-ethyl-24,25 dihydro-16-iodo-17-cyanomarcfortine B;
24,25 dihydro-16-iodo-17-cyanomarcfortine C;
1-(p-bromobenzene sulfonyl)-16-iodo-17-cyanomarcfortine C;
1-propionyl-16-iodo-17-cyanomarcfortine C;
1-propyl-16-iodo-17-cyanomarcfortine C;
1-benzyl-16-iodo-17-cyanomarcfortine C;
18a-propyl-16-iodo-17-cyanomarcfortine C;
18a-benzyl-16-iodo-17-cyanomarcfortine C;
18a-methoxyethoxymethyl-16-iodo-17-cyanomarcfortine C;
18-allyl-16-iodo-17-cyanomarcfortine C;
18a-propargyl-16-iodo-17-cyanomarcfortine C;
1,18a-bis-propyl-16-iodo-17-cyanomarcfortine C;
1,18a-bis-benzyl-16-iodo-17-cyanomarcfortine C;
16-iodo-17-cyanomarcfortine C;
1-(4-carbethoxy-1,3-thiazolidinin-3-yl)carbonyl-16-iodo-17-cyanomarcfortine A;
1-palmitoyl-16-iodo-17-cyanomarcfortine A;
1-(4-morpholinocarbonyl)-16-iodo-17-cyanomarcfortine A;
1-palmitoyl-16-iodo-17-cyanomarcfortine D;
1-(4-morpholinocarbonyl)-16-iodo-17-cyanomarcfortine D;
16-iodo-17-cyanomarcfortine D;
1-acetoxymethyl-16-iodo-17-cyanomarcfortine D;
1-diethoxyphosphoryl-16-iodo-17-cyanomarcfortine D;
1-dimethylsulfamoyl-16-iodo-17-cyanomarcfortine D;
1-cyclopropylcarbonyl-16-iodo-17-cyanomarcfortine D;
2-bicyclo[2.2.1]heptanoyl-16-iodo-17-cyanomarcfortine D;
1-(1-piperidinyl)thiocarbonyl-16-iodo-17-cyanomarcfortine D;
1-succinoyl-16-iodo-17-cyanomarcfortine D;
1-(4-morpholinosulfenyl)-16-iodo-17-cyanomarcfortine D;
1-(2,4-dinitrobenzenesulfenyl)-16-iodo-17-cyanomarcfortine D;
24-propoxy-24,25-dihydro-16-iodo-17-cyanomarcfortine D;
1-(p-toluenesulfonyl)-16-iodo-17-cyanomarcfortine D;
1-acetyl-16-iodo-17-cyanomarcfortine D;
1-methyl-16-iodo-17-cyanomarcfortine D;
1-benzyl-16-iodo-17-cyanomarcfortine D;
1-dimethylcarbamoyl-16-iodo-17-cyanomarcfortine D;
1-methoxycarbonyl-16-iodo-17-cyanomarcfortine D;
16,17-dehydro-17-cyanomarcfortine A;
1-acetoxymethyl-16,17-dehydro-17-cyanomarcfortine A;
1-diethoxyphosphoryl-16,17-dehydro-17-cyanomarcfortine A;
1-dimethylsulfamoyl-16,17-dehydro-17-cyanomarcfortine A;
1-cyclopropylcarbonyl-16,17-dehydro-17-cyanomarcfortine A;
2-bicyclo[2.2.1]heptanoyl-16,17-dehydro-17-cyanomarcfortine A;
1-(1-piperidinyl)thiocarbonyl-16,17-dehydro-17-cyanomarcfortine A;

1-succinoyl-16,17-dehydro-17-cyanomarcfortine A;
1-(4-morpholinosulfenyl)-16,17-dehydro-17-cyanomarcfortine A;
1-(2,4-dinitrobenzenesulfenyl)-16,17-dehydro-17-cyanomarcfortine A;
24-propoxy-24,25-dihydro-16,17-dehydro-17-cyanomarcfortine A;
1-(p-toluenesulfonyl)-16,17-dehydro-17-cyanomarcfortine A;
1-acetyl-16,17-dehydro-17-cyanomarcfortine A;
1-methyl-16,17-dehydro-17-cyanomarcfortine A;
1-benzyl-16,17-dehydro-17-cyanomarcfortine A;
1-dimethylcarbamoyl-16,17-dehydro-17-cyanomarcfortine A;
1-methoxycarbonyl-16,17-dehydro-17-cyanomarcfortine A;
16,17-dehydro-17-cyanomarcfortine B;
24,25-dihydro-16,17-dehydro-17-cyanomarcfortine B;
24-methoxy-24,25-dihydro-16,17-dehydro-17-cyanomarcfortine B;
1-(p-toluenesulfonyl)-16,17-dehydro-17-cyanomarcfortine B;
1-ethyl-16,17-dehydro-17-cyanomarcfortine B;
1-benzyl-16,17-dehydro-17-cyanomarcfortine B;
18a-ethyl-16,17-dehydro-17-cyanomarcfortine B;
18a-benzyl-16,17-dehydro-17-cyanomarcfortine B;
18a-methoxyethoxymethyl-16,17-dehydro-17-cyanomarcfortine B;
18a-allyl-16,17-dehydro-17-cyanomarcfortine B;
18a-propargyl-16,17-dehydro-17-cyanomarcfortine B;
18a-ethyl-24-methoxy-24,25-dihydro-16,17-dehydro-17-cyanomarcfortine B;
1,18a-bis-ethyl-16,17-dehydro-17-cyanomarcfortine B;
1,18a-bis-benzyl-16,17-dehydro-17-cyanomarcfortine B;
18a-ethyl-24-methoxy-16,17-dehydro-17-cyanomarcfortine B;
1-(2,4-dinitrobenzene sulfonyl)-18a-ethyl-24-methoxy-24,25-dihydro-16,17-dehydro-17-cyanomarcfortine B;
18a-ethyl-24,25 dihydro-16,17-dehydro-17-cyanomarcfortine B;
24,25 dihydro-16,17-dehydro-17-cyanomarcfortine C;
1-(p-bromobenzene sulfonyl)-16,17-dehydro-17-cyanomarcfortine C;
1-propionyl-16,17-dehydro-17-cyanomarcfortine C;
1-propyl-16,17-dehydro-17-cyanomarcfortine C;
1-benzyl-16,17-dehydro-17-cyanomarcfortine C;
18a-propyl-16,17-dehydro-17-cyanomarcfortine C;
18a-benzyl-16,17-dehydro-17-cyanomarcfortine C;
18a-methoxyethoxymethyl-16,17-dehydro-17-cyanomarcfortine C;
18-allyl-16,17-dehydro-17-cyanomarcfortine C;
18a-propargyl-16,17-dehydro-17-cyanomarcfortine C;
1,18a-bis-propyl-16,17-dehydro-17-cyanomarcfortine C;
1,18a-bis-benzyl-16,17-dehydro-17-cyanomarcfortine C;
16,17-dehydro-17-cyanomarcfortine C;
1-(4-carbethoxy-1,3-thiazolidinin-3-yl)carbonyl-16,17-dehydro-17-cyanomarcfortine A;
1-palmitoyl-16,17-dehydro-17-cyanomarcfortine A;
1-(4-morpholinocarbonyl)-16,17-dehydro-17-cyanomarcfortine A;
1-palmitoyl-16,17-dehydro-17-cyanomarcfortine D;
1-(4-morpholinocarbonyl)-16,17-dehydro-17-cyanomarcfortine D;
16,17-dehydro-17-cyanomarcfortine D;
1-acetoxymethyl-16,17-dehydro-17-cyanomarcfortine D;
1-diethoxyphosphoryl-16,17-dehydro-17-cyanomarcfortine D;
1-dimethylsulfamoyl-16,17-dehydro-17-cyanomarcfortine D;
1-cyclopropylcarbonyl-16,17-dehydro-17-cyanomarcfortine D;
2-bicyclo[2.2.1]heptanoyl-16,17-dehydro-17-cyanomarcfortine D;
1-(1-piperidinyl)thiocarbonyl-16,17-dehydro-17-cyanomarcfortine D;
1-succinoyl-16,17-dehydro-17-cyanomarcfortine D;
1-(4-morpholinosulfenyl)-16,17-dehydro-17-cyanomarcfortine D;

1-(2,4-dinitrobenzenesulfenyl)-16,17-dehydro-17-cyanomarcfortine D;

24-propoxy-24,25-dihydro-16,17-dehydro-17-cyanomarcfortine D;

1-(p-toluenesulfonyl)-16,17-dehydro-17-cyanomarcfortine D;

1-acetyl-16,17-dehydro-17-cyanomarcfortine D;

1-methyl-16,17-dehydro-17-cyanomarcfortine D;

1-benzyl-16,17-dehydro-17-cyanomarcfortine D;

1-dimethylcarbamoyl-16,17-dehydro-17-cyanomarcfortine D;

1-methoxycarbonyl-16,17-dehydro-17-cyanomarcfortine D;

17-ketomarcfortine A;

1-acetoxymethyl-17-ketomarcfortine A;

1-diethoxyphosphoryl-17-ketoxymarcfortine A;

1-dimethylsulfamoyl-17-ketomarcfortine A;

1-cyclopropylcarbonyl-17-ketomarcfortine A;

2-bicyclo[2.2.1]heptanoyl-17-ketomarcfortine A;

1-(1-piperidinyl)thiocarbonyl-17-ketomarcfortine A;

1-succinoyl-17-ketomarcfortine A;

1-(4-morpholinosulfenyl)-17-ketomarcfortine A;

1-(2,4-dinitrobenzenesulfenyl)-17-ketomarcfortine A;

24-propoxy-24,25-dihydro-17-ketomarcfortine A;

1-(p-toluenesulfonyl)-17-ketomarcfortine A;

1-acetyl-17-ketomarcfortine A;

1-methyl-17-ketomarcfortine A;

1-benzyl-17-ketomarcfortine A;

1-dimethylcarbamoyl-17-ketomarcfortine A;

1-methoxycarbonyl-17-ketomarcfortine A;

17-ketomarcfortine B;

24,25-dihydro-17-ketomarcfortine B;

24-methoxy-24,25-dihydro-17-ketomarcfortine B;

1-(p-toluenesulfonyl)-17-ketomarcfortine B;

1-ethyl-17-ketomarcfortine B;

1-benzyl-17-ketomarcfortine B;

18a-ethyl-17-ketomarcfortine B;

18a-benzyl-17-ketomarcfortine B;

18a-methoxyethoxymethyl-17-ketomarcfortine B;

18a-allyl-17-ketomarcfortine B;

18a-propargyl-17-ketomarcfortine B;
18a-ethyl-24-methoxy-24,25-dihydro-17-ketomarcfortine B;
1,18a-bis-ethyl-17-ketomarcfortine B;
1,18a-bis-benzyl-17-ketomarcfortine B;
18a-ethyl-24-methoxy-17-ketomarcfortine B;
1-(2,4-dinitrobenzene sulfonyl)-18a-ethyl-24-methoxy-24,25-dihydro-14α-hydroxymarcfortine B;
18a-ethyl-24,25 dihydro-17-ketomarcfortine B;
24,25 dihydro-17-ketomarcfortine C;
1-(p-bromobenzene sulfonyl)-17-ketomarcfortine C;
1-propionyl-17-ketomarcfortine C;
1-propyl-17-ketomarcfortine C;
1-benzyl-17-ketomarcfortine C;
18a-propyl-17-ketomarcfortine C;
18a-benzyl-17-ketomarcfortine C;
18a-methoxyethoxymethyl-17-ketomarcfortine C;
18-allyl-17-ketomarcfortine C;
18a-propargyl-17-ketomarcfortine C;
1,18a-bis-propyl-17-ketomarcfortine C;
1,18a-bis-benzyJ-17-ketomarcfortine C;
17-ketomarcfortine C;
1-(4-carbethoxy-1,3-thiazolidinin-3-yl)carbonyl-17-ketomarcfortine A;
1-palmitoyl-17-ketomarcfortine A;
1-(4-morpholinocarbonyl)-17-ketomarcfortine A;
1-palmitoyl-17-ketomarcfortine D;
1-(4-morpholinocarbonyl)-17-ketomarcfortine D;
17-ketodroxymarcfortine D;
1-acetoxymethyl-17-ketomarcfortine D;
1-diethoxyphosphoryl-17-ketomarcfortine D;
1-dimethylsulfamoyl-17-ketomarcfortine D;
1-cyclopropylcarbonyl-17-ketomarcfortine D;
2-bicyclo[2.2.1]heptanoyl-17-ketomarcfortine D;
1-(1-piperidinyl)thiocarbonyl-17-ketomarcfortine D;
1-succinoyl-17-ketomarcfortine D;
1-(4-morpholinosulfenyl)-17-ketomarcfortine D;
1-(2,4-dinitrobenzenesulfenyl)-17-ketomarcfortine D;
24-propoxy-24,25-dihydro-17-ketomarcfortine D;
1-(p-toluenesulfonyl)-17-ketomarcfortine D;
1-acetyl-17-ketomarcfortine D;
1-methyl-17-ketomarcfortine D;
1-benzyl-17-ketomarcfortine D;
1-dimethylcarbamoyl-17-ketomarcfortine D;
1-methoxycarbonyl-17-ketomarcfortine D;
15,16-dehydro-17-ketomarcfortine A;
1-acetoxymethyl-15,16-dehydro-17-ketomarcfortine A;
1-diethoxyphosphoryl-15,16-dehydro-17-ketoxymarcfortine A;
1-dimethylsulfamoyl-15,16-dehydro-17-ketomarcfortine A;
1-cyclopropylcarbonyl-15,16-dehydro-17-ketomarcfortine A;
2-bicyclo[2.2.1]heptanoyl-15,16-dehydro-17-ketomarcfortine A;
1-(1-piperidinyl)thiocarbonyl-15,16-dehydro-17-ketomarcfortine A;
1-succinoyl-15,16-dehydro-17-ketomarcfortine A;

1-(4-morpholinosulfenyl)-15,16-dehydro-17-ketomarcfortine A;
1-(2,4-dinitrobenzenesulfenyl)-15,16-dehydro-17-ketomarcfortine A;
24propoxy-24,25-dihydro-15,16-dehydro-17-ketomarcfortine A;
1-(p-toluenesulfonyl)-15,16-dehydro-17-ketomarcfortine A;
1-acetyl-15,16-dehydro-17-ketomarcfortine A;
1-methyl-15,16-dehydro-17-ketomarcfortine A;
1-benzyl-15,16-dehydro-17-ketomarcfortine A;
1-dimethylcarbamoyl-15,16-dehydro-17-ketomarcfortine A;
1-methoxycarbonyl-15,16-dehydro-17-ketomarcfortine A;
15,16-dehydro-17-ketomarcfortine B;
24,25-dihydro-15,16-dehydro-17-ketomarcfortine B;
24-methoxy-24,25-dihydro-15,16-dehydro-17-ketomarcfortine B;
1-(p-toluenesulfonyl)-15,16-dehydro-17-ketomarcfortine B;
1-ethyl-15,16-dehydro-17-ketomarcfortine B;
1-benzyl-15,16-dehydro-17-ketomarcfortine B;
18a-ethyl-15,16-dehydro-17-ketomarcfortine B;
18a-benzyl-15,16-dehydro-17-ketomarcfortine B;
18a-methoxyethoxymethyl-15,16-dehydro-17-ketomarcfortine B;
18a-allyl-15,16-dehydro-17-ketomarcfortine B;
18a-propargyl-15,16-dehydro-17-ketomarcfortine B;
18a-ethyl-24-methoxy-24,25-dihydro-15,16-dehydro-17-ketomarcfortine B;
1,18a-bis-ethyl-15,16-dehydro-17-ketomarcfortine B;
1,18a-bis-benzyl-15,16-dehydro-17-ketomarcfortine B;
18a-ethyl-24-methoxy-15,16-dehydro-17-ketomarcfortine B;
1-(2,4-dinitrobenzene sulfonyl)-18a-ethyl-24-methoxy-24,25-dihydro-14α-hydroxymarcfortine B;
18a-ethyl-24,25 dihydro-15,16-dehydro-17-ketomarcfortine B;
24,25 dihydro-15,16-dehydro-17-ketomarcfortine C;
1-(p-bromobenzene sulfonyl)-15,16-dehydro-17-ketomarcfortine C;
1-propionyl-15,16-dehydro-17-ketomarcfortine C;
1-propyl-15,16-dehydro-17-ketomarcfortine C;
1-benzyl-15,16-dehydro-17-ketomarcfortine C;
18a-propyl-15,16-dehydro-17-ketomarcfortine C;
18a-benzyl-15,16-dehydro-17-ketomarcfortine C;
18a-methoxyethoxymethyl-15,16-dehydro-17-ketomarcfortine C;
18-allyl-15,16-dehydro-17-ketomarcfortine C;
18a-propargyl-15,16-dehydro-17-ketomarcfortine C;
1,18a-bis-propyl-15,16-dehydro-17-ketomarcfortine C;
1,18a-bis-benzyl-15,16-dehydro-17-ketomarcfortine C;
15,16-dehydro-17-ketomarcfortine C;
1-(4carbethoxy-1,3-thiazolidinin-3-yl)carbonyl-15,16-dehydro-17-ketomarcfortine A;
1-palmitoyl-15,16-dehydro-17-ketomarcfortine A;
1-(4-morpholinocarbonyl)-15,16-dehydro-17-ketomarcfortine A;

1-palmitoyl-15,16-dehydro-17-ketomarcfortine D;

1-(4-morpholinocarbonyl)-15,16-dehydro-17-ketomarcfortine D;

15,16-dehydro-17-ketomarcfortine D;

1-acetoxymethyl-15,16-dehydro-17-ketomarcfortine D;

1-diethoxyphosphoryl-15,16-dehydro-17-ketomarcfortine D;

1-dimethylsulfamoyl-15,16-dehydro-17-ketomarcfortine D;

1-cyclopropylcarbonyl-15,16-dehydro-17-ketomarcfortine D;

2-bicyclo[2.2.1]heptanoyl-15,16-dehydro-17-ketomarcfortine D;

1-(1-piperidinyl)thiocarbonyl-15,16-dehydro-17-ketomarcfortine D;

1-succinoyl-15,16-dehydro-17-ketomarcfortine D;

1-(4-morpholinosulfenyl)-15,16-dehydro-17-ketomarcfortine D;

1-(2,4-dinitrobenzenesulfenyl)-15,16-dehydro-17-ketomarcfortine D;

24-propoxy-24,25-dihydro-15,16-dehydro-17-ketomarcfortine D;

1-(p-toluenesulfonyl)-15,16-dehydro-17-ketomarcfortine D;

1-acetyl-15,16-dehydro-17-ketomarcfortine D;

1-methyl-15,16-dehydro-17-ketomarcfortine D;

1-benzyl-15,16-dehydro-17-ketomarcfortine D;

1-dimethylcarbamoyl-15,16-dehydro-17-ketomarcfortine D;

1-methoxycarbonyl-15,16-dehydro-17-ketomarcfortine D;

14α-hydroxy-15,16-dehydro-17-ketomarcfortine A;

1-acetoxymethyl-14α-hydroxy-15,16-dehydro-17-ketomarcfortine A;

1-diethoxyphosphoryl-14α-hydroxy-15,16-dehydro-17-ketoxymarcfortine A;

1-dimethylsulfamoyl-14α-hydroxy-15,16-dehydro-17-ketomarcfortine A;

1-cyclopropylcarbonyl-14α-hydroxy-15,16-dehydro-17-ketomarcfortine A;

2-bicyclo[2.2.1]heptanoyl-14α-hydroxy-15,16-dehydro-17-ketomarcfortine A;

1-(1-piperidinyl)thiocarbonyl-14α-hydroxy-15,16-dehydro-17-ketomarcfortine A;

1-succinoyl-14α-hydroxy-15,16-dehydro-17-ketomarcfortine A;

1-(4-morpholinosulfenyl)-14α-hydroxy-15,16-dehydro-17-ketomarcfortine A;

1-(2,4-dinitrobenzenesulfenyl)-14α-hydroxy-15,16-dehydro-17-ketomarcfortine A;

24-propoxy-24,25-dihydro-14α-hydroxy-15,16-dehydro-17-ketomarcfortine A;

1-(p-toluenesulfonyl)-14α-hydroxy-15,16-dehydro-17-ketomarcfortine A;

1-acetyl-14α-hydroxy-15,16-dehydro-17-ketomarcfortine A;

1-methyl-14α-hydroxy-15,16-dehydro-17-ketomarcfortine A;

1-benzyl-14α-hydroxy-15,16-dehydro-17-ketomarcfortine A;

1-dimethylcarbamoyl-14α-hydroxy-15,16-dehydro-17-ketomarcfortine A;

1-methoxycarbonyl-14α-hydroxy-15,16-dehydro-17-ketomarcfortine A;

14α-hydroxy-15,16-dehydro-17-ketomarcfortine B;

24,25-dihydro-14α-hydroxy-15,16-dehydro-17-ketomarcfortine B;

24-methoxy-24,25-dihydro-14α-hydroxy-15,16-dehydro-17-ketomarcfortine B;

1-(p-toluenesulfonyl)-14α-hydroxy-15,16-dehydro-17-ketomarcfortine B;

1-ethyl-14α-hydroxy-15,16-dehydro-17-ketomarcfortine B;

1-benzyl-14α-hydroxy-15,16-dehydro-17-ketomarcfortine B;

18a-ethyl-14α-hydroxy-15,16-dehydro-17-ketomarcfortine B;

18a-benzyl-14α-hydroxy-15,16-dehydro-17-ketomarcfortine B;

18a-methoxyethoxymethyl-14α-hydroxy-15,16-dehydro-17-ketomarcfortine B;

18a-allyl-14α-hydroxy-15,16-dehydro-17-ketomarcfortine B;

18a-propargyl-14α-hydroxy-15,16-dehydro-17-ketomarcfortine B;

18a-ethyl-24-methoxy-24,25-dihydro-14α-hydroxy-15,16-dehydro-17-ketomarcfortine B;

1,18a-bis-ethyl-14α-hydroxy-15,16-dehydro-17-ketomarcfortine B;

1,18a-bis-benzyl-14α-hydroxy-15,16-dehydro-17-ketomarcfortine B;

18a-ethyl-24-methoxy-14α-hydroxy-15,16-dehydro-17-ketomarcfortine B;

1-(2,4-dinitrobenzene sulfonyl)-18a-ethyl-24-methoxy-24,25-dihydro-14α-hydroxymarcfortine B;

18a-ethyl-24,25 dihydro-14α-hydroxy-15,16-dehydro-17-ketomarcfortine B;

24,25 dihydro-14α-hydroxy-15,16-dehydro-17-ketomarcfortine C;

1-(p-bromobenzene sulfonyl)-14α-hydroxy-15,16-dehydro-17-ketomarcfortine C;

1-propionyl-14α-hydroxy-15,16-dehydro-17-ketomarcfortine C;

1-propyl-14α-hydroxy-15,16-dehydro-17-ketomarcfortine C;

1-benzyl-14α-hydroxy-15,16-dehydro-17-ketomarcfortine C;

18a-propyl-14α-hydroxy-15,16-dehydro-17-ketomarcfortine C;

18a-benzyl-14α-hydroxy-15,16-dehydro-17-ketomarcfortine C;

18a-methoxyethoxymethyl-14α-hydroxy-15,16-dehydro-17-ketomarcfortine C;

18-allyl-14α-hydroxy-15,16-dehydro-17-ketomarcfortine C;

18a-propargyl-14α-hydroxy-15,16-dehydro-17-ketomarcfortine C;

1,18a-bis-propyl-14α-hydroxy-15,16-dehydro-17-ketomarcfortine C;

1,18a-bis-benzyl-14α-hydroxy-15,16-dehydro-17-ketomarcfortine C;

14α-hydroxy-15,16-dehydro-17-ketomarcfortine C;

1-(4-carbethoxy-1,3-thiazolidinin-3-yl)carbonyl-14α-hydroxy-15,16-dehydro-17-ketomarcfortine A;

1-palmitoyl-14α-hydroxy-15,16-dehydro-17-ketomarcfortine A;
1-(4-morpholinocarbonyl)-14α-hydroxy-15,16-dehydro-17-ketomarcfortine A;
1-palmitoyl-14α-hydroxy-15,16-dehydro-17-ketomarcfortine D;
1-(4-morpholinocarbonyl)-14α-hydroxy-15,16-dehydro-17-ketomarcfortine D;
14α-hydroxy-15,16-dehydro-17-ketomarcfortine D;
1-acetoxymethyl-14α-hydroxy-15,16-dehydro-17-ketomarcfortine D;
1-diethoxyphosphoryl-14α-hydroxy-15,16-dehydro-17-ketomarcfortine D;
1-dimethylsulfamoyl-14α-hydroxy-15,16-dehydro-17-ketomarcfortine D;
1-cyclopropylcarbonyl-14α-hydroxy-15,16-dehydro-17-ketomarcfortine D;
2-bicyclo[2.2.1]heptanoyl-14α-hydroxy-15,16-dehydro-17-ketomarcfortine D;
1-(1-piperidinyl)thiocarbonyl-14α-hydroxy-15,16-dehydro-17-ketomarcfortine D;
1-succinoyl-14α-hydroxy-15,16-dehydro-17-ketomarcfortine D;
1-(4-morpholinosulfenyl)-14α-hydroxy-15,16-dehydro-17-ketomarcfortine D;
1-(2,4-dinitrobenzenesulfenyl)-14α-hydroxy-15,16-dehydro-17-ketomarcfortine D;
24-propoxy-24,25-dihydro-14α-hydroxy-15,16-dehydro-17-ketomarcfortine D;
1-(p-toluenesulfonyl)-14α-hydroxy-15,16-dehydro-17-ketomarcfortine D;
1-acetyl-14α-hydroxy-15,16-dehydro-17-ketomarcfortine D;
1-methyl-14α-hydroxy-15,16-dehydro-17-ketomarcfortine D;
1-benzyl-14α-hydroxy-15,16-dehydro-17-ketomarcfortine D;
1-dimethylcarbamoyl-14α-hydroxy-15,16-dehydro-17-ketomarcfortine D;
1-methoxycarbonyl-14α-hydroxy-15,16-dehydro-17-ketomarcfortine D;
14α-hydroxy-17-ketomarcfortine A;
1-acetoxymethyl-14α-hydroxy-17-ketomarcfortine A;
1-diethoxyphosphoryl-14α-hydroxy-17-ketoxymarcfortine A;
1-dimethylsulfamoyl-14α-hydroxy-17-ketomarcfortine A;
1-cyclopropylcarbonyl-14α-hydroxy-17-ketomarcfortine A;
2-bicyclo[2.2.1]heptanoyl-14α-hydroxy-17-ketomarcfortine A;
1-(1-piperidinyl)thiocarbonyl-14α-hydroxy-17-ketomarcfortine A;
1-succinoyl-14α-hydroxy-17-ketomarcfortine A;
1-(4-morpholinosulfenyl)-14α-hydroxy-17-ketomarcfortine A;
1-(2,4-dinitrobenzenesulfenyl)-14α-hydroxy-17-ketomarcfortine A;
24-propoxy-24,25-dihydro-14α-hydroxy-17-ketomarcfortine A;
1-(p-toluenesulfonyl)-14-α-hydroxy-17-ketomarcfortine A;
1-acetyl-14α-hydroxy-17-ketomarcfortine A;
1-methyl-14α-hydroxy-17-ketomarcfortine A;
1-benzyl-14α-hydroxy-17-ketomarcfortine A;
1-dimethylcarbamoyl-14α-hydroxy-17-ketomarcfortine A;
1-methoxycarbonyl-14α-hydroxy-17-ketomarcfortine A;
14α-hydroxy-17-ketomarcfortine B;
24,25-dihydro-14α-hydroxy-17-ketomarcfortine B;
24-methoxy-24,25-dihydro-14α-hydroxy-17-ketomarcfortine B;
1-(p-toluenesulfonyl)-14α-hydroxy-17-ketomarcfortine B;
1-ethyl-14α-hydroxy-17-ketomarcfortine B;
1-benzyl-14α-hydroxy-17-ketomarcfortine B;
18a-ethyl-14α-hydroxy-17-ketomarcfortine B;
18a-benzyl-14α-hydroxy-17-ketomarcfortine B;
18a-methoxyethoxymethyl-14α-hydroxy-17-ketomarcfortine B;
18a-allyl-14α-hydroxy-17-ketomarcfortine B;
18a-propargyl-14α-hydroxy-17-ketomarcfortine B;
18a-ethyl-24-methoxy-24,25-dihydro-14α-hydroxy-17-ketomarcfortine B;
1,18a-bis-ethyl-14α-hydroxy-17-ketomarcfortine B;
1,18a-bis-benzyl-14α-hydroxy-17-ketomarcfortine B;
18a-ethyl-24-methoxy-14α-hydroxy-17-ketomarcfortine B;
1-(2,4-dinitrobenzene sulfonyl)-18a-ethyl-24-methoxy-24,25-dihydro-14α-hydroxymarcfortine B;
18a-ethyl-24,25 dihydro-14α-hydroxy-17-ketomarcfortine B;
24,25 dihydro-14α-hydroxy-17-ketomarcfortine C;
1-(p-bromobenzene sulfonyl)-14α-hydroxy-17-ketomarcfortine C;
1-propionyl-14α-hydroxy-17-ketomarcfortine C;
1-propyl-14α-hydroxy-17-ketomarcfortine C;
1-benzyl-14α-hydroxy-17-ketomarcfortine C;
18a-propyl-14α-hydroxy-17-ketomarcfortine C;
18a-benzyl-14α-hydroxy-17-ketomarcfortine C;
18a-methoxyethoxymethyl-14α-hydroxy-17-ketomarcfortine C;
18-allyl-14α-hydroxy-17-ketomarcfortine C;
18a-propargyl-14α-hydroxy-17-ketomarcfortine C;
1,18a-bis-propyl-14α-hydroxy-17-ketomarcfortine C;
1,18a-bis-benzyl-14α-hydroxy-17-ketomarcfortine C;
14α-hydroxy-17-ketomarcfortine C;
1-(4-carbethoxy-1,3-thiazolidinin-3-yl)carbonyl-14α-hydroxy-17-ketomarcfortine A;
1-palmitoyl-14α-hydroxy-17-ketomarcfortine A;
1-(4-morpholinocarbonyl)-14α-hydroxy-17-ketomarcfortine A;
1-palmitoyl-14α-hydroxy-17-ketomarcfortine D;
1-(4-morpholinocarbonyl)-14α-hydroxy-17-ketomarcfortine D;
14α-hydroxy-17-ketomarcfortine D;
1-acetoxymethyl-14α-hydroxy-17-ketomarcfortine D;
1-diethoxyphosphoryl-14α-hydroxy-17-ketomarcfortine D;
1-dimethylsulfamoyl-14α-hydroxy-17-ketomarcfortine D;

1-cyclopropylcarbonyl-14α-hydroxy-17-ketomarcfortine D;
2-bicyclo[2.2.1]heptanoyl-14α-hydroxy-17-ketomarcfortine D;
1-(1-piperidinyl)thiocarbonyl-14α-hydroxy-17-ketomarcfortine D;
1-succinoyl-14α-hydroxy-17-ketomarcfortine D;
1-(4-morpholinosulfenyl)-14α-hydroxy-17-ketomarcfortine D;
1-(2,4-dinitrobenzenesulfenyl)-14α-hydroxy-17-ketomarcfortine D;
24-propoxy-24,25-dihydro-14α-hydroxy-17-ketomarcfortine D;
1-(p-toluenesulfonyl)-14α-hydroxy-17-ketomarcfortine D;
1-acetyl-14α-hydroxy-17-ketomarcfortine D;
1-methyl-14α-hydroxy-17-ketomarcfortine D;
1-benzyl-14α-hydroxy-17-ketomarcfortine D;
1-dimethylcarbamoyl-14α-hydroxy-17-ketomarcfortine D;
1-methoxycarbonyl-14α-hydroxy-17-ketomarcfortine D;
14,17-diketomarcfortine A;
1-acetoxymethyl-14,17-diketomarcfortine A;
1-diethoxyphosphoryl-14,17-diketoxymarcfortine A;
1-dimethylsulfamoyl-14,17-diketomarcfortine A;
1-cyclopropylcarbonyl-14,17-diketomarcfortine A;
2-bicyclo[2.2.1]heptanoyl-14,17-diketomarcfortine A;
1-(1-piperidinyl)thiocarbonyl-14,17-diketomarcfortine A;
1-succinoyl-14,17-diketomarcfortine A;
1-(4-morpholinosulfenyl)-14,17-diketomarcfortine A;
1-(2,4-dinitrobenzenesulfenyl)-14,17-diketomarcfortine A;
24-propoxy-24,25-dihydro-14,17-diketomarcfortine A;
1-(p-toluenesulfonyl)-14,17-diketomarcfortine A;
1-acetyl-14,17-diketomarcfortine A;
1-methyl-14,17-diketomarcfortine A;
1-benzyl-14,17-diketomarcfortine A;
1-dimethylcarbamoyl-14,17-diketomarcfortine A;
1-methoxycarbonyl-14,17-diketomarcfortine A;
14,17-diketomarcfortine B;
24,25-dihydro-14,17-diketomarcfortine B;
24-methoxy-24,25-dihydro-14,17-diketomarcfortine B;
1-(p-toluenesulfonyl)-14,17-diketomarcfortine B;
1-ethyl-14,17-diketomarcfortine B;
1-benzyl-14,17-diketomarcfortine B;
18a-ethyl-14,17-diketomarcfortine B;
18a-benzyl-14,17-diketomarcfortine B;
18a-methoxyethoxymethyl-14,17-diketomarcfortine B;
18a-allyl-14,17-diketomarcfortine B;
18a-propargyl-14,17-diketomarcfortine B;
18a-ethyl-24-methoxy-24,25-dihydro-14,17-diketomarcfortine B;
1,18a-bis-ethyl-14,17-diketomarcfortine B;
1,18a-bis-benzyl-14,17-diketomarcfortine B;
18a-ethyl-24-methoxy-14,17-diketomarcfortine B;
1-(2,4-dinitrobenzene sulfonyl)-18a-ethyl-24-methoxy-24,25-dihydro-14α-hydroxymarcfortine B;
18a-ethyl-24,25 dihydro-14,17-diketomarcfortine B;
24,25 dihydro-14,17-diketomarcfortine C;
1-(p-bromobenzene sulfonyl)-14,17-diketomarcfortine C;
1-propionyl-14,17-diketomarcfortine C;
1-propyl-14,17-diketomarcfortine C;
1-benzyl-14,17-diketomarcfortine C;
18a-propyl-14,17-diketomarcfortine C;
18a-benzyl-14,17-diketomarcfortine C;
18a-methoxyethoxymethyl-14,17-diketomarcfortine C;
18-allyl-14,17-diketomarcfortine C;
18a-propargyl-14,17-diketomarcfortine C;
1,18a-bis-propyl-14,17-diketomarcfortine C;
1,18a-bis-benzyl-14,17-diketomarcfortine C;
14,17-diketomarcfortine C;
1-(4-carbethoxy-1,3-thiazolidinin-3-yl)carbonyl-14,17-diketomarcfortine A;
1-palmitoyl-14,17-diketomarcfortine A;
1-(4-morpholinocarbonyl)-14,17-diketomarcfortine A;
1-palmitoyl-14,17-diketomarcfortine D;
1-(4-morpholinocarbonyl)-14,17-diketomarcfortine D;
14,17-diketomarcfortine D;
1-acetoxymethyl-14,17-diketomarcfortine D;
1-diethoxyphosphoryl-14,17-diketomarcfortine D;
1-dimethylsulfamoyl-14,17-diketomarcfortine D;
1-cyclopropylcarbonyl-14,17-diketomarcfortine D;
2-bicyclo[2.2.1]heptanoyl-14,17-diketomarcfortine D;
1-(1-piperidinyl)thiocarbonyl-14,17-diketomarcfortine D;
1-succinoyl-14,17-diketomarcfortine D;
1-(4-morpholinosulfenyl)-14,17-diketomarcfortine D;
1-(2,4-dinitrobenzenesulfenyl)-14,17-diketomarcfortine D;
24-propoxy-24,25-dihydro-14,17-diketomarcfortine D;
1-(p-toluenesulfonyl)-14,17-diketomarcfortine D;
1-acetyl-14,17-diketomarcfortine D;
1-methyl-14,17-diketomarcfortine D;
1-benzyl-14,17-diketomarcfortine D;
1-dimethylcarbamoyl-14,17-diketomarcfortine D;
1-methoxycarbonyl-14,17-diketomarcfortine D;
15,16-dehydro-14,17-diketomarcfortine A;
1-acetoxymethyl-15,16-dehydro-14,17-diketomarcfortine A;
1-diethoxyphosphoryl-15,16-dehydro-14,17-diketoxymarcfortine A;
1-dimethylsulfamoyl-15,16-dehydro-14,17-diketomarcfortine A;
1-cyclopropylcarbonyl-15,16-dehydro-14,17-diketomarcfortine A;
2-bicyclo[2.2.1]heptanoyl-15,16-dehydro-14,17-diketomarcfortine A;
1-(1-piperidinyl)thiocarbonyl-15,16-dehydro-14,17-diketomarcfortine A;
1-succinoyl-15,16-dehydro-14,17-diketomarcfortine A;
1-(4-morpholinosulfenyl)-15,16-dehydro-14,17-diketomarcfortine A;
1-(2,4-dinitrobenzenesulfenyl)-15,16-dehydro-14,17-diketomarcfortine A;
24-propoxy-24,25-dihydro-15,16-dehydro-14,17-diketomarcfortine A;

1-(p-toluenesulfonyl)-15,16-dehydro-14,17-diketomarcfortine A;
1-acetyl-15,16-dehydro-14,17-diketomarcfortine A;
1-methyl-15,16-dehydro-14,17-diketomarcfortine A;
1-benzyl-15,16-dehydro-14,17-diketomarcfortine A;
1-dimethylcarbamoyl-15,16-dehydro-14,17-diketomarcfortine A;
1-methoxycarbonyl-15,16-dehydro-14,17-diketomarcfortine A;
15,16-dehydro-14,17-diketomarcfortine B;
24,25-dihydro-15,16-dehydro-14,17-diketomarcfortine B;
24-methoxy-24,25-dihydro-15,16-dehydro-14,17-diketomarcfortine B;
1-(p-toluenesulfonyl)-15,16-dehydro-14,17-diketomarcfortine B;
1-ethyl-15,16-dehydro-14,17-diketomarcfortine B;
1-benzyl-15,16-dehydro-14,17-diketomarcfortine B;
18a-ethyl-15,16-dehydro-14,17-diketomarcfortine B;
18a-benzyl-15,16-dehydro-14,17-diketomarcfortine B;
18a-methoxyethoxymethyl-15,16-dehydro-14,17-diketomarcfortine B;
18a-allyl-15,16-dehydro-14,17-diketomarcfortine B;
18a-propargyl-15,16-dehydro-14,17-diketomarcfortine B;
18a-ethyl-24-methoxy-24,25-dihydro-15,16-dehydro-14,17-diketomarcfortine B;
1,18a-bis-ethyl-15,16-dehydro-14,17-diketomarcfortine B;
1,18a-bis-benzyl-15,16-dehydro-14,17-diketomarcfortine B;
18a-ethyl-24-methoxy-15,16-dehydro-14,17-diketomarcfortine B;
1-(2,4-dinitrobenzene sulfonyl)-18a-ethyl-24-methoxy-24,25-dihydro-14α-hydroxymarcfortine B;
18a-ethyl-24,25 dihydro-15,16-dehydro-14,17-diketomarcfortine B;
24,25 dihydro-15,16-dehydro-14,17-diketomarcfortine C;
1-(p-bromobenzene sulfonyl)-15,16-dehydro-14,17-diketomarcfortine C;
1-propionyl-15,16-dehydro-14,17-diketomarcfortine C;
1-propyl-15,16-dehydro-14,17-diketomarcfortine C;
1-benzyl-15,16-dehydro-14,17-diketomarcfortine C;
18a-propyl-15,16-dehydro-14,17-diketomarcfortine C;
18a-benzyl-15,16-dehydro-14,17-diketomarcfortine C;
18a-methoxyethoxymethyl-15,16-dehydro-14,17-diketomarcfortine C;
18-allyl-15,16-dehydro-14,17-diketomarcfortine C;
18a-propargyl-15,16-dehydro-14,17-diketomarcfortine C;
1,18a-bis-propyl-15,16-dehydro-14,17-diketomarcfortine C;
1,18a-bis-benzyl-15,16-dehydro-14,17-diketomarcfortine C;
15,16-dehydro-14,17-diketomarcfortine C;
1-(4-carbethoxy-1,3-thiazolidinin-3-yl)carbonyl-15,16-dehydro-14,17-diketomarcfortine A;
1-palmitoyl-15,16-dehydro-14,17-diketomarcfortine A;
1-(4-morpholinocarbonyl)-15,16-dehydro-14,17-diketomarcfortine A;
1-palmitoyl-15,16-dehydro-14,17-diketomarcfortine D;
1-(4-morpholinocarbonyl)-15,16-dehydro-14,17-diketomarcfortine D;
15,16-dehydro-14,17-diketomarcfortine D;
1-acetoxymethyl-15,16-dehydro-14,17-diketomarcfortine D;
1-diethoxyphosphoryl-15,16-dehydro-14,17-diketomarcfortine D;
1-dimethylsulfamoyl-15,16-dehydro-14,17-diketomarcfortine D;
1-cyclopropylcarbonyl-15,16-dehydro-14,17-diketomarcfortine D;

2-bicyclo[2.2.1]heptanoyl-15,16-dehydro-14,17-diketomarcfortine D;

1-(1-piperidinyl)thiocarbonyl-15,16-dehydro-14,17-diketomarcfortine D;

1-succinoyl-15,16-dehydro-14,17-diketomarcfortine D;

1-(4-morpholinosulfenyl)-15,16-dehydro-14,17-diketomarcfortine D;

1-(2,4-dinitrobenzenesulfenyl)-15,16-dehydro-14,17-diketomarcfortine D;

24-propoxy-24,25-dihydro-15,16-dehydro-14,17-diketomarcfortine D;

1-(p-toluenesulfonyl)-15,16-dehydro-14,17-diketomarcfortine D;

1-acetyl-15,16-dehydro-14,17-diketomarcfortine D;

1-methyl-15,16-dehydro-14,17-diketomarcfortine D;

1-benzyl-15,16-dehydro-14,17-diketomarcfortine D;

1-dimethylcarbamoyl-15,16-dehydro-14,17-diketomarcfortine D;

1-methoxycarbonyl-15,16-dehydro-14,17-diketomarcfortine D;

14α-hydroxy-14,3-methyl-17-ketomarcfortine A;

1-acetoxymethyl-14α-hydroxy- 14β-methyl-17-ketomarcfortine A;

1-diethoxyphosphoryl-14α-hydroxy-14β-methyl-17-ketoxymarcfortine A;

1-dimethylsulfamoyl-14α-hydroxy-14β-methyl-17-ketomarcfortine A;

1-cyclopropylcarbonyl-14α-hydroxy-14β-methyl-17-ketomarcfortine A;

2-bicyclo[2.2.1]heptanoyl-14α-hydroxy-14β-methyl-17-ketomarcfortine A;

1-(1-piperidinyl)thiocarbonyl-14α-hydroxy-14β-methyl-17-ketomarcfortine A;

1-succinoyl-14α-hydroxy-14β-methyl-17-ketomarcfortine A;

1-(4-morpholinosulfenyl)-14α-hydroxy-14β-methyl-17-ketomarcfortine A;

1 -(2,4-dinitrobenzenesulfenyl)-14α-hydroxy-14β-methyl-17-ketomarcfortine A;

24-propoxy-24,25-dihydro-14α-hydroxy-14β-methyl-17-ketomarcfortine A;

1-(p-toluenesulfonyl)-14α-hydroxy-14β-methyl-17-ketomarcfortine A;

1-acetyl-14α-hydroxy-14β-methyl-17-ketomarcfortine A;

1-methyl-14α-hydroxy-14β-methyl-17-ketomarcfortine A;

1-benzyl-14-hydroxy-14β-methyl-17-ketomarcfortine A;

1-dimethylcarbamoyl-14α-hydroxy-14β-methyl-17-ketomarcfortine A;

1-methoxycarbonyl-14α-hydroxy-14β-methyl-17-ketomarcfortine A;

14α-hydroxy-14β-methyl-17-ketomarcfortine B;

24,25-dihydro-14α-hydroxy-14β-methyl-17-ketomarcfortine B;

24-methoxy-24,25-dihydro-14α-hydroxy-14β-methyl-17-ketomarcfortine B;

1-(p-toluenesulfonyl)-14α-hydroxy-14β-methyl-17-ketomarcfortine B;

1-ethyl-14α-hydroxy-14,-methyl-17-ketomarcfortine B;

1-benzyl-14α-hydroxy-14β-methyl-17-ketomarcfortine B;

18a-ethyl-14α-hydroxy-14β-methyl-17-ketomarcfortine B;

18a-benzyl-14α-hydroxy-14β-methyl-17-ketomarcfortine B;

18a-methoxyethoxymethyl-14α-hydroxy-14β-methyl-17-ketomarcfortine B;

18a-allyl-14α-hydroxy-14β-methyl-17-ketomarcfortine B;

18a-propargyl-14α-hydroxy-14β-methyl-17-ketomarcfortine B;

18a-ethyl-24-methoxy-24,25-dihydro-14α-hydroxy-14β-methyl-17-ketomarcfortine B;

1,18a-bis-ethyl-14α-hydroxy-14β-methyl-17-ketomarcfortine B;

1,18a-bis-benzyl-14α-hydroxy-14β-methyl-17-ketomarcfortine B;

18a-ethyl-24-methoxy-14α-hydroxy-14β-methyl-17-ketomarcfortine B;

1-(2,4-dinitrobenzene sulfonyl)-18a-ethyl-24-methoxy-24,25-dihydro-14α- hydroxymarcfortine B;

18a-ethyl-24,25 dihydro-14α-hydroxy-14β-methyl-17-ketomarcfortine B;

24,25 dihydro-14α-hydroxy-14β-methyl-17-ketomarcfortine C;

1-(p-bromobenzene sulfonyl)-14α-hydroxy-14β-methyl-17-ketomarcfortine C;

1-propionyl-14α-hydroxy-14β-methyl-17-ketomarcfortine C;

1-propyl-14α-hydroxy-14β-methyl-17-ketomarcfortine C;

1-benzyl-14α-hydroxy-14β-methyl-17-ketomarcfortine C;

18a-propyl-14α-hydroxy-14β-methyl-17-ketomarcfortine C;

18a-benzyl-14α-hydroxy-14β-methyl-17-ketomarcfortine C;

18a-methoxyethoxymethyl-14α-hydroxy-14β-methyl-17-ketomarcfortine C;

18-allyl-14α-hydroxy-14β-methyl-17-ketomarcfortine C;

18a-propargyl-14α-hydroxy-14β-methyl-17-ketomarcfortine C;

1,18a-bis-propyl-14α-hydroxy-14β-methyl-17-ketomarcfortine C;

1,18a-bis-benzyl-14α-hydroxy-14β-methyl-17-ketomarcfortine C;

14α-hydroxy-14β-methyl-17-ketomarcfortine C;

1-(4-carbethoxy-1,3-thiazolidinin-3-yl)carbonyl-14α-hydroxy-14β-methyl-17-ketomarcfortine A;

1-palmitoyl-14α-hydroxy-14β-methyl-17-ketomarcfortine A;

1-(4-morpholinocarbonyl)-14α-hydroxy-14β-methyl-17-ketomarcfortine A;

1-palmitoyl-14α-hydroxy-14β-methyl-17-ketomarcfortine D;

1-(4-morpholinocarbonyl)-14α-hydroxy-14β-methyl-17-ketomarcfortine D;

14α-hydroxy-14β-methyl-17-ketomarcfortine D;

1-acetoxymethyl-14α-hydroxy-14β-methyl-17-ketomarcfortine D;

1-diethoxyphosphoryl-14α-hydroxy-14β-methyl-17-ketomarcfortine D;

1-dimethylsulfamoyl-14α-hydroxy-14β-methyl-17-ketomarcfortine D;

1-cyclopropylcarbonyl-14α-hydroxy-14β-methyl-17-ketomarcfortine D;

2-bicyclo[2.2.1]heptanoyl-14α-hydroxy-14p-methyl-17-ketomarcfortine D;

1-(1-piperidinyl)thiocarbonyl-14α-hydroxy-14β-methyl-17-ketomarcfortine D;

1-succinoyl-14α-hydroxy-14β-methyl-17-ketomarcfortine D;

1-(4-morpholinosulfenyl)-14α-hydroxy-14β-methyl-17-ketomarcfortine D;

1-(2,4-dinitrobenzenesulfenyl)-14α-hydroxy-14β-methyl-17-ketomarcfortine D;

24-propoxy-24,25-dihydro-14α-hydroxy-14β-methyl-17-ketomarcfortine D;

1-(p-toluenesulfonyl)-14α-hydroxy-14β-methyl-17-ketomarcfortine D;

1-acetyl-14α-hydroxy-14β-methyl-17-ketomarcfortine D;

1-methyl-14α-hydroxy-14β-methyl-17-ketomarefortine D;

1-benzyl-14α-hydroxy-14β-methyl-17-ketomarefortine D;

1-dimethylcarbamoyl-14α-hydroxy-14β-methyl-17-ketomarcfortine D;

1-methoxycarbonyl-14α-hydroxy-14β-methyl-17-ketomarcfortine D;

14-ketomarcfortine A;

1-acetoxymethyl-14-ketomarcfortine A;

1-diethoxyphosphoryl-14-ketoxymarcfortine A;

1-dimethylsulfamoyl-14-ketomarcfortine A;

1-cyclopropylcarbonyl-14-ketomarcfortine A;

2-bicyclo[2.2.1]heptanoyl-14-ketomarcfortine A;

1-(1-piperidinyl)thiocarbonyl-14-ketomarcfortine A;

1-succinoyl-14-ketomarcfortine A;

1-(4-morpholinosulfenyl)-14-ketomarcfortine A;

1-(2,4-dinitrobenzenesulfenyl)-14-ketomarcfortine A;

24-propoxy-24,25-dihydro-14-ketomarcfortine A;

1-(p-toluenesulfonyl)-14-ketomarcfortine A;

1-acetyl-14-ketomarcfortine A;

1-methyl-14-ketomarcfortine A;

1-benzyl-14-ketomarcfortine A;

1-dimethylcarbamoyl-14-ketomarcfortine A;

1-methoxycarbonyl-14-ketomarcfortine A;

14-ketomarcfortine B;

24,25-dihydro-14-ketomarcfortine B;

24-methoxy-24,25-dihydro-14-ketomarcfortine B;

1-(p-toluenesulfonyl)-14-ketomarcfortine B;

1-ethyl-14-ketomarcfortine B;
1-benzyl-14-ketomarcfortine B;
18a-ethyl-14-ketomarcfortine B;
18a-benzyl-14ketomarcfortine B;
18a-methoxyethoxymethyl-14-ketomarcfortine B;
18a-allyl-14ketomarcfortine B;
18a-propargyl-14-ketomarcfortine B;
18a-ethyl-24-methoxy-24,25-dihydro-14-ketomarcfortine B;
1,18a-bis-ethyl-14-ketomarcfortine B;
1,18a-bis-benzyl-14-ketomarcfortine B;
18a-ethyl-24-methoxy-14-ketomarcfortine B;
1-(2,4-dinitrobenzene sulfonyl)-18α-ethyl-24-methoxy-24,25-dihydro-14α- hydroxymarcfortine B;
18a-ethyl-24,25 dihydro-14-ketomarcfortine B;
24,25 dihydro-14-ketomarcfortine C;
1-(p-bromobenzene sulfonyl)-14-ketomarcfortine C;
1-propionyl-14-ketomarcfortine C;
1-propyl-14-ketomarcfortine C;
1-benzyl-14-ketomarcfortine C;
18a-propyl-14-ketomarcfortine C;
18a-benzyl-14-ketomarcfortine C;
18a-methoxyethoxymethyl-14-ketomarcfortine C;
18-allyl-14-ketomarcfortine C;
18a-propargyl-14-ketomarcfortine C;
1,18a-bis-propyl-14-ketomarcfortine C;
1,18a-bis-benzyl-14-ketomarcfortine C;
14-ketomarcfortine C;
1-(4-carbethoxy-1,3-thiazolidinin-3-yl)carbonyl-14-ketomarcfortine A;
1-palmitoyl-14-ketomarcfortine A;
1-(4-morpholinocarbonyl)-14-ketomarcfortine A;
1-palmitoyl-14-ketomarcfortine D;
1-(4-morpholinocarbonyl)-14-ketomarcfortine D;
14-ketodroxymarcfortine D;
1-acetoxymethyl-14ketomarcfortine D;
1-diethoxyphosphoryl-14-ketomarcfortine D;
1-dimethylsulfamoyl-14ketomarcfortine D;
1-cyclopropylcarbonyl-14-ketomarcfortine D;
2-bicyclo[2.2.1]heptanoyl-14-ketomarcfortine D;
1-(1-piperidinyl)thiocarbonyl-14-ketomarcfortine D;
1-succinoyl-14-ketomarcfortine D;
1-(4-morpholinosulfenyl)-14ketomarcfortine D;
1-(2,4-dinitrobenzenesulfenyl)-14-ketomarcfortine D;
24-propoxy-24,25-dihydro-14-ketomarcfortine D;
1-(p-toluenesulfonyl)-14-ketomarcfortine D;
1-acetyl-14-ketomarcfortine D;
1-methyl-14-ketomarcfortine D;
1-benzyl-14-ketomarcfortine D;
1-dimethylcarbamoyl-14-ketomarcfortine D;
1-methoxycarbonyl-14-ketomarcfortine D;
16-dithio-17-ketomarcfortine A;
1-acetoxymethyl-16-dithio-17-ketomarcfortine A;
1-diethoxyphosphoryl-16-dithio-17-ketoxymarcfortine A;
1-dimethylsulfamoyl-16-dithio-17-ketomarcfortine A;
1-cyclopropylcarbonyl-16-dithio-17-ketomarcfortine A;
2-bicyclo[2.2.1]heptanoyl-16-dithio-17-ketomarcfortine A;
1-(1-piperidinyl)thiocarbonyl-16-dithio-17-ketomarcfortine A;
1-succinoyl-16-dithio-17-ketomarcfortine A;
1-(4-morpholinosulfenyl)-16-dithio-17-ketomarcfortine A;
1-(2,4-dinitrobenzenesulfenyl)-16-dithio-17-ketomarcfortine A;
24-propoxy-24,25-dihydro-16-dithio-17-ketomarcfortine A;
1-(p-toluenesulfonyl)-16-dithio-17-ketomarcfortine A;
1-acetyl-16-dithio-17-ketomarcfortine A;
1-methyl-16-dithio-17-ketomarcfortine A;
1-benzyl-16-dithio-17-ketomarcfortine A;
1-dimethylcarbamoyl-16-dithio-17-ketomarcfortine A;
1-methoxycarbonyl-16-dithio-17-ketomarcfortine A;
16-dithio-17-ketomarcfortine B;
24,25-dihydro-16-dithio-17-ketomarcfortine B;
24-methoxy-24,25-dihydro-16-dithio-17-ketomarcfortine B;
1-(p-toluenesulfonyl)-16-dithio-17-ketomarcfortine B;
1-ethyl-16-dithio-17-ketomarcfortine B;
1-benzyl-16-dithio-17-ketomarcfortine B;
18a-ethyl-16-dithio-17-ketomarcfortine B;
18a-benzyl-16-dithio-17-ketomarcfortine B;
18a-methoxyethoxymethyl-16-dithio-17-ketomarcfortine B;
18a-allyl-16-dithio-17-ketomarcfortine B;
18a-propargyl-16-dithio-17-ketomarcfortine B;
18a-ethyl-24-methoxy-24,25-dihydro-16-dithio-17-ketomarcfortine B;
1,18a-bis-ethyl-16-dithio-17-ketomarcfortine B;
1,18a-bis-benzyl-16-dithio-17-ketomarcfortine B;
18a-ethyl-24-methoxy-16-dithio-17-ketomarcfortine B;
1-(2,4-dinitrobenzene sulfonyl)-18a-ethyl-24-methoxy-24,25-dihydro-14α- hydroxymarcfortine B;
18a-ethyl-24,25 dihydro-16-dithio-17-ketomarcfortine B;
24,25 dihydro-16-dithio-17-ketomarcfortine C;
1-(p-bromobenzene sulfonyl)-16-dithio-17-ketomarcfortine C;
1-propionyl-16-dithio-17-ketomarcfortine C;
1-propyl-16-dithio-17-ketomarcfortine C;
1-benzyl-16-dithio-17-ketomarcfortine C;
18a-propyl-16-dithio-17-ketomarcfortine C;
18a-benzyl-16-dithio-17-ketomarcfortine C;
18a-methoxyethoxymethyl-16-dithio-17-ketomarcfortine C;
18-allyl-16-dithio-17-ketomarcfortine C;
18a-propargyl-16-dithio-17-ketomarcfortine C;
1,18a-bis-propyl-16-dithio-17-ketomarcfortine C;
1,18a-bis-benzyl-16-dithio-17-ketomarcfortine C;
16-dithio-17-ketomarcfortine C;
1-(4-carbethoxy-1,3-thiazolidinin-3-yl)carbonyl-16-dithio-17-ketomarcfortine A;
1-paliitoyl-16-dithio-17-ketomarcfortine A;
1-(4-morpholinocarbonyl)-16-dithio-17-ketomarcfortine A;
1-palmitoyl-16-dithio-17-ketomarcfortine D;

1-(4-morpholinocarbonyl)-16-dithio-17-ketomarcfortine D;

16-dithio-17-ketodroxymarcfortine D;

1-acetoxymethyl-16-dithio-17-ketomarcfortine D;

1-diethoxyphosphoryl-16-dithio-17-ketomarcfortine D;

1-dimethylsulfamoyl-16-dithio-17-ketomarcfortine D;

1-cyclopropylcarbonyl-16-dithio-17-ketomarcfortine D;

2-bicyclo[2.2.1]heptanoyl-16-dithio-17-ketomarcfortine D;

1-(1-piperidinyl)thiocarbonyl-16-dithio-17-ketomarcfortine D;

1-succinoyl-16-dithio-17-ketomarcfortine D;

1-(4-morpholinosulfenyl)-16-dithio-17-ketomarcfortine D;

1-(2,4-dinitrobenzenesulfenyl)-16-dithio-17-ketomarcfortine D;

24-propoxy-24,25-dihydro-16-dithio-17-ketomarcfortine D;

1-(p-toluenesulfonyl)-16-dithio-17-ketomarcfortine D;

1-acetyl-16-dithio-17-ketomarcfortine D;

1-methyl-16-dithio-17-ketomarcfortine D;

1-benzyl-16-dithio-17-ketomarcfortine D;

1-dimethylcarbarnoyl-16-dithio-17-ketomarcfortine D; or 1-methoxycarbonyl-16-dithio-17-ketomarcfortine D.

16-thiophenyl-15,16-dehydro-17-ketomarcfortine A;

1-acetoxymethyl-16-thiophenyl-15,16-dehydro-17-ketomarcfortine A;

1-diethoxyphosphoryl-16-thiophenyl-15,16-dehydro-17-ketoxymarcfortine A;

1-dimethylsulfamoyl-16-thiophenyl-15,16-dehydro-17-ketomarcfortine A;

1-cyclopropylcarbonyl-16-thiophenyl-15,16-dehydro-17-ketomarcfordne A;

2-bicyclo [2.2.1]heptanoyl-16-thiophenyl-15,16-dehydro-17-ketomarcfortine A;

1-(1-piperidinyl)thiocarbonyl-16-thiophenyl-15,16-dehydro-17-ketomarcfortine A;

1-succinoyl-16-thiophenyl-15,16-dehydro-17-ketomarcfortine A;

1-(4-morpholinosulfenyl)-16-thiophenyl-15,16-dehydro-17-ketomarcfortine A;

1-(2,4-dinitrobenzenesulfenyl)-16-thiophenyl-15,16-dehydro-17-ketomarcfortine A;

24-propoxy-24,25-dihydro-16-thiophenyl-15,16-dehydro-17-ketomarcfortine A;

1-(p-toluenesulfonyl)-16-thiophenyl-15,16-dehydro-17-ketomarcfortine A;

1-acetyl-16-thiophenyl-15,16-dehydro-17-ketomarcfortine A;

1-methyl-16-thiophenyl-15,16-dehydro-17-ketomarcfortine A;

1-benzyl-16-thiophenyl-15,16-dehydro-17-ketomarcfortine A;

1-dimethylcarbamoyl-16-thiophenyl-15,16-dehydro-17-ketomarcfortine A;

1-methoxycarbonyl-16-thiophenyl-15,16-dehydro-17-ketomarcfortine A;

16-thiophenyl-15,16-dehydro-17-ketomarcfortine B;

24,25-dihydro-16-thiophenyl-15,16-dehydro-17-ketomarcfortine B;

24-methoxy-24,25-dihydro-16-thiophenyl-15,16-dehydro-17-ketomarcfortine B;

1-(p-toluenesulfonyl)-16-thiophenyl-15,16-dehydro-17-ketomarcfortine B;

1-ethyl-16-thiophenyl-15,16-dehydro-17-ketomarcfortine B;

1-benzyl-16-thiophenyl-15,16-dehydro-17-ketomarcfortine B;

18a-ethyl-16-thiophenyl-15,16-dehydro-17-ketomarcfortine B;

18a-benzyl-16-thiophenyl-15,16-dehydro-17-ketomarcfortine B;

18a-methoxyethoxymethyl-16-thiophenyl-15,16-dehydro-17-ketomarcfortine B;

18a-allyl-16-thiophenyl-15,16-dehydro-17-ketomarcfortine B;

18a-propargyl-16-thiophenyl-15,16-dehydro-17-ketomarcfortine B;

18a-ethyl-24-methoxy-24,25-dihydro-16-thiophenyl-15,16-dehydro-17-ketomarcfortine B;

1,18a-bis-ethyl-16-thiophenyl-15,16-dehydro-17-ketomarcfortine B;

1,18a-bis-benzyl-16-thiophenyl-15,16-dehydro-17-ketomarcfortine B;

18a-ethyl-24-methoxy-16-thiophenyl-15,16-dehydro-17-ketomarcfortine B;

1-(2,4-dinitrobenzene sulfonyl)-18a-ethyl-24-methoxy-24,25-dihydro-14α-hydroxymarcfortine B;

18a-ethyl-24,25 dihydro-16-thiophenyl-15,16-dehydro-17-ketomarcfortine B;

24,25 dihydro-16-thiophenyl-15,16-dehydro-17-ketomarcfortine C;

1-(p-bromobenzene sulfonyl)-16-thiophenyl-15,16-dehydro-17-ketomarcfortine C;

1-propionyl-16-thiophenyl-15,16-dehydro-17-ketomarcfortine C;

1-propyl-16-thiophenyl-15,16-dehydro-17-ketomarcfortine C;

1-benzyl-16-thiophenyl-15,16-dehydro-17-ketomarcfortine C;

18a-propyl-16-thiophenyl-15,16-dehydro-17-ketomarcfortine C;

18a-benzyl-16-thiophenyl-15,16-dehydro-17-ketomarcfortine C;

18a-methoxyethoxymethyl-16-thiophenyl-15,16-dehydro-17-ketomarcfortine C;

18-allyl-16-thiophenyl-15,16-dehydro-17-ketomarcfortine C;

18a-propargyl-16-thiophenyl-15,16-dehydro-17-ketomarcfortine C;

1,18a-bis-propyl-16-thiophenyl-15,16-dehydro-17-ketomarcfortine C;

1,18a-bis-benzyl-16-thiophenyl-15,16-dehydro-17-ketomarcfortine C;

16-thiophenyl-15,16-dehydro-17-ketomarcfortine C;

1-(4-carbethoxy-1,3-thiazolidinin-3-yl)carbonyl-16-thiophenyl-15,16-dehydro-17-ketomarcfortine A;

1-palmitoyl-16-thiophenyl-15,16-dehydro-17-ketomarcfortine A;

1-(4-morpholinocarbonyl)-16-thiophenyl-15,16-dehydro-17-ketomarcfortine A.;

1-palmitoyl-16-thiophenyl-15,16-dehydro-17-ketomarcfortine D;

1-(4-morpholinocarbonyl)-16-thiophenyl-15,16-dehydro-17-ketomarcfortine D;

16-thiophenyl-15,16-dehydro-17-ketodroxymarcfortine D;

1-acetoxymethyl-16-thiophenyl-15,16-dehydro-17-ketomarcfortine D;

1-diethoxyphosphoryl-16-thiophenyl-15,16-dehydro-17-ketomarcfortine D;

1-dimethylsulfamoyl-16-thiophenyl-15,16-dehydro-17-ketomarcfortine D;

1-cyclopropylcarbonyl-16-thiophenyl-15,16-dehydro-17-ketomarcfortine D;

2-bicyclo[2.2.1]heptanoyl-16-thiophenyl-15,16-dehydro-17-ketomarcfortine D;

1-(1-piperidinyl)thiocarbonyl-16-thiophenyl-15,16-dehydro-17-ketomarcfortine D;

1-succinoyl-16-thiophenyl-15,16-dehydro-17-ketomarcfortine D;

1-(4-morpholinosulfenyl)-16-thiophenyl-15,16-dehydro-17-ketomarcfortine D;

1-(2,4-dinitrobenzenesulfenyl)-16-thiophenyl-15,16-dehydro-17-ketomarcfortine D;

24-propoxy-24,25-dihydro-16-thiophenyl-15,16-dehydro-17-ketomarcfortine D;

1-(p-toluenesulfonyl)-16-thiophenyl-15,16-dehydro-17-ketomarcfortine D;

1-acetyl-16-thiophenyl-15,16-dehydro-17-ketomarcfortine D;

1-methyl-16-thiophenyl-15,16-dehydro-17-ketomarcfortine D;

1-benzyl-16-thiophenyl-15,16-dehydro-17-ketomarcfortine D;

1-dimethylcarbamoyl-16-thiophenyl-15,16-dehydro-17-ketomarcfortine D; or 1-methoxycarbonyl-16-thiophenyl-15,16-dehydro-17-ketomarcfortine D.

16-thiophenyl-15,16-dehydro-17-ketomarcfortine A;

1-acetoxymethyl-16-thiophenyl-15,16-dehydro-17-ketomarcfortine A;

1-diethoxyphosphoryl-16-thiophenyl-15,16-dehydro-17-ketoxymarcfortine A;

1-dimethylsulfamoyl-16-thiophenyl-15,16-dehydro-17-ketomarcfortine A;

1-cyclopropylcarbonyl-16-thiophenyl-15,16-dehydro-17-ketomarcfortine A;

2-bicyclo [2.2.1]heptanoyl-16-thiophenyl-15,16-dehydro-17-ketomarcfortine A.;

1-(1-piperidinyl)thiocarbonyl-16-thiophenyl-15,16-dehydro-17-ketomarcfortine A;

1-succinoyl-16-thiophenyl-15,16-dehydro-17-ketomarcfortine A;

1-(4morpholinosulfenyl)-16-thiophenyl-15,16-dehydro-17-ketomarcfortine A;

1-(2,4-dinitrobenzenesulfenyl)-16-thiophenyl-15,16-dehydro-17-ketomarcfortine A;

24-propoxy-24,25-dihydro-16-thiophenyl-15,16-dehydro-17-ketomarcfortine A;

1-(p-toluenesulfonyl)-16-thiophenyl-15,16-dehydro-17-ketomarcfortine A;

1-acetyl-16-thiophenyl-15,16-dehydro-17-ketomarcfortine A;

1-methyl-16-thiophenyl-15,16-dehydro-17-ketomarcfortine A;

1-benzyl-16-thiophenyl-15,16-dehydro-17-ketomarcfortine A;

1-dimethylcarbamoyl-16-thiophenyl-15,16-dehydro-17-ketomarcfortine A;

1-methoxycarbonyl-16-thiophenyl-15,16-dehydro-17-ketomarcfortine A;

16-thiophenyl-15,16-dehydro-17-ketomarcfortine B;

24,25-dihydro-16-thiophenyl-15,16-dehydro-17-ketomarcfortine B;

24-methoxy-24,25-dihydro-16-thiophenyl-15,16-dehydro-17-ketomarcfortine B;

1-(p-toluenesulfonyl)-16-thiophenyl-15,16-dehydro-17-ketomarcfortine B;

1-ethyl-16-thiophenyl-15,16-dehydro-17-ketomarcfortine B;

1-benzyl-16-thiophenyl-15,16-dehydro-17-ketomarcfortine B;

18a-ethyl-16-thiophenyl-15,16-dehydro-17-ketomarcfortine B;

18a-benzyl-16-thiophenyl-15,16-dehydro-17-ketomarcfortine B;

18a-methoxyethoxymethyl-16-thiophenyl-15,16-dehydro-17-ketomarcfortine B;

18a-allyl-16-thiophenyl-15,16-dehydro-17-ketomarcfortine B;

18a-propargyl-16-thiophenyl-15,16-dehydro-17-ketomarcfortine B;

18a-ethyl-24-methoxy-24,25-dihydro-16-thiophenyl-15,16-dehydro-17-ketomarcfortine B;

1,18a-bis-ethyl-16-thiophenyl-15,16-dehydro-17-ketomarcfortine B;

1,18a-bis-benzyl-16-thiophenyl-15,16-dehydro-17-ketomarcfortine B;

18a-ethyl-24-methoxy-16-thiophenyl-15,16-dehydro-17-ketomarcfortine B;

1-(2,4-dinitrobenzene sulfonyl)-18a-ethyl-24-methoxy-24,25-dihydro-14α-hydroxymarcfortine B;

18a-ethyl-24,25 dihydro-16-thiophenyl-15,16-dehydro-17-ketomarcfortine B;

24,25 dihydro-16-thiophenyl-15,16-dehydro-17-ketomarcfortine C;

1-(p-bromobenzene sulfonyl)-16-thiophenyl-15,16-dehydro-17-ketomarcfortine C;

1-propionyl-16-thiophenyl-15,16-dehydro-17-ketomarcfortine C;

1-propyl-16-thiophenyl-15,16-dehydro-17-ketomarcfortine C;

1-benzyl-16-thiophenyl-15,16-dehydro-17-ketomarcfortine C;

18a-propyl-16-thiophenyl-15,16-dehydro-17-ketomarcfortine C;

18a-benzyl-16-thiophenyl-15,16-dehydro-17-ketomarcfortine C;

18a-methoxyethoxymethyl-16-thiophenyl-15,16-dehydro-17-ketomarcfortine C;

18-allyl-16-thiophenyl-15,16-dehydro-17-ketomarcfortine C;

18a-propargyl-16-thiophenyl-15,16-dehydro-17-ketomarcfortine C;

1,18a-bis-propyl-16-thiophenyl-15,16-dehydro-17-ketomarcfortine C;

1,18a-bis-benzyl-16-thiophenyl-15,16-dehydro-17-ketomarcfortine C;

16-thiophenyl-15,16-dehydro-17-ketomarcfortine C;

1-(4-carbethoxy-1,3-thiazolidinin-3-yl)carbonyl-16-thiophenyl-15,16-dehydro-17-ketomarcfortine A;

1-palmitoyl-16-thiophenyl-15,16-dehydro-17-ketomarcfortine A;

1-(4-morpholinocarbonyl)-16-thiophenyl-15,16-dehydro-17-ketomarcfortine A;

1-palmitoyl-16-thiophenyl-15,16-dehydro-17-ketomarcfortine D;

1-(4-morpholinocarbonyl)-16-thiophenyl-15,16-dehydro-17-ketomarcfortine D;

16-thiophenyl-15,16-dehydro-17-ketodroxymarcfortine D;

1-acetoxymethyl-16-thiophenyl-15,16-dehydro-17-ketomarcfortine D;

1-diethoxyphosphoryl-16-thiophenyl-15,16-dehydro-17-ketomarcfortine D;

1-dimethylsulfamoyl-16-thiophenyl-15,16-dehydro-17-ketomarcfortine D;

1-cyclopropylcarbonyl-16-thiophenyl-15,16-dehydro-17-ketomarcfortine D;

2-bicyclo[2.2.1]heptanoyl-16-thiophenyl-15,16-dehydro-17-ketomarcfortine D.

1-(1-piperidinyl)thiocarbonyl-16-thiophenyl-15,16-dehydro-17-ketomarcfortine D;

1-succinoyl-16-thiophenyl-15,16-dehydro-17-ketomarcfortine D;

1-(4-morpholinosulfenyl)-16-thiophenyl-15,16-dehydro-17-ketomarcfortine D;

1-(2,4-dinitrobenzenesulfenyl)-16-thiophenyl-15,16-dehydro-17-ketomarcfortine D;

24-propoxy-24,25-dihydro-16-thiophenyl-15,16-dehydro-17-ketomarcfortine D;

1-(p-toluenesulfonyl)-16-thiophenyl-15,16-dehydro-17-ketomarcfortine D;

1-acetyl-16-thiophenyl-15,16-dehydro-17-ketomarcfortine D;

1-methyl-16-thiophenyl-15,16-dehydro-17-ketomarcfortine D;

1-benzyl-16-thiophenyl-15,16-dehydro-17-ketomarcfortine D;

1-dimethylcarbamoyl-16-thiophenyl-15,16-dehydro-17-ketomarcfortine D; or 1-methoxycarbonyl-16-thiophenyl-15,16-dehydro-17-ketomarcfortine D.

14α-hydroxy-14β-methyl-15α-methyl-17-ketomarcfortine A;

1-acetoxymethyl-14α-hydroxy-141-methyl-15-methyl-17-ketomarcfortine A;

1-diethoxyphosphoryl-14α-hydroxy-14β-methyl-15α-methyl-17-ketoxymarcfortine A;

1-dimethylsulfamoyl-14α-hydroxy-14β-methyl-15α-methyl-17-ketomarcfortiine A;

1-cyclopropylcarbonyl-14α-hydroxy-14β-methyl-15α-methyl-17-ketomarcfortine A;

2-bicyclo[2.2.1]heptanoyl-14α-hydroxy-141-methyl-15α-methyl-17-ketomarcfortine A;

1-(1-piperidinyl)thiocarbonyl-14α-hydroxy-14β-methyl-15α-methyl-17-ketomarcfortine A;

1-succinoyl-14α-hydroxy-14β-methyl-15α-methyl-17-ketomarcfortine A;

1-(4-morpholinosulfenyl)-14α-hydroxy-14β-methyl-15α-methyl-17-ketomarcfortine A;

1-(2,4-dinitrobenzenesulfenyl)-14α-hydroxy-14β-methyl-15α-methyl-17-ketomarcfortine A;

24-propoxy-24,25-dihydro-14α-hydroxy-14β-methyl-15α-methyl-17-ketomarcfortine A;

1-(p-toluenesulfonyl)-14α-hydroxy-14β-methyl-15α-methyl-17-ketomarcfortine A;

1-acetyl-14α-hydroxy-14β-methyl-15α-methyl-17-ketomarcfortine A;

1-methyl-14α-hydroxy-14β-methyl-15α-methyl-17-ketomarcfortine A;

1-benzyl-14α-hydroxy-14β-methyl-15α-methyl-17-ketomarcfortine A;

1-dimethylcarbamoyl-14α-hydroxy-14β-methyl-15α-methyl-17-ketomarcfortine A;

1-methoxycarbonyl-14α-hydroxy-14β-methyl-15α-methyl-17-ketomarcfortine A;

14α-hydroxy-14β-methyl-15α-methyl-17-ketomarcfortine B;

24,25-dihydro-14(α-hydroxy-14β-methyl-15α-methyl-17-ketomarcfortine B;

24-methoxy-24,25-dihydro-14α-hydroxy-14β-methyl-15α-methyl-17-ketomarcfortine B;

1-(p-toluenesulfonyl)-14α-hydroxy-14β-methyl-15α-methyl-17-ketomarcfortine B;

1-ethyl-14α-hydroxy-14β-methyl-15α-methyl-17-ketomarcfortine B;

1-benzyl-14α-hydroxy-14β-methyl-15α-methyl-17-ketomarcfortine B;

18a-ethyl-14α-hydroxy-14β-methyl-15α-methyl-17-ketomarcfortine B;

18a-benzyl-14α-hydroxy-14β-methyl-15α-methyl-17-ketomarcfortine B;

18a-methoxyethoxymethyl-14α-hydroxy-14β-methyl-15α-methyl-17-ketomarcfortine B;

18a-allyl-14α-hydroxy-14β-methyl-15α-methyl-17-ketomarcfortine B;

18a-propargyl-14α-hydroxy-14β-methyl-15α-methyl-17-ketomarcfortine B;

18a-ethyl-24-methoxy-24,25-dihydro-14α-hydroxy-14β-methyl-15α-methyl-17-ketomarcfortine B;

1,18a-bis-ethyl-14α-hydroxy-14β-methyl-15α-methyl-17-ketomarcfortine B;

1,18a-bis-benzyl-14α-hydroxy-14β-methyl-15α-methyl-17-ketomarcfortine B;

18a-ethyl-24-methoxy-14α-hydroxy-14β-methyl-15α-methyl-17-ketomarcfortine B;

1-(2,4-dinitrobenzene sulfonyl)-18a-ethyl-24-methoxy-24,25-dihydro-14α-hydroxymarcfortine B;

18a-ethyl-24,25 dihydro-14α-hydroxy-14β-methyl-1 Sa-methyl-17-ketomarcfortine B;

24,25 dihydro-14α-hydroxy-14β-methyl-15α-methyl-17-ketomarcfortine C;

1-(p-bromobenzene sulfonyl)-14α-hydroxy-14β-methyl-15α-methyl-17-ketomarcfortine C;

1-propionyl-14α-hydroxy-14β-methyl-15α-methyl-17-ketomarcfortine C;

1-propyl-14α-hydroxy-14β-methyl-15α-methyl-17-ketomarcfortine C;

1-benzyl-14α-hydroxy-14β-methyl-15α-methyl-17-ketomarcfortine C;

18a-propyl-14α-hydroxy-14β-methyl-15α-methyl-17-ketomarcfortine C;

18a-benzyl-14α-hydroxy-1β,-methyl-15α-methyl-17-ketomarcfortine C;

18a-methoxyethoxymethyl-14α-hydroxy-14β-methyl-15α-methyl-17-ketomar-fortine C;

18-allyl-14α-hydroxy-14β-methyl-15α-methyl-17-ketomarcfortine C;

18a-propargyl-14α-hydroxy-14β-methyl-15α-methyl-17-ketomarcfortine C;

1,18a-bis-propyl-14α-hydroxy-14β-methyl-15α-methyl-17-ketomarcfortine C:

1,18a-bis-benzyl-14c-hydroxy-140-methyl-15a-methyl-17-ketomarcfortine C.

14α-hydroxy-14β-methyl-15α-methyl-17-ketomarcfortine C;

1-(4-carbethoxy-1,3-thiazolidinin-3-yl)carbonyl-14α-hydroxy-14β-methyl-15α-methyl-17-ketomarcfortine A;

1-palmitoyl-14α-hydroxy-14β-methyl-15α-methyl-17-ketomarcfortine A;

1-(4-morpholinocarbonyl)-14α-hydroxy-14β-methyl-15α-methyl-17-ketomarcfortine A;

1-palmitoyl-14α-hydroxy-14β-methyl-15α-methyl-17-ketomarcfortine D;

1-(4-morpholinocarbonyl)-14α-hydroxy-14β-methyl-15α-methyl-7-ketomarcfortine D;

14α-hydroxy-14β-methyl-15α-methyl-17-ketomarcfortine D;

1-acetoxymethyl-14α-hydroxy-14β-methyl-15α-methyl-17-ketomarcfortine D;

1-diethoxyphosphoryl-14α-hydroxy-14β-methyl-15α-methyl-17-ketomarcfortine D;

1-dimethylsulfamoyl-14α-hydroxy-14β-methyl-15α-methyl-17-ketomarcfortine D;

1-cyclopropylcarbonyl-14α-hydroxy-14β-methyl-15α-methyl-17-ketomarcfortine D;

2-bicyclo[2.2.1]heptanoyl-14α-hydroxy-14β-methyl-15α-methyl-17-ketomarcfortine D;

1-(1-piperidinyl)thiocarbonyl-14α-hydroxy-14β-methyl-15α-methyl-17-ketomarcfortine D;

1-succinoyl-14α-hydroxy-14β-methyl-15α-methyl-17-ketomarcfortine D;

1-(4-morpholinosulfenyl)-14α-hydroxy-14β-methyl-15α-methyl-17-ketomarcfortine D;

1-(2,4-dinitrobenzenesulfenyl)-14α-hydroxy-14β-methyl-15α-methyl-17-ketomarcfortine D;

24-propoxy-24,25-dihydro-14α-hydroxy-14β-methyl-15α-methyl-17-ketomacfortine D;

1-(p-toluenesulfonyl)-14α-hydroxy-14β-methyl-15a-methyl-17-ketomarcfortine D;

1-acetyl-14α-hydroxy-14β-methyl-15α-methyl-17-ketomarcfortine D;

1-methyl-14α-hydroxy-14β-methyl-5α-methyl-17-ketomarcfortine D;

1-benzyl-14α-hydroxy-14β-methyl-15α-methyl-17-ketomarcfortine D;

1-dimethylcarbamoyl-14α-hydroxy-14β-methyl-15α-methyl-17-ketomarcfortine D;

1-methoxycarbonyl-14α-hydroxy-14β-methyl-15α-methyl-17-ketomarcfortine D;

14α-hydroxy-15α-methyl-17-ketomarcfortine A;

1-acetoxymethyl-14α-hydroxy-15α-methyl-17-ketomarcfortine A;

1-diethoxyphosphoryl-14α-hydroxy-15α-methyl-17-ketoxymarcfortine A;

1-dimethylsulfamoyl-14α-hydroxy-15α-methyl-17-ketomarcfortine A;

1-cyclopropylcarbonyl-14α-hydroxy-15α-methyl-17-ketomarcfortine A;

2-bicyclo[2.2.1]heptanoyl-14α-hydroxy-15α-methyl-17-ketomarcfortine A;

1-(1-piperidinyl)thiocarbonyl-14α-hydroxy-15α-methyl-17-ketomarcfortine A;

1-succinoyl-14α-hydroxy-15α-methyl-17-ketomarcfortine A;

1-(4-morpholinosulfenyl)-14α-hydroxy-15α-methyl-17-ketomarcfortine A;

1-(2,4-dinitrobenzenesulfenyl)-14α-hydroxy-15α-methyl-17-ketomarcfortine A;

24-propoxy-24,25-dihydro-14α-hydroxy-15α-methyl-17-ketomarcfortine A;

1-(p-toluenesulfonyl)-14α-hydroxy-15α-methyl-17-ketomarcfortine A;

1-acetyl-14α-hydroxy-15α-methyl-17-ketomarcfortine A;

1-methyl-14α-hydroxy-15α-methyl-17-ketomarcfortine A;

1-benzyl-14α-hydroxy-15α-methyl-17-ketomarcfortine A;

1-dimethylcarbamoyl-14α-hydroxy-15α-methyl-17-ketomarcfortine A;

1-methoxycarbonyl-14α-hydroxy-15α-methyl-17-ketomarcfortine A;

14α-hydroxy-15α-methyl-17-ketomarcfortine B;

24,25-dihydro-14α-hydroxy-15α-methyl-17-ketomarcfortine B;

24-methoxy-24,25-dihydro-14α-hydroxy-15α-methyl-17-ketomarcfortine B;

1-(p-toluenesulfonyl)-14α-hydroxy-15α-methyl-17-ketomarcfortine B;

1-ethyl-14α-hydroxy-15α-methyl-17-ketomarcfortine B;

1-benzyl-14α-hydroxy-15α-methyl-17-ketomarcfortine B;

18a-ethyl-14α-hydroxy-15α-methyl-17-ketomarcfortine B;

18a-benzyl-14α-hydroxy-15α-methyl-17-ketomarcfortine B;

18a-methoxyethoxymethyl-14α-hydroxy-15α-methyl-17-ketomarcfortine B;

18a-allyl-14α-hydroxy-15α-methyl-17-ketomarcfortine B;

18a-propargyl-14α-hydroxy-15α-methyl-17-ketomarcfortine B;

18a-ethyl-24-methoxy-24,25-dihydro-14α-hydroxy-15α-methyl-17-ketomarcfortine B;

1,18a-bis-ethyl-14α-hydroxy-15α-methyl-17-ketomarcfortine B;

1,18a-bis-benzyl-14α-hydroxy-15α-methyl-17-ketomarcfortine B;

18a-ethyl-24-methoxy-14α-hydroxy-15α-methyl-17-ketomarcfortine B;

1-(2,4-dinitrobenzene sulfonyl)-18a-ethyl-24-methoxy-24,25-dihydro-14α-hydroxymarcfortine B;

18a-ethyl-24,25-dihydro-14α-hydroxy-15α-methyl-17-ketomarcfortine B;

24,25 dihydro-14α-hydroxy-15α-methyl-17-ketomarcfortine C;

1-(p-bromobenzene sulfonyl)-14α-hydroxy-15α-methyl-17-ketomarcfortine C;

1-propionyl-14α-hydroxy-15α-methyl-17-ketomarcfortine C;

1-propyl-14α-hydroxy-15α-methyl-17-ketomarcfortine C;

1-benzyl-14α-hydroxy-15α-methyl-17-ketomarcfortine C;

18a-propyl-14α-hydroxy-15α-methyl-17-ketomarcfortine C;

18a-benzyl-14α-hydroxy-15α-methyl-17-ketomarcfortine C;

18a-methoxyethoxymethyl-14α-hydroxy-15α-methyl-17-ketomarcfortine C;

18-allyl-14α-hydroxy-15α-methyl-17-ketomarcfortine C;

18a-propargyl-14α-hydroxy-15α-methyl-17-ketomarcfortine C;

1,18a-bis-propyl-14α-hydroxy-15α-methyl-17-ketomarcfortine C;

1,18a-bis-benzyl-14α-hydroxy-15α-methyl-17-ketomarcfortine C;

14α-hydroxy-15α-methyl-17-ketomarcfortine C;

1-(4-carbethoxy-1,3-thiazolidinin-3-yl)carbonyl-14α-hydroxy-15α-methyl-17-ketomarcfortine A;

1-palmitoyl-14α-hydroxy-15α-methyl-17-ketomarcfortine A;

1-(4-morpholinocarbonyl)-14α-hydroxy-15α-methyl-17-ketomarcfortine A;

1-palmitoyl-14α-hydroxy-15α-methyl-17-ketomarcfortine D;

1-(4-morpholinocarbonyl)-14α-hydroxy-15α-methyl-17-ketomarcfortine D;

14α-hydroxy-15α-methyl-17-ketomarcfortine D;

1-acetoxymethyl-14α-hydroxy-15α-methyl-17-ketomarcfortine D;

1-diethoxyphosphoryl-14α-hydroxy-15α-methyl-17-ketomarcfortine D;

1-dimethylsulfamoyl-14α-hydroxy-15α-methyl-17-ketomarcfortine D;

1-cyclopropylcarbonyl-14α-hydroxy-15α-methyl-17-ketomarcfortine D;

2-bicyclo[2.2.1]heptanoyl-14α-hydroxy-15α-methyl-17-ketomarcfortine D;

1-(1-piperidinyl)thiocarbonyl-14α-hydroxy-15α-methyl-17-ketomarcfortine D;

1-succinoyl-14α-hydroxy-15α-methyl-17-ketomarcfortine D;

1-(4-morpholinosulfenyl)-14α-hydroxy-15α-methyl-17-ketomarcfortine D;

1-(2,4-dinitrobenzenesulfenyl)-14α-hydroxy-15α-methyl-17-ketomarcfortine D;

24-propoxy-24,25-dihydro-14α-hydroxy-15α-methyl-17-ketomarcfortine D;

1-(p-toluenesulfonyl)-14α-hydroxy-15α-methyl-17-ketomarcfortine D;

1-acetyl-14α-hydroxy-15α-methyl-17-ketomarcfortine D;

1-methyl-14α-hydroxy-15α-methyl-17-ketomarcfortine D;

1-benzyl-14α-hydroxy-15α-methyl-17-ketomarcfortine D;

1-dimethylcarbamoyl-14α-hydroxy-15α-methyl-17-ketomarcfortine D;

1-methoxycarbonyl-14α-hydroxy-15α-methyl-17-ketomarcfortine D;

15α-methyl-14,17-diketomarcfortine A;

1-acetoxymethyl-15α-methyl-14,17-diketomarcfortine A;

1-diethoxyphosphoryl-15α-methyl-14,17-diketoxymarcfortine A;

1-dimethylsulfamoyl-15α-methyl-14,17-diketomarcfortine A;

1-cyclopropylcarbonyl-15α-methyl-14,17-diketomarcfortine A;

2-bicyclo[2.2.1]heptanoyl-15α-methyl-14,17-diketomarcfortine A;

1-(1-piperidinyl)thiocarbonyl-15α-methyl-14,17-diketomarcfortine A;

1-succinoyl-15α-methyl-14,17-diketomarcfortine A;

1-(4-morpholinosulfenyl)-15α-methyl-14,17-diketomarcfortine A;

1-(2,4-dinitrobenzenesulfenyl)-15α-methyl-14,17-diketomarcfortine A;

24-propoxy-24,25-dihydro-15 -methyl-14,17-diketomarcfortine A;

1-(p-toluenesulfonyl)-15α-methyl-14,17-diketomarcfortine A;

1-acetyl-15α-methyl-14,17-diketomarcfortine A;

1-methyl-15α-methyl-14,17-diketomarcfortine A;

1-benzyl-15α-methyl-14,17-diketomarcfortine A;

1-dimethylcarbamoyl-15α-methyl-14,17-diketomarcfortine A;

1-methoxycarbonyl-15α-methyl-14,17-diketomarcfortine A;

15α-methyl-14,17-diketomarcfortine B;

24,25-dihydro-15α-methyl-14,17-diketomarcfortine B;

24-methoxy-24,25-dihydro-15α-methyl-14,17-diketomarcfortine B;

1-(p-toluenesulfonyl)-15α-methyl-14,17-diketomarofortine B;

1-ethyl-15α-methyl-14,17-diketomarcfortine B;

1-benzyl-15α-methyl-14,17-diketomarcfortine B;

18a-ethyl-15α-methyl-14,17-diketomarcfortine B;

18a-benzyl-15α-methyl-14,17-diketomarcfortine B;

18a-methoxyethoxymethyl-15α-methyl-14,17-diketomarcfortine B;

18a-allyl-15α-methyl-14,17-diketomarcfortine B;

18a-propargyl-15α-methyl-14,17-diketomarcfortine B;

18a-ethyl-24-methoxy-24,25-dihydro-15α-methyl-14,17-diketomarcfortine E;

1,18a-bis-ethyl-15α-methyl-14,17-diketomarcfortine B;

1,18a-bis-benzyl-15α-methyl-14,17-diketomarcfortine B;

18a-ethyl-24-methoxy-15α-methyl-14,17-diketomarcfortine B;

1-(2,4-dinitrobenzene sulfonyl)-18a-ethyl-24-methoxy-24,25-dihydro-14α-hydroxymarcfortine B;

18a-ethyl-24,25-dihydro-15α-methyl-14,17-diketomarcfortine B;

24,25 dihydro-15α-methyl-14,17-diketomarcfortine C;

1-(p-bromobenzene sulfonyl)-15α-methyl-14,17-diketomarcfortine C;

1-propionyl-15α-methyl-14,17-diketomarcfortine C;

1-propyl-15α-methyl-14,17-diketomarcfortine C;

1-benzyl-15α-methyl-14,17-diketomarcfortine C;

18a-propyl-15α-methyl-14,17-diketomarcfortine C;

18a-benzyl-15α-methyl-14,17-diketomarcfortine C;

18a-methoxyethoxymethyl-15α-methyl-14,17-diketomarcfortine C;

18-allyl-15α-methyl-14,17-diketomarcfortine C;

18a-propargyl-15α-methyl-14,17-diketomarcfortine C;

1,18a-bis-propyl-15α-methyl-14,17-diketomarcfortine C;

1,18a-bis-benzyl-15α-methyl-14,17-diketomarcfortine C;

15α-methyl-14,17-diketomarcfortine C;

1-(4-carbethoxy-1,3-thiazolidinin-3-yl)carbonyl-15α-methyl-14,17-diketomarcfortine A;

1-palmitoyl-15α-methyl-14,17-diketomarcfortine A;

1-(4-morpholinocarbonyl)-15α-methyl-14,17-diketomarcfortine A;

1-palmitoyl-15α-methyl-14,17-diketomarcfortine D;

1-(4-morpholinocarbonyl)-15α-methyl-14,17-diketomarcfortine D;

15α-methyl-14,17-diketomarcfortine D;

1-acetoxymethyl-15α-methyl-14,17-diketomarcfortine D;

1-diethoxyphosphoryl-15α-methyl-14,17-diketomarcfortine D;

1-dimethylsulfamoyl-15α-methyl-14,17-diketomarcfortine D;

1-cyclopropylcarbonyl-15α-methyl-14,17-diketomarcfortine D;

2-bicyclo[2.2.1]heptanoyl-15α-methyl-14,17-diketomarcfortine D;

1-(1-piperidinyl)thiocarbonyl-15α-methyl-14,17-diketomarcfortine D;

1-succinoyl-15α-methyl-14,17-diketomarcfortine D;

1-(4-morpholinosulfenyl)-15α-methyl-14,17-diketomarcfortine D;

1-(2,4-dinitrobenzenesulfenyl)-15α-methyl-14,17-diketomarcfortine D;

24-propoxy-24,25-dihydro-15α-methyl-14,17-diketomarcfortine D;

1-(p-toluenesulfonyl)-15α-methyl-14,17-diketomarcfortine D;

1-acetyl-15α-methyl-14,17-diketomarcfortine D;

1-methyl-15α-methyl-14,17-diketomarcfortine D;

1-benzyl-15α-methyl-14,17-diketomarcfortine D;

1-dimethylcarbamoyl-15α-methyl-14,17-diketomarcfortine D;

1-methoxycarbonyl-15α-methyl-14,17-diketomarcfortine D;

14,15-dehydro-16,17-diketomarcfortine A;

1-acetoxymethyl-14,15-dehydro-16,17-diketomarcfortine A;

1-diethoxyphosphoryl-14,15-dehydro-16,17-diketoxymarcfortine A;

1-dimethylsulfamoyl-14,15-dehydro-16,17-diketomarcfortine A;

1-cyclopropylcarbonyl-14,15-dehydro-16,17-diketomarcfortine A;

2-bicyclo[2.2.1]heptanoyl-14,15-dehydro-16,17-diketomarcfortine A;

1-(1-piperidinyl)thiocarbonyl-14,15-dehydro-16,17-diketomarcfortine A;

1-succinoyl-14,15-dehydro-16,17-diketomarcfortine A;

1-(4-morpholinosulfenyl)-14,15-dehydro-16,17-diketomarcfortine A;

1-(2,4-dinitrobenzenesulfenyl)-14,15-dehydro-16,17-diketomarcfortine A;

24-propoxy-24,25-dihydro-14,15-dehydro-16,17-diketomarcfortine A;

1-(p-toluenesulfonyl)-14,15-dehydro-16,17-diketomarcfortine A;

1-acetyl-14,15-dehydro-16,17-diketomarcfortine A;

1-methyl-14,15-dehydro-16,17-diketomarcfortine A;

1-benzyl-14,15-dehydro-16,17-diketomarcfortine A;

1-dimethylcarbamoyl-14,15-dehydro-16,17-diketomarcfortine A;

1-methoxycarbonyl-14,15-dehydro-16,17-diketomarcfortine A;

14,15-dehydro-16,17-diketomarcfortine B;

24,25-dihydro-14,15-dehydro-16,17-diketomarcfortine B;

24-methoxy-24,25-dihydro-14,15-dehydro-16,17-diketomarcfortine B;

1-(p-toluenesulfonyl)-14,15-dehydro-16,17-diketomarcfortine B;

1-ethyl-14,15-dehydro-16,17-diketomarcfortine B;

1-benzyl-14,15-dehydro-16,17-diketomarcfortine B;

18a-ethyl-14,15-dehydro-16,17-diketomarcfortine B;

18a-benzyl-14,15-dehydro-16,17-diketomarcfortine B;

18a-methoxyethoxymethyl-14,15-dehydro-16,17-diketomarcfortine B;

18a-allyl-14,15-dehydro-16,17-diketomarcfortine B;

18a-propargyl-14,15-dehydro-16,17-diketomarcfortine B;

18a-ethyl-24-methoxy-24,25-dihydro-14,15-dehydro-16,17-diketomarcfortine E.;

1,18a-bis-ethyl-14,15-dehydro-16,17-diketomarcfortine B;

1,18a-bis-benzyl-14,15-dehydro-16,17-diketomarcfortine B;

18a-ethyl-24-methoxy-14,15-dehydro-16,17-diketomarcfortine B;

1-(2,4-dinitrobenzene sulfonyl)-18a-ethyl-24-methoxy-24,25-dihydro-14α-hydroxymarcfortine B;

18a-ethyl-24,25 dihydro-14,15-dehydro-16,17-diketomarcfortine B;

24,25 dihydro-14,15-dehydro-16,17-diketomarcfortine C;

1-(p-bromobenzene sulfonyl)-14,15-dehydro-16,17-diketomarcfortine C;

1-propionyl-14,15-dehydro-16,17-diketomarcfortine C;

1-propyl-14,15-dehydro-16,17-diketomarcfortine C;
1-benzyl-14,15-dehydro-16,17-diketomarcfortine C;
18a-propyl-14,15-dehydro-16,17-diketomarcfortine C;
18a-benzyl-14,15-dehydro-16,17-diketomarcfortine C;
18a-methoxyethoxymethyl-14,15-dehydro-16,17-diketornarcfortine C;
18-allyl-14,15-dehydro-16,17-diketomarcfortine C;
18a-propargyl-14,15-dehydro-16,17-diketomarcfortine C;
1,18a-bis-propyl-14,15-dehydro-16,17-diketomarcfortine C;
1,18a-bis-benzyl-14,15-dehydro-16,17-diketomarcfortine C;
14,15-dehydro-16,17-diketomarcfortine C;
1-(4-carbethoxy-1,3-thiazolidinin-3-yl)carbonyl-14,15-dehydro-16,17-diketomarcfortine A;
1-palmitoyl-14,15-dehydro-16,17-diketomarcfortine A;
1-(4-morpholinocarbonyl)-14,15-dehydro-16,17-diketomarcfortine A;
1-palmitoyl-14,15-dehydro-16,17-diketomarcfortine D;
1-(4-morpholinocarbonyl)-14,15-dehydro-16,17-diketomarcfortine D;
14,15-dehydro-16,17-diketomarcfortine D;
1-acetoxymethyl-14,15-dehydro-16,17-diketomarcfortine D;
1-diethoxyphosphoryl-14,15-dehydro-16,17-diketomarcfortine D;
1-dimethylsulfamoyl-14,15-dehydro-16,17-diketomarcfortine D;
1-cyclopropylcarbonyl-14,15-dehydro-16,17-diketomarcfortine D;
2-bicyclo[2.2.1]heptanoyl-14,15-dehydro-16,17-diketomarcfortine D;
1-(1-piperidinyl)thiocarbonyl-14,15-dehydro-16,17-diketomarcfortine D;
1-succinoyl-14,15-dehydro-16,17-diketomarcfortine D;
1-(4-morpholinosulfenyl)-14,15-dehydro-16,17-diketomarcfortine D;
1-(2,4-dinitrobenzenesulfenyl)-14,15-dehydro-16,17-diketomarcfortine D;
24-propoxy-24,25-dihydro-14,15-dehydro-16,17-diketomarcfortine D;
1-(p-toluenesulfonyl)-14,15-dehydro-16,17-diketomarcfortine D;
1-acetyl-14,15-dehydro-16,17-diketomarcfortine D;
1-methyl-14,15-dehydro-16,17-diketomarcfortine D;
1-benzyl-14,15-dehydro-16,17-diketomarcfortine D;
1-dimethylcarbamoyl-14,15-dehydro-16,17-diketomarcfortine D; and
1-methoxycarbonyl-14,15-dehydro-16,17-diketomarcfortine D.

General procedures for the preparation of heteroaromatic N-oxides can be found in Chapter II of "Chemistry of the Heterocyclic N-Oxides", A. R. Katritzky and J. M. Lagowski, published 1971 Academic Press (Vol. 19 of ORGANIC CHEMISTRY—A Series of Monographs). Typically the N-oxide is formed by reaction with a percarboxylic acid in an appropriate solvent. Most suitably an aromatic peracid in a non-polar solvent is used, since the reaction may usually be carried out at room temperature. Suitable aromatic peracids include perbenzoic acid, chloroperbenzoic acid and perphthalic acid.

PREPARATION OF STARTING MATERIAL

N-18a substituted marcfortines B and C and C24–C25 modified marcfortines are readily prepared by procedures given in U.S. Pat. No. 4,923,867, the disclosure of which is incorporated herein by reference.

Marcfortines A, B and C are isolated, along with the previously known roquefortine, as fungal metabolites of *Penicillium roqueforti* using standard fermentation and isolation techniques. The isolation, as well as the analytical and structural characteristics of marcfortine A, are described in detail in Polonsky et al *Journal of the Chemical Society Chemical Communications* 1980, 601–602. The isolation, as well as the analytical and structural characteristics of marcfortines B and C, are described in detail in Polonsky et al *Tetrahedron Letters* 1981, 22, 1977–1980.

Alternatively, and more preferably, Marcfortines A, C, and D may be isolated from Penicillium sp. UC7780 (strain number in Upjohn Culture Collection, UC 7780, The Upjohn Company, Kalamazoo, Mich.). This strain was isolated from a soil sample collected in Illinois, deposited in the U.S. Department of Agriculture patent culture collection in Peoria, Ill. and given the accession number NRRL 18887. To further characterize the fungus a taxonomy study was done following the methods and materials described by I. John Pitt, The Genus Penicillium, Academic Press, London, (1979). Spore and hyphae surfaces were examined by scanning electron microscopy according to the methods of Dietz, A. and Matthews, J. Appl. Microbiology 18:694–696 (1969). Intact conidiophores are visualized by light microscopy [A. H. S. Onions et al., Smith's Introduction to Industrial Mycology, John Wiley and Sons, New York, pp 301–302 (1979)] after slide culture(s) are prepared: A glass petri dish containing glass beads, microscope slide, and coverslip are sterilized. A small block of potato dextrose agar is placed on the slide and inoculated on four sides with the fungus culture. The coverslip is set on the inoculated agar block and sterile water added to maintain moisture. The chamber is incubated for six days at 24° C. A slide is prepared by removing the coverslip and placing it on a drop of lactophenol cotton blue stain.

The characteristics of Penicillium sp. UC 7780 (NRRL 18887) are as follows:

Morphology—a biverticillate penicillus (two branch points between conidium and stipe). These branches (metulae) support the phialides or conidia bearing structures. Conidiophores (approximately 35 μm) terminated in verticils of 2–5 (10–14 μm) metulae. Phialides were ampulliform (like an ancient Greek wine jar) in verticils of 2–5 (7 μm). Conidia were smooth and spheroidal (2 μm) typically appearing in long columns. The stipe walls were smooth.

The culture was inoculated onto three petri dishes of Czapek yeast agar (CYA), one being 6 cm in diameter and one each of malt extract agar (MEA) and 25% glycerol nitrate agar (G25N). Inoculation was made from a semisolid suspension (0.5 ml of 0.2% agar with 0.05% Tween 80). An inoculating loop of conidia was added to the tube and mixed. A loop of suspension was inoculated in a pattern of three sites per plate. A needle was used to stab inoculate the 6 cm plate. The incubation regime was: one CYA plate plus the MEA and G25N plates at 24° C., one CYA plate at 37° C., and the 6 cm CYA plate at 5° C. After seven days the colony diameters, colors, and other characters were recorded and are set forth in Table I. On potato dextrose agar (PDA, Difco), a deep red color on the bottom or reverse of the colony is produced.

No sexual stage was noted. This results in the culture (NRRL 18887) being keyed in the Penicillium Key to subgenera. Within the Penicillium Key, the penicillus type alone determines the subgenus to which a species is allocated. This species has several characteristics that distinguish it from the Biverticillium subgenus even though its penicillus is biverticilliate. The species consistently produces colonies greater than 10 mm in diameter in 7 days on glycerol nitrate agar. The metulae appear longer than the phialides and are in verticils of 2–5. These characteristics place this Penicillium sp. (NRRL 18887) into the subgenus Furcatum.

The foregoing description is illustrative of a strain of Penicillium sp. UC 7780 (NRRL 18887) which can be employed in the production of Marcfortine and derivatives thereof. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

This description is also desired and intended to include inter- and intraspecific genetic recombinants produced by genetic techniques well known to those skilled in the art, such as, for example, conjugation, transultion and genetic engineering techniques.

Penicillium sp. UC 7780 (NRRL 18887) may be cultivated under aerobic condition in the same manner as commonly employed in the art for cultivation of a known strain of the genus Penicillium.

As medium components may be employed any of the well-known nutrient materials for Penicillium. For instance, as an assimilable carbon source, glucose, glycerol, maltose, dextrin, starch, lactose, sucrose, molasses, soybean oil, cotton seed oil, etc., preferably glucose and glycerol may be employed and, as an assimilable nitrogen source, soybean meal, peanut meal, cotton seed meal, fish meal, corn steep liquor, peptone, rice, bran, meat extract, yeast, yeast extract, sodium nitrate, ammonium nitrate, ammonium sulfate, etc. may be used. And, such inorganic salts as sodium chloride, phosphates, calcium carbonate, etc. may be added to a culture medium. A minor amount of a metal salt may also be added, if necessary. Further, a minor amount of a heavy metal may be added, if necessary.

Particularly, in cultivating the Penicillium sp. (NRRL 18887) under aerobic condition, ordinary aerobic cultivation methods such as, for example, solid culture, culture under aeration and agitation, shaken culture etc. may be favorably utilized.

In carrying out cultivation with aeration and agitation, an anti-foaming agent, e.g., silicon oil, vegetable oils, surfactants, etc. may be suitably employed.

The pH of the medium may be usually within a pH range of 3–9 and preferably within or around neutral range and cultivation temperatures may be usually of 20°–30° C., in particular about 21° C. being preferred.

Cultivation may be continued until Marcfortine A will be substantially accumulated in a culture medium, usually for 20 hours to 240 hours, preferably for 48 hours to 168 hours and, after cultivation, Marcfortine A may be isolated and recovered from a cultured broth by a suitable combination of various method. For example, there may be extraction with an organic solvent, e.g. ether, ethyl acetate or chloroform; dissolution into a more polar solvent, e.g. acetone or alcohol; removal of impurities with a less polar solvent, e.g. petroleum ether or hexane, adsorptive chromatography with active carbon or silica gel; gel filtration through a column of "sephadex" (available from Pharmacia Co., Ltd, U.S.A.); and so on.

The instant compounds of this invention are unexpectedly potent antiparasitic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition, are also active against Dirofilaria in dogs, Nematospiroides and Syphacia in rodents, biting insects and migrating dipterous larvae such as Hypoderma sp. in cattle, and Gastrophilus in horses.

The instant compounds are also useful against endo and ecto parasites which cause parasitic diseases in humans. Examples of such endoparasites which infect man include gastro intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra intestinal stages of the intestinal worms Strongylides and Trichinella.

Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans. The instant compounds when administered orally or parenterally are administered at a dosage rate of from 0.05 to 20 mg/kg of animal body weight.

The instant compounds are also useful against common household pests such as Blatella sp. (cockroach), Tineola sp. (clothes moth), Attagenus sp. (carpet beetle), *Musca domestica* (housefly) and against *Solenopsis invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematocide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or drench bolus form or alternatively they can be mixed in the animals feed. The capsules, tablets, and drenches boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, suspending agents, and/or binders such that a uniform mixture solution or suspension is obtained. An inert ingredient is one that will not react with the instant compounds and which is non toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 20% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 20% by weight of the active ingredient are acceptable. Preferred formulations are those containing from 0.5 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.005 to 50 mg per kg of animal body weight either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention.

Procedure No. 1: Production and Isolation of Marcfortine A

Seed Fermentation Process

Seed fermentations are inoculated using agar plugs of isolate Penicillium sp. UC 7780 (NRRL 18887) stored over liquid nitrogen. Three plugs are thawed and used as inoculum. GS-7 is composed of glucose and cottonseed flour (sold under the trademark "Pharmamedia" by Traders Protein, Procter & Gamble Oilseed Products Co., Memphis, Tenn., U.S.A.). Unsupplemented tap water is used to hydrate the medium components and the medium is adjusted to pH 7.2 with $NH_4OH$. The medium is dispensed into unbaffled closed-system flasks at 300 ml pper 1000 ml flask, and sterilized by autoclaving at 121° C. for 30 minutes. Each closed-system flask containing 300 ml of GS-7 medium is inoculated with three agar plugs of Penicillium sp. UC 7780 (NRRL 18887) and shaken on a rotary shaker at 250 rpm for 36 hr at 22° C.

Secondary Seed Fermentation Process

The mature seed cultures are used as inoculum for the secondary medium at a 0.3% seed rate. The secondary medium is composed of glucose monohydrate (sold as under the trademark Cerelose by C.P.C. International) 25 g, cottonseed flour (sold under the trademark "Pharmamedia") 25 g, $MgCl_2.6H_2O$ 329.8 mg, $MnSO_4.H_2O$ 11.4 mg, $FeSO_4.7H_2O$ 3.2 mg, $Na_2MoO_4.2H_2O$ 1.8 mg, $CaCl_2.2H_2O$ 367.6 mg, NaCl 84.2 mg, KCl 5.8 mg, $ZnSO_4.7H_2O$ 0.1 mg, $CoCl_2.6H_2O$ 0.1 mg, $CuSO_4.5H_2O$ 3.1 mg, and silicone antifoam (sold under the trademark SAG-471 Antifoam) 0.5 ml per liter of reverse-osmosis grade water. Medium components sufficient for 200 liters of secondary seed medium are hydrated in reverse-osmosis grade water to a q.s. volume of 190 liters in a 250-L fermentor. After formulation, the pH of the medium is adjusted to pH 7.2 with $NH_4OH$, and then the medium is sterilized at 121° C. for 30 minutes. Two closed-system flasks of the mature primary-seed culture are used as inoculum at a 0.3% seed rate. The secondary seed culture is incubated at at 22° C., with 125 slm aeration, 5 psig backpressure, and 250 rpm for 36 hours.

Production Fermentation Process

The production medium is composed of beet molasses 50 g, fish meal (sold under the trademark Menhaden Select Fish Meal) 16 g, yeast extract (sold under the trademark Fidco) 10 g, $MgCl_2.6H_2O$ 329.8 mg, $MnSO_4.H_2O$ 11.4 mg, $FeSO_4.7H_2O$ 3.29 mg, $Na_2MoO_4.2H_2O$ 1.8 mg, $CaCl_2.2H_2O$ 367.6 mg, NaCl 84.2 mg, KCl 5.8 mg, $ZnSO_4.7H_2O$ 0.1 mg, $CoCl_2.6H_2O$ 0.1 mg, $CuSO_4.5H_2O$ 3.1 mg, and silicone antifoam (sold under the trademark SAG-471 Antifoam) 0.5 ml per liter of reverse-osmosis grade water.

Medium components sufficient for 5,000 liters of medium are hydrated in reverse-osmosis grade water to a q.s. volume of 4,700 liters in a 5,000 L fermentor. After formulation, the pH of the medium is adjusted to pH 7.0 with KOH, and then the medium is sterilized at 123° C. for 30 minutes. The mature secondary-seed culture is used as inoculum at a 1.0% seed rate. The culture is incubated at 22° C., with 2,500 slm aeration, 5 psig backpressure, and 250 rpm for 96 hours.

Isolation of Marcfortine A:

The 4900 L fermentation volume is harvested by passing through a high shear mixer to the harvest vessel. Following transfer, 4% wt./v. of diatomaceous earth and ½ volume of methylene chloride are added. The harvest solution is then filtered using a filter press. The filter cake is washed 2 times with a 10% volume of methylene chloride.

The filtrate obtained is decanted to remove the water (aqueous) phase. The remaining product-rich methylene chloride phase is then concentrated to a volume of 44 L. The concentrate is then polished using a 20% concentrate volume (9 L)of methylene chloride and diatomaceous earth over a filter.

The 53 L polished concentrate is further purified to separate Marcfortine A from other components by silica gel chromatography and crystallization.

Before chromatography, the polished concentrate is divided into four approximately equal aliquots. Each aliquot is chromatographed over a newly packed 9" diameter column prepared from 25 Kg of dry silica gel (bed volume 59 L). The loaded columns are eluted with 120 L of 10% acetone in methylene chloride, 120 L of 20% acetone in methylene chloride, 120 L of 30% acetone in methylene chloride, 160 L of 40% acetone in methylene chloride, and 130 L of acetone collecting the 30 and 40% eluates as 20 L fractions. Eluates are monitored by TLC, using for example a solvent system comprised of 6% isopropanol and 0.3% ammoniumn hydroxide in methylene chloride to develop Whatman LK6DF silica gel plates. Fractions of Marcfortine A (containing a small amount of Marcfortine D which co-chromatographs with D) are crystallized from acetone. Appropriate fractions ( 40–100 L) are concentrated under reduced pressure to a volume of approximately 5 L. The solution ( or light slurry) is then transferred to a rotatory evaporater and concentration continued under reduced pressure. Several 1 L portions of acetone are added during the course of the concentration until the methylene chloride is completely displaced. The resulting acetone slurry (approximately 1 L volume) is refrigerated overnight, and the crystals of Marcfortine A are collected and washed with several small portions of cold acetone, and dried under vacuum. Such crystals may be contaminated with several percent of Marcfortine D. Repeated recrystallization from methylene chloride/acetone (displacing methylene chloride as described) affords pure Marcfortine A.

Isolation of marcfortine D

The 4900 L fermentation volume is harvested by passing through a high shear mixer to the harvest vessel. Following transfer, 4% wt./v. of diatomaceous earth and ½ volume of methylene chloride are added. The harvest solution is then filtered using a filter press. The filter cake is washed 2 times with a 10% volume of methylene chloride.

The filtrate obtained is decanted to remove the water (aqueous) phase. The remaining product-rich methylene chloride phase is then concentrated to a volume of 44 L. The concentrate is then polished using a 20% concentrate volume (9 L)of methylene chloride and diatomaceous earth over a filter.

The 53 L polished concentrate is further purified to separate Marcfortine A from other components by silica gel chromatography and crystallization.

Before chromatography, the polished concentrate is divided into four approximately equal aliquots. Each aliquot is chromatographed over a newly packed 9" diameter column prepared from 25 Kg of dry silica gel (bed volume 59 L). The loaded columns are eluted with 120 L of 10% acetone in methylene chloride, 120 L of 20% acetone in methylene chloride, 120 L of 30% acetone in methylene chloride, 160 L of 40% acetone in methylene chloride, and 130 L of acetone collecting the 30 and 40% eluates as 20 L fractions. Eluates are monitored by TLC, using for example a solvent system comprised of 6% isopropanol and 0.3% ammoniumn hydroxide in methylene chloride to develop Whatman LK6DF silica gel plates. Fractions of marcfortine A containing marcfortine D are concentrated. One gram of this material is dissolved in formic acid (20 mL, 93%) and standing at room temperature for 16 h. After the volatile components are removed with reduced pressure, the residue is subjected to silica gel chromatography (1:20 $MeOH:CH_2Cl_2$) to give marcfortine D (100 mg) as a white solid. The structure of the product can be confirmed by NMR spectroscopy and mass spectrometry. HRMS (FAB) M/Z [M+H] calculated for $C_{28}H_{35}N_3O_3$+H: 462.2756; measured: 462.2739.

Procedure 1A Production and Isolation of Marcfortines A and C

Primary Seed Fermentation Process

Seed fermentations are inoculated using agar plugs of isolate Penicillium sp. UC 7780 (NRRL 18887) stored over liquid nitrogen. Three plugs are thawed and used as inoculum for 100 ml of GS-7 seed medium. GS-7 is composed of glucose and cottonseed flour (sold under the trademark "Pharmamedia" by Traders Protein, Procter & Gamble Oilseed Products Co., Memphis, Tenn., U.S.A.) each added at a concentration of 25 g/L of tap water. After formulation, the pH of GS-7 is adjusted to 7.2 using NH$_4$OH. The medium is autoclaved in 100 ml volumes in 500 ml unbaffled fermentation flasks for 30 min. Sterile GS-7 is inoculated as described above and shaken at 250 rpm for 35–58 hr at 23° C.

Production Fermentation Process (shaker flask)

The mature seed cultures are used as inoculum for the production medium at a 1% seed rate. The production medium is composed of glucose 45 g, enzymatically digested casein (sold under the trademark Peptonized Milk Nutrient by Sheffield Products, Norwich, N.Y., U.S.A.) 25 g, yeast extract (sold under the trademark BACTO Yeast Extract Code: 0127 by Difco Laboratories, Detroit, Mich.) 2.5 g per liter of tap water. After formulation, the pH of the production medium is adjusted to 7.0 using potassium hydroxide. This medium is then autoclaved for 30 min in 100 ml volumes contained in 500 ml baffled fermentation flasks. Sterile production medium is inoculated as described above, and shaken for 7–14 days at 250 rpm at 21° C.

Production Fermentation Process (Labraferm tanks)

The mature seed cultures are used as inoculum for the sterile production medium at a 0.5% seed rate. The production medium is described above. After pH adjustment to 7.0 using KOH, 10 L of this medium are autoclaved for 90 min in 12 L Labraferm tanks (New Brunswick Scientific Co., Inc.). The tanks are inoculated at a 0.5% seed rate and stirred at 500 rpm at 20° C. for 5–9 days. The air flow rate is maintained between 10–15 L/min.

Isolation of Marcfortines A and C

Whole fermentation broth (35 l) is macerated at low speed in a large commercial Waring Blender and then blended with an equal volume of methylene chloride. The mixture is stored overnight under refrigeration and then subjected to centrifugation to break the emulsion. The resulting clear methylene chloride layer is drawn off and evaporated under reduced pressure. A concentrated solution of the residue (37.4 g) in methylene chloride is applied to a column of silica gel (1 Kg) slurry packed in methylene chloride. The column is eluted with increasing concentrations of acetone in methylene chloride (10%, 20%, 30%, 40%, and 50% acetone). Fractions are monitored by TLC and appropriate fractions evaporated and crystallized from acetone to give Marcfortine A and Marcfortine C.

Procedure 1B Production and Isolation of Marcfortines A and C

Seed Fermentation Process

Seed fermentations are inoculated using agar plugs of isolate Penicillium sp. UC 7780 (NRRL 18887) stored over liquid nitrogen. Three plugs are thawed and used as inoculum for 100 ml of GS-7 seed medium. GS-7 is composed of glucose and cottonseed flour (sold under the trademark "Pharmamedia" by Traders Protein, Procter & Gamble Oilseed Products Co., Memphis, Tenn., U.S.A.) each added at a concentration of 25 g/L of tap water. After formulation, the pH of GS-7 is adjusted to 7.2 using NH$_4$OH. The medium is autoclaved in 100 ml volumes in 500 ml unbaffled fermentation flasks for 30 min. Sterile GS-7 is inoculated as described above and shaken at 250 rpm for 35–58 hr at 23° C.

Production Fermentation Process (Shake Flask)

The mature seed cultures are used as inoculum for the production medium at a 1% seed rate. The production medium is composed of glucose 20 g, glycerol 15 ml, cottonseed flour (sold under the trademark "Pharmamedia" by Traders Protein, Procter & Gamble Oilseed Products Co., Memphis, Tenn., U.S.A.) 20 g, soybean meal 10 g, and K$_2$HPO$_4$ 3 g per liter of tap water. After formulation, the pH of the production medium is adjusted to 6.8 using potassium hydroxide. This medium is then autoclaved for 30 min in 100 ml volumes contained in 500 ml baffled fermentation flasks. Sterile production medium is inoculated as described above, and shaken for 7–14 days at 250 rpm at 21° C.

Production Fermentation Process (Labraferm tanks)

The mature seed cultures are used as inoculum for the sterile production medium at a 0.5% seed rate. The production medium is described above. After pH adjustment to 7.0 using KOH, 10 L of this medium are autoclaved for 90 min in 12 L Labraferm tanks (New Brunswick Scientific Co., Inc.). The tanks are inoculated at a 0.5% seed rate and stirred at 500 rpm at 20° C. for 5–9 days. The air flow rate is maintained between 10–15 L/min.

Isolation of Marcfortines A and C

Whole fermentation broth (35 l) is macerated at low speed in a large commercial Waring Blender and then blended with an equal volume of methylene chloride. The mixture is stored overnight under refrigeration and then subjected to centrifugation to break the emulsion. The resulting clear methylene chloride layer is drawn off and evaporated under reduced pressure. A concentrated solution of the residue (37.4 g) in methylene chloride is applied to a column of silica gel (1 Kg) slurry packed in methylene chloride. The column is eluted with increasing concentrations of acetone in methylene chloride (10%, 20%, 30%, 40%, and 50% acetone). Fractions are monitored by TLC and appropriate fractions evaporated and crystallized from acetone to give Marcfortine A and Marcfortine C.

Synthesis of 14-substituted marcfortines

Treatment of marcfortine A (Formula 1a, Chart A) with cyanogen iodide produces a mixture (Formula 5) of 16α-iodo-17β-cyanomarcfortine A and 16β-iodo-17α-cyanomarcfortine A which can be separated by silica gel chromatography. Dehydroiodination of this mixture with potassium hydroxide in methanol leads to 16,17-dehydro-17-cyanomarcfortine A (Formula 6) which is oxidized by selenium dioxide to 17-ketomarcfortine A (Formula 7). Introduction of a double bond between C15 and C16 is accomplished by selenation of position-16 (phenyl selenyl chloride and LDA) followed by oxidation of the selenium intermediate with hydrogen peroxide. Subsequent elimination of the phenylselenic acid gives 15,16-dehydro-17-ketomarcfortine A (Formula 8). This compound is a key intermediate in the synthesis of 14α-hydroxymarcfortine A (Formula 10) to which it can be converted by either of two distinct synthetic routes.

In the first route allylic oxidation of position-14 of this material using potassium bis(trimethylsilyl)amide and 2-phenylsulfonyl-3-phenyloxaziridine is accompanied by oxidation of position-16 to give a mixture of the required 14α-hydroxy-15,16-dehydro-17-ketomarcfortine A (Formula 9a) and 14,15-dehydro-16-hydroxy-17-ketomarcfortine A (Formula 9b). These two products are separated by silica gel chromatography. The compound of Formula 9a is reduced by means of lithium aluminum hydride in THF to 14α-hydroxymarcfortine A (Formula 10), a title compound of this invention disclosure. Alternatively, the compound of Formula 8 (Chart B) is oxidized with selenium dioxide in dioxane to afford a 2:1 mixture of 14α-hydroxy-15,16-dehydro-17-ketomarcfortine A (Formula 9a) and 15,16-dehydro-14,17-diketomarcfortine A (Formula 11). These are separated by means of silica gel chromatography. Each of these compounds is independently converted to 14α-hydroxy-17-ketomarcfortine A (Formula 12a): the compound of Formula 9a by reduction of the 15,16-double bond with lithium triethylborohydride; the compound of Formula 11 by reduction of the carbonyl at position 14 with lithium borohydride. In the latter case, an equal amount of 14β-hydroxy-17-ketomarcfortine A (Formula 12b) is also produced which is removable by chromatography. The compound of formula 12a is reduced with borane tetrahydrofuran (THF) complex to give 14α-hydroxymarcfortine A (Formula 10).

14α-Hydroxy-15,16-dehydro-17-ketomarcfortine A (Formula 9a, Chart C) is reduced with lithium triethylborohydride to 14α-hydroxy-17-ketomarcfortine A (Formula 12a). This is transformed by means of a Swern oxidation using oxalyl chloride and DMSO to 14,17-diketomarcfortine A (Formula 13). Treatment with methylmagnesium bromide in a Grignard reaction produces a mixture of 14α-hydroxy-14β-methyl-17-ketomarcfortine A (Formula 14a) and 14β-hydroxy-14α-methyl-17-ketomarcfortine A (Formula 14b) which are separated by silica gel chromatography. The ratio of the products is dependent upon the solvent used: methylene chloride gives a 6:1 ratio, while THF gives a >50:1 ratio, respectively. Reduction of the compound of Formula 13a with lithium aluminum hydride gives 14α-hydroxy-14β-methylmarcfortine A (Formula 15).

Swern oxidation of 14α-hydroxymarcfortine A (Formula 10, Chart D) provides 14-ketomarcfortine A (Formula 16), which is reduced with sodium borohydride to 14-β-hydroxymarcfortine A (Formula 17). Treatment of 14-ketomarcfortine A (Formula 16) with ethylmagnesium bromide in a grignard reaction produces 14α-hydroxy-14-ethylmarcfortine A (Formula 19). Treatment of 14α-hydroxymarcfortine A (Formula 10) with m-chloroperoxybenzoic acid produces 14α-hydroxymarcfortine A N-oxide (Formula 18). 14β-methylmarcfortine A can be prepared from 14α-hydroxy-14β-methylmarcfortine A by means of dehydroxylation. Thus, 14α-hydroxy-14β-methylmarcfortine A is treated with phenylchlorothionoformate in the presence of base. This thionoformate derivative of 14α-hydroxy-14β-methylmarcfortine A is reduced with tri-n-butyltin hydride to produce 14β-methylmarcfortine A.

Alternatvely, 14α-hydroxymarcfortine A can be synthesized from marcfortine A (Chart E). Treatment of marcfortine A with sodium bicarbonate and iodine in aqueous tetrahydrofuran produces 17-ketomarcfortine A (Formula 7), which can be disulfenylated by using LDA and phenyl disulfide to give 16-dithiophenyl-17-keto marcfortine A (Formula 20, chart E) in 60% yield from marcfortine A. Oxidation with m-chloroperoxybenzoic acid produces 16-thiophenyl-16-sulfoxyphenyl-17-ketomarcfortine A (Formula 21), which eliminates in refluxing toluene to yield 15,16-dehyro-16-thiophenyl-17-ketomarcfortine A (Formula 22). Subsequent treatment with m-chloroperoxybenzoic acid produces 15,16-dehydro-16-sufoxyphenyl-17-ketomarcfortine A (Formula 23), which undergoes rearrangement by using diethyl amine in methanol to produce 15,16-dehydo-14α-hydroxy-17-ketomarcfortine A (Formula 9a).

14α-Hydroxy-15α-methylmarcfortine A (Formula 35, Chart G) can be synthesized from 15,16-dehydro-14α-hydroxy-17-ketomarcfortine A (Formula 9a, Chart G). Thus, 15,16-dehydro-14α-hydroxy-17-ketomarcfortine A (Formula 9a) is treated with either methylmagnesium bromide or lithium dimethylcopper to produce 15α-methyl-14α-hydroxy-17-ketomarcfortine A (Formula 34), which is reduced with borane-dimethylsulfide complex to produce 15α-methyl-14α-hydroxymarcfortine A (Formula 35). 15α-Methyl-14α-hydroxy-17-ketomarcfortine A (Formula 34) is transformed by means of a Swern Oxidation using oxalyl chloride and DMSO to 15α-methyl-14,17-diketomarcfortine A (Formula 36). Treatment with methylmagnesium bromide in a Grignard reaction produces 15α-Methyl-14α-hydroxy-14β-methyl-17-ketomarcfortine A (Formula 37), which is reduced with borane-dimethylsulfide complex to produce 15α-methyl-14α-hydroxy-14β-methylmarcfortine A (Formula 38).

These previoulsy described procedures can be used to produce 14-substituted marcfortine B, C and D derivatives.
Preparation of 16-iodo-17-cyanomarcfortine A as a mixture of diastereomers (Formula 5)

Solid cyanogen iodide (11.7 g, 76.5 mmol) is added to a solution of marcfortine A (10.5 g, 22 mmol) in CHCl$_3$ (150 mL) and the reaction mixture heated under reflux until all of the marcfortine A has been consumed (about 5 h). The resulting black solution is cooled to room temperature, diluted with CH$_2$Cl$_2$ (100 mL), washed with sat NaHCO$_3$, and then washed with a solution of Na$_2$SO$_3$. The organic phase is separated, dried over MgSO$_4$, and concentrated to dryness. The resulting crude solid is subjected to silica gel chromatography (3:2-EtOAc: hexane) to give 16-Iodo-17-cyanomarcfortine A (12.5 g, 90%) as a white powdery solid. The structure of the product can be confirmed by nuclear magnetic resonance spectroscopy and mass spectrometry.
Preparation of 16,17-dehydro-17-cyanomarcfortine A (Formula 6)

16-Iodo-17-cyanomarcfortine A (9.5 g, 15 mmol) is dissolved in MeOH (150 mL), and aqueous KOH (45%, 3 mL) is added. The reaction mixture is stirred at room temperature for 2 h. Water is added and the resulting white precipitate collected by filtration, washed with water, and dried overnight under vacuum to give 16,17-Dehydro-17-cyanomarcfortine A (6.6 g, 75%) as a white powder. The structure of the product can be confirmed by nuclear magnetic resonance spectroscopy and mass spectrometry. MS (FAB) M/Z [M+H]: 501.
Preparation of 17-ketomarcfortine A (Formula 7)

Selenium dioxide (2.9 g, 26 mmol) is added to a solution of 16,17-Dehydro-17-cyanomarcfortine A (6.0 g, 10 mmol) in 95% EtOH (100 mL) and the reaction mixture stirred at room temperature for 2 h. The reaction is quenched by adding sat NaHCO$_3$ (100 mL). The resulting mixture is extracted with CH$_2$Cl$_2$ (2×200 mL). The extracts are combined, dried (MgSO$_4$), and concentrated to give 7 g of crude product. This material is purified by silica gel chromatography (EtOAc) to give 17-ketomarcfortine A (3.6 g, 75%) as a white solid. The structure of the product can be confirmed by nuclear magnetic resonance spectroscopy and mass spectrometry. HRMS (FAB) M/Z [M+H] calculated for C$_{28}$H$_{33}$N$_3$O$_5$+H: 492.2498; measured: 492.2478.

Alternatively, and more preferably, the title compound can be synthesized by using p-toluenesufonic acid. Thus, p-toluenesulfonic acid monohydrate (1 g) is to a solution of 16,17-dehydro-17-cyanomarcfortine A (10 g) in 95% MeOH (50 mL) and the reaction mixture stirred at room temperature for 1 h. Triethyl amine (2 mL) is added to the mixture and the solvent was evaporated. The residue is triturated with 10% aqueous sodium carbonate solution (100 mL) and the solid is filter and dried to give the title compound as a solid (90% yield). The structure of the product can be confirmed by nuclear magnetic resonance spectroscopy and mass spectrometry.

Preparation of 15,16-dehydro-17-ketomarcfortine A (Formula 8)

A solution of lithium diisopropylamide is prepared from a solution of n-butyl lithium (1.6 M, 9.9 mL, 15.4 mmol) in hexane and diisopropylamine (2.2 mL, 15.7 mmol). This is diluted with anhydrous tetrahydrofuran (THF, 20 mL) and cooled to at −78°. A solution of 17-ketomarcfortine A (2.0 g, 4.1 mmol) in anhydrous THF (20 mL) is added dropwise and the reaction mixture allowed to warm to −40° during 1 h. The mixture is again cooled to −78° and treated dropwise with phenyl selenium chloride (19 mg, 5.2 mmol) in THF (10 mL). After 5 min the reaction is quenched with sat NaHCO$_3$, extracted with CH$_2$Cl$_2$, dried (MgSO$_4$), and concentrated to give a yellow solid which can be used without further purification. This material is dissolved in THF (150 mL) and treated with H$_2$O$_2$ (30%, 1.5 mL) at 0°. The cooling bath is removed and the reaction mixture stirred for 30 min at room temperature. The reaction is quenched by adding NaOH (1N, 100 mL). The mixture is extracted with CH$_2$Cl$_2$ (2×200 mL). The extracts are combined, dried (MgSO$_4$), and concentrated to give crude product. This material is purified by silica gel chromatography (EtOAc) to give 15,16-dehydro-17-ketomarcfortine A (1.3 g,65%) as a white solid. The structure of the product is confirmed by nuclear magnetic resonance spectroscopy and mass spectrometry. HRMS (FAB) M/Z [M+H] calculated for C$_{28}$H$_{31}$N$_3$O$_5$+H: 490.2342; measured: 490.2345.

Preparation of 14α-hydroxy-15,16-dehydro-17-ketomarcfortine A (Formula 9a) using oxaziridine chemistry A solution of potassium bis(trimethylsilyl)amide in toluene (0.5M, 1 mL, 0.5 mmol) is added dropwise to a solution of 15,16-dehydro-17-ketomarcfortine A (66 mg, 0.14 mmol) in THF (2 mL) at −78°. The resulting pale yellow, turbid solution is allowed to warm to −40° during 1 h. The reaction mixture is cooled −78°, stirred 15 min, and then treated by the dropwise addition of a solution of 2-phenylsulfonyl-3-phenyloxaziridine (42 mg, 0.16 mmol) in THF (2 mL). The mixture is stirred 5 min after which the reaction is quenched by adding NaHCO$_3$. The mixture is extracted with CH$_2$Cl$_2$ (2×25 mL). The extracts are combined, dried (MgSO$_4$), and concentrated to give crude material. This is purified by preparative thin layer chromatography (silica gel, EtOAc) to give 14α-Hydroxy-15,16-dehydro-17-ketomarcfortine A (8 mg, 12%) as a white solid. The structure can be confirmed by nuclear magnetic resonance spectroscopy and mass spectrometry. HRMS (FAB) M/Z [M+H] calculated for C$_{28}$H$_{31}$N$_3$O$_6$+H: 506.2291; measured: 506.2280. 14,15-Dehydro-16-hydroxy-17-ketomarcfortine A (14 mg, 20%) is also obtained from the layer. Its structure can be confirmed by nuclear magnetic resonance spectroscopy.

Preparation of 14α-hydroxy-15,16-dehydro-17-ketomarcfortine A (Formula 9a), 15,16-dehydro-14,17-diketomarcfortine A (Formula 11) and 14,15-dehydro-16,17-diketomarcfortine A (Formula 24) using selenium dioxide 15,16-Dehydro-17-ketomarcfortine A (1.29 g, 2.6 mmol) is dissolved in p-dioxane (30 mL) and treated with selenium dioxide (390 mg). The mixture is refluxed for 1 h and the solvent evaporated in vacuo. The residue is triturated with methylene chloride (30 mL) and filtered. The filtrate is concentrated, and the residue subjected to silica gel chromatography (1:20 MeOH:EtOAc) to give 14α-hydroxy-15,16-dehydro-17-ketomarcfortine A (430 mg, 32%) as a solid.

15,16-Dehydro-14,17-diketomarcfortine A (Formula 11, 212 mg, 16%) is also obtained from the chromatography. 14,15-Dehydro-16,17-diketomarcfortine A (Formula 24, 106 mg, 8%) is also obtained from the chromatography. The structure of these products can be confirmed by nuclear magnetic resonance spectroscopy and mass spectrometry.

Conversion of 14α-hydroxy-15,16-dehydro-17-ketomarcfortine A (Formula 9a) to 15,16-dehydro-14,17-diketomarcfortine A (Formula 11)

14α-Hydroxy-15,16-dehydro-17-ketomarcfortine A (60 mg, Formula 9a) is dissolved in methylene chloride (10 mL) and treated with manganese dioxide (60 mg). The mixture is stirred at room temperature for 1 h and concentrated. Preparative thin layer chromatography of the residue on silica gel (50% methylene chloride in EtOAc) afforded 15,16-dehydro-14,17-diketomarcfortine A (Formula 11, 35 mg, 60%). The structure of these products can be confirmed by nuclear magnetic resonance spectroscopy and mass spectrometry.

EXAMPLE 1

Preparation of 14ac-hydroxymarcfortine A (Formula 10)

14α-Hydroxy-15,16-dehydro-17-ketomarcfortine A (20 mg, 0.040 mmol) is dissolved in THF (5 mL) and treated with a solution of Lithium Aluminum Hydride (1M, 0.11 mL, 0.11 mmol) in THF at 0°. The mixture is stirred for 0.5 h at 0° after which a solution of NaHCO$_3$ (10%) is added. The mixture is extracted with CH$_2$Cl$_2$ (2×10 mL). The extracts are combined, dried (MgSO$_4$), and the solvent evaporated. Preparative thin layer chromatography of the residue on silica gel (10% MeOH in EtOAc) afforded 14α-hydroxymarcfortine A (3 mg, 15%) as a white solid. The structure of the product can be confirmed by nuclear magnetic resonance spectroscopy and mass spectrometry. HRMS (FAB) M/Z [M+H] calculated for C$_{28}$H$_{35}$N$_3$O$_5$+H: 494.2655; measured: 494.2653.

Preparation of 14α-hydroxy-17-ketomarcfortine A (Formula 12a) from 14α-hydroxy-15,16-dehydro-17-ketomarcfortine A (Formula 9a)

14α-Hydroxy-15,16-dehydro-17-ketomarcfortine A (50 mg, 0.1 mmol) is dissolved in THF (5 mL) and treated with a solution of lithium triethylborohydride in THF (1M, 0.7 mL) at −78°. The mixture is stirred for 0.5 h at −78°. The reaction is quenched by adding MeOH (1 mL), and the mixture is concentrated. The resulting solid is subjected to silica gel chromatography (1:20 MeOH:CH$_2$Cl$_2$) to give 14α-hydroxy-17-keto marcfortine A (43 mg, 86%) as a white solid. The structure of the product can be confirmed by NMR spectroscopy and mass spectrometry. HRMS (FAB) M/Z [M+H] calculated for C$_{28}$H$_{33}$N$_3$O$_6$+H: 508.2447; measured: 508.2437.

Preparation of 14α-hydroxy-17-ketomarcfortine A (Formula 12a) from 15,16-dehydro-14,17-diketomarcfortine A (Formula 11)

15,16-Dehydro-14,17-diketomarcfortine A (470 mg, 0.93 mmol) is dissolved in THF and treated with a solution of lithium borohydride in THF (1M, 2 mL) at room temperature. The mixture is stirred for 2 h after which a solution of NaHCO$_3$ (10%) is added. The mixture is extracted with CH$_2$Cl$_2$ (2×20 mL). The extracts are combined, dried (MgSO$_4$), and the solvent evaporated. The residue contains a mixture of the two epimers which are readily separated by silica gel chromatography (1:20 MeOH: EtOAc): 14α-hydroxy-17-ketomarcfortine A (90 mg, 19%) and 14β-hydroxy-17-ketomarcfortine A (94 mg, 20%). The structure of both products can be confirmed by NMR spectroscopy and mass spectrometry.

Preparation of 14α-hydroxymarcfortine A (Formula 10) from 14α-hydroxy-17-ketomarcfortine A (Formula 12a)

14α-Hydroxy-17-ketomarcfortine A (413 mg, 0.81 mmol) is dissolved in THF (20 mL) and treated with a solution of borane THF complex in THF (1M, 2.43 mL) at 0°. The mixture is stirred for 2.25 h. The mixture is stirred for 0.5 h after which MeOH (3 mL) is added. After the solvent is evaporated, the residue is subjected to silica gel chromatography (1:16 MeOH:EtOAc) to give 14α-hydroxymarcfortine A (250 mg, 92% yield based on starting material recovered) and 14α-hydroxy-17-ketomarcfortine A (starting material, 140 mg, 34%).

Preparation of 14,17-diketomarcfortine A (Formula 13)

A solution of oxalyl chloride (40 µL) in anhydrous $CH_2Cl_2$ (5 mL) is treated with dimethyl sulfoxide (45 µL) at −78°. The mixture is stirred for 1 h at −78°. A solution of 14α-hydroxy-17-ketomarcfortine A (27 mg) in $CH_2Cl_2$ (2 mL) is added dropwise. The reaction mixture is stirred 20 min at −78°. Triethylamine (0.3 mL) is added to the reaction mixture which is allowed to warm to room temperature during 20 min. The mixture is partitioned between 10% $Na_2CO_3$ (10 mL) and $CH_2Cl_2$ (10 mL). The organic layer is dried (MgSO4) and concentrated. The residue is subjected to silica gel chromatography (1:20 MeOH:$CH_2Cl_2$) to give 14,17-Diketomarcfortine A (22 mg, 80%) as a white solid. The structure of the product can be confirmed by NMR spectroscopy and mass spectrometry. HRMS (FAB) M/Z [M+H] calculated for $C_{28}H_{31}N_3O_6$+H: 506.2291; measured: 506.2280.

Preparation of 14α-hydroxy-14β-methyl-17-ketomarcfortine A (Formula 14a)

A solution of 14,17-Diketomarcfortine A (16 mg, 0.032 mmol) in $CH_2Cl_2$ (5 mL) at −78° is treated with a solution of methylmagnesium bromide (3M, 0.16 mL, 0.48 mmol) in $Et_2O$ at −78°. The resulting mixture is stirred for 0.5 h at −78°. The reaction is quenched by adding 10% $Na_2CO_3$ (a few drops). The mixture was diluted with $CH_2Cl_2$ (10 mL), dried (MgSO$_4$), and concentrated. The residue is subjected to silica gel chromatography (1:20 MeOH:$CH_2Cl_2$) to give 14α-hydroxy-14β-methyl-17-ketomarcfortine A (8 mg, 50%, $R_f$=0.25) as a white solid. The structure of the product can be confirmed by NMR spectroscopy and mass spectrometry. HRMS (FAB) M/Z [M+H] calculated for $C_{29}H_{35}N_3O_6$+H: 522.2604; measured: 522.2620. Also obtained from the layer is 14β-hydroxy-14α-methyl-17-ketomarcfortine A (1.2 mg, 7%, $R_f$=0.4) as a white solid. The structure of the product can be confirmed by NMR spectroscopy and mass spectrometry. HRMS (FAB) M/Z [M+H] calculated for $C_{29}H_{35}N_3O_6$+H: 522.2604; measured: 522.2630. The 6:1 ratio of products thus obtained is increased to greater than 50:1 and the yield increased to 80% when THF is used as the reaction solvent in place of $CH_2Cl_2$.

EXAMPLE 2

Preparation of 14α-hydroxy-14β-methylmarcfortine A (Formula 15)

A solution of 14α-hydroxy-14β-methyl-17-ketomarcfortine A (5 mg, 0.01 mmol) in THF (5 mL) is treated with a solution of Lithium Aluminum Hydride (1M, 0.03 mL, 0.03 mmol) in THF at 0°. The mixture is stirred for 0.5 h at 0° after which a solution of NaHCO$_3$ (10%) is added. The mixture is extracted with $CH_2Cl_2$ (2×5 mL). The extracts are combined, dried (MgSO$_4$), and the solvent evaporated. Preparative thin layer chromatography of the residue on silica gel (1:20 MeOH:$CH_2Cl_2$) afforded 14α-hydroxy-14α-methylmarcfortine A (2 mg, 40%). The structure of the product can be confirmed by NMR spectroscopy and mass spectrometry. HRMS (FAB) M/Z [M+H] calculated for $C_{29}H_{37}N_3O_5$+H: 508.2811; measured: 508.2816.

Preparation of 14-ketomarcfortine A (Formula 16)

A solution of oxalyl chloride (150 µL) in anhydrous $CH_2Cl_2$ (20 mL) is treated with DMSO (170 µL) at −78°. The mixture is stirred for 1 h at −78°. A solution of 14α-hydroxymarcfortine A (110 mg) in $CH_2Cl_2$ (5 mL) is added dropwise. The reaction mixture is stirred 20 min at −78°. Triethylamine (1 mL) is added to the reaction mixture which is allowed to warm to room temperature during 20 min. The mixture is partitioned between 10% Na$_2$CO$_3$ (20 mL) and $CH_2Cl_2$ (20 mL). The organic layer is dried (MgSO$_4$) and concentrated. The residue is subjected to silica gel chromatography (1:25 MeOH:$CH_2Cl_2$) to give 14-ketomarcfortine A (82 mg, 75%) as a white solid. The structure of the product can be confirmed by NMR spectroscopy and mass spectrometry. HRMS (FAB) M/Z [M+H] calculated for $C_{28}H_{33}N_3O_5$+H: 492.2498; measured: 492.2510.

EXAMPLE 3

Preparation of 14β-hydroxymarcfortine A (Formula 17)

A solution of 14-ketomarcfortine A (10 mg) in MeOH (2 mL) is treated with Sodium borohydride (5 mg) at 0°. The mixture is stirred for 0.5 h at 0° after which a solution of NaHCO$_3$ (10%) is added. The mixture is extracted with $CH_2Cl_2$ (2×10 mL). The extracts are combined, dried (MgSO$_4$), and the solvent evaporated. Preparative thin layer chromatography of the residue on silica gel (1:16 MeOH:EtOAc) affords 14β-hydroxymarcfortine A (5 mg, 50%). The structure of the product can be confirmed by NMR spectroscopy and mass spectrometry. HRMS (FAB) M/Z [M+H] calculated for $C_{28}H_{35}N_3O_5$ +H: 494.2655; measured: 494.2653.

EXAMPLE 4

Preparation of 14α-hydroxymarcfortine A N-oxide (Formula 18)

A solution of 14α-hydroxymarcfortine A (15 mg) in $CH_2Cl_2$ (3 mL) is treated with m-chloroperoxybenzoic acid (15 mg) at 0°. After the mixture is stirred for 0.5 h at 0°, treated with triethyl amine (30 µL) and concentrated. Preparative thin layer chromatography of the residue on silica gel (1:8 MeOH:$CH_2Cl_2$) affords 14α-hydroxymarcfortine A N-oxide (12 mg, 80%). The structure of the product can be confirmed by mass spectrometry. HRMS (FAB) M/Z [M+H] calculated for $C_{28}H_{35}N_3O_6$+H: 510.2604; measured: 510.2615.

EXAMPLE 5

Preparation of 14α-hydroxy-14β-ethylmarcfortine A (Formula 19)

A solution of 14-ketomarcfortine A (25 mg, 0.05 mmol) in THF (5 mL) at −78° is treated with a solution of ethylmagnesium bromide (3M, 0.15 mL, 0.45 mmol) in $Et_2O$ at −78°. The resulting mixture is stirred for 0.5 h at −78°. The reaction mixture is allowed to warm to room temperature during 20 min. The reaction is quenched by adding 10% Na$_2$CO$_3$ (a few drops). The mixture was diluted with $CH_2Cl_2$ (10 mL), dried (MgSO$_4$), and concentrated. The residue is subjected to silica gel chromatography (1:20 MeOH:$CH_2Cl_2$) to give 14α-hydroxy-14β-ethylmarcfortine A (10 mg, 45%) as a white solid. The structure of the product can be confirmed by NMR spectroscopy and mass spectrometry. HRMS (FAB) M/Z [M+H] calculated for $C_{30}H_{39}N_3O_5$+H: 522.2968; measured: 522.2983.

Preparation of 14β-methylmarcfortine A from 14α-hydroxy-14β-methylmarcfortine A

A solution of potassium bis(trimethylsilyl)amide in toluene (0.5M, 1 mL, 0.5 mmol) is added dropwise to a solution of 14α(-hydroxy-14β-methylmarcfortine A (66 mg, 0.14 mmol) in THF (2 mL) at −78°. The resulting pale yellow, turbid solution is allowed to warm to −40° during 1 h. The reaction mixture is cooled −78°, stirred 15 min, and then treated by the dropwise addition of a solution of phenyl-chlorothionoformate (0.094 mL, 0.7 mmol) in THF (2 mL). After 10 min the dry ice bath is removed. After further reaction for 3 h, the reaction is quenched by adding NaHCO$_3$. The mixture is extracted with CH$_2$Cl$_2$ (2×25 mL). The extracts are combined, dried (MgSO$_4$), and concentrated to give crude material. This is purified by preparative thin layer chromatography (silica gel, EtOAc) to give 14α-O-phenoxythiocarbonyl-14β-methylmarcfortine A.

To a solution of 14α-O-phenoxythiocarbonyl-14β-methylmarcfortine A (64 mg, 0.1 mmol) in toluene (5 mL) is added AIBN (3.3 mg) followed by addition of tributyltin hydride (54 μL, 0.2 mmol). The mixture is refluxed for 3 h. After the solvent is evaporated, the residue is purified by preparative thin layer chromatography (silica gel, EtOAc) to give 14β-methylmarcfortine A. The structure can be confirmed by nuclear magnetic resonance spectroscopy and mass spectrometry.

An alternative synthesis of 17-ketomarcfortine A (Formula 7, Chart E)

To marcfortine A (65 g, 0.136 mol) and sodium bicarbonate (137 g, 1.63 mol) in tetrahydrofuran (THF, 2 L) and water (1.25 L) at reflux is added iodine (206 g, 0.81 mol) dropwise in THF (1.25 l) over a one hour period. (Alternatively, the mixture can be stirred at room temperature for 16 hours.) After being allowed to slowly cool to ambient temperature (2.5 h), the reaction is quenched with saturated sodium thiosulfate (Na$_2$S$_2$O$_3$, 1.5 L) and extracted with ethyl acetate (2×1 L). The combined organic layers are washed with saturated sodium thiosulfate (1 L), dried (MgSO$_4$), filtered, evaporated and dried overnight in the vacuum oven (65° C.) to give 62 g of crude 17-ketomarcfortine A (Formula 7) as a yellow solid. $^1$H NMR (300 MHz, CDCl$_3$): δ 7.68 (s, 1H), 6.80 (d, 1H), 6.70 (d, 1H), 6.32 (d, 1H), 4.90 (d, 1H), 3.75 (q, 2H), 3.23 (t, 1H), 3.09 (s, 3H), 2.80 (d, 1H), 2.65 (d, 1H), 2.49–2.21(m, 2H), 2.08 (d, 1H), 1.98–1.45 (m, 5H), 1.46 (s, 3H), 1.44 (s, 3H), 1.09 (s, 3H), 0.90 (s, 3H).

Alternatively, ICl can be used instead of iodine.

Synthesis of 16-dithiophenyl-17-ketomarcfortine A (Formula 20)

The crude 17-ketomarcfortine A (5 g, 10.2 mmol) is added via a cannula in THF (150 mL) at −78° C. to an LDA solution which was prepared by adding n-BuLi (1.6M, 24.8 mL, 0.04 mol) dropwise to diisopropyl anine (5.7 mL, 0.041 mol) at 0° C. in THF (100 mL). The reaction mixture is allowed to slowly warm to −50° C. over one hour. The resulting turbid red-brown mixture is then treated with phenyl disulfide (4.4 g, 0.02 mol). The reaction is immediately quenched with saturated sodium bicarbonate solution (100 mL) and extracted with methylene chloride (CH$_2$Cl$_2$, 300 mL). The organic phase was dried (MgSO$_4$), concentrated (8 g), and chromatographed on silica gel (120 g, 60% ethyl acetate/hexane as eluant) to yield the the title compound as an off white solid (4.4 g, 61% from marcfortine A). FAB-MS 708 (M$^+$+H); $^1$H NMR (300 MHz, CDCl$_3$) δ 7.74 (s, 1H), 7.71 (d, 2H), 7.64 (d, 2H), 7.45–7.30 (m, 6H), 6.81 (d, 1H), 6.72 (d, 1H), 6.32 (d, 1H), 4.91 (d, 1H), 3.70 (q, 2H), 3.16 (t, 1H), 3.01 (s, 3H), 2.75 (d, 1H), 2.53 (dt, 1H), 2.35 (dt, 1H), 2.15–1.50 (m, 5H), 1.47 (s, 3H), 1.45 (s, 3H), 1.06 (s, 3H), 0.82 (s, 3H).

Synthesis of 16-thiophenyl-16-sulfoxyphenyl-17-ketomarcfortine A (Formula 21)

To 16-dithiophenyl-17-ketomarcfortine A (10 g, 14 mmol) in CH$_2$Cl$_2$ (250 mL) at −78° C. under a nitrogen atmosphere is added m-chloroperoxybenzoic acid (m-CPBA, 64 %, 4.2 g, 15.5 mmol) dropwise in CH$_2$Cl$_2$ (200 mL) for 15 minutes. The reaction is immediately quenched with saturated sodium thiosulfate (200 mL), diluted with saturated NaHCO$_3$ (200 mL), and extracted into CH$_2$Cl$_2$ (200 mL). Drying (MgSO$_4$), followed by concentration under reduced pressure gives of 11 g of crude 16-thiophenyl-16-sulfoxyphenyl-17-ketomarcfortine A (Formula 21). $^1$H NMR (300 MHz, CDCl$_3$) δ 8.0–7.29 (m, 11H), 6.80 (d, 1H), 6.70 (d, 1H), 6.31 (d, 1H), 4.90 (d, 1H) 3.68 (d, 1H), 3.41 (d, 1H), 3.14 (t, 1H), 3.07 (s, 3H), 2.82 (dt, 1H), 2.80–2.65 (m, 2H), 2.16 (dt, 1H), 2.05–1.1 (m, 4H), 1.47 (s, 3H), 1.43 (s, 3H), 0.96 (s, 3H), 0.83 (s, 3H).

Synthesis of 16-thiophenyl-15,16-dehydro-17-ketomarcfortine A (Formula 22)

The crude 16-thiophenyl-16-sulfoxyphenyl-17-ketomarcfortine A (Formula 21, 11 g) is refluxed in toluene (250 mL) for 45 minutes, cooled to room temperature, diluted with saturated sodium bicarbonate (300 mL) and extracted with EtOAc (300 mL). The organic layer is dried (MgSO$_4$) and concentrated to give 10.6 g of crude 16-thiophenyl-15,16-dehydro-17-ketomarcfortine A (Formula 22). FAB-MS 598(M$^+$+H); HRMS M/Z (M$^+$+H, C$_{34}$H$_{35}$N$_3$O$_5$S+H$_1$), calc. 598.2376, obsd. 598.2387. $^1$H NMR (300 MHz, CDCl$_3$) 8.18 (s, 1H), 7.55–7.45 (m, 2H), 7.29–7.45 (m, 3H), 6.83 (d, 1H), 6.70 (d, 1H), 6.34 (d, 1H), 5.92 (dt, 1H), 4.91 (d, 1H), 3.87 (q, 2H), 3.30 (dd, 1H), 3.21 (t, 1H), 3.08 (s, 3H), 2.80 (d, 1H), 2.35 (dd, 1H), 2.10 (d, 1H), 2.03 (dd, 1H), 1.78 (dd, 1H), 1.46 (s, 3H), 1.44 (s, 3H), 1.11 (s, 3H), 0.88 (s, 3H).

Synthesis of 16-sulfoxyphenyl-15,16-dehydro-17-ketomarcfortine A (Formula 23)

To the crude 16-thiophenyl-15,16-dehydro-17-ketomarcfortine A ( Formula 22, 10.6 g) in methylene chloride (300 mL) at −78° C. is added m-CPBA (64%, 2.8 g) dropwise in CH$_2$Cl$_2$ (125 mL). The reaction is quenched with saturated sodium thiosulfate (300 mL) and saturated sodium bicarbonate (300 mL), then extracted into methylene chloride (300 mL). The organic layer is dried (MgSO$_4$), filtered and concentrated to give 13 g of crude 16-sulfoxyphenyl-15,16-dehydro-17-ketomarcfortine A (Formula 23). $^1$H NMR (300 MHz, CDCl$_3$) 7.75–7.3 (m, 5H), 6.81 (s, 1H), 6.75–6.6 (m, 2H), 6.31 (d, 1H), 4.90 (d, 1H), 3.78–3.58 (m, 2H), 3.22 (t, 1H), 2.98 (s, 3H), 2.88–2.45 (m, 2H), 2.12–1.55 (m, 5H), 1.46 (s, 3H), 1.44 (s, 3H), 1.12 (s, 3H), 0.88 (s, 3H).

Synthesis of 14α-hydroxy-15,16-dehydro-17-ketomarcfortine A (Formula 9a) from 16-sulfoxyphenyl-15,16-dehydro-17-ketomarcfortine A (Formula 23)

To the crude 16-sulfoxyphenyl-15,16-dehydro-17-ketomarcfortine A (Formula 23, 13 g) in aqueous MeOH (10/1, 300 mL) is added diethyl amnine (15 mL). After refluxing for 0.5 h the reaction mixture is cooled to room temperature, diluted with water (450 mL), and extracted into CH$_2$Cl$_2$ (500 mL). Drying (MgSO$_4$), followed by concentration and silica gel chromatography (130 g, 30% acetone/ CH$_2$Cl$_2$ as eluant) produces 14α-hydroxy-15,16-dehydro-17-marcfortine A (Formula 9a, 3.6 g, 50 % yield from 16-dithiophenyl-17-keto marcfortine A) as a white solid.

EXAMPLE 6

Synthesis of 14α-hydroxy-N(1)-morpholinocarbonylmarcfortine A (Formula 25)

Potassium hydride (70 mg of a 50% oil dispersion) is added to a solution of 14α-hydroxymarcfortine A (30 mg) in 3 mL of dry tetrahydrofuran. The solution is stirred at room temperature for 1 h then morpholinocarbonyl chloride (30 υL) is added. The mixture is stirred at room temperature for 1 h then partitioned between 5% aqueous sodium bicarbonate (3 mL) and methylene chloride (3 mL). The layers are separated and the aqueous layer extracted with methylene chloride (3 mL). The combined extracts are dried with magnesium sulfate, filtered, and evaporated under vacuum. Preparative layer chromatography of the residue on a silica gel plate eluted with 5% methanol in methylene chloride affords 14α-hydroxy-N(1)-morpholinocarbonylmarcfortine A (15 mg). HRMS (FAB) M/Z [M+H] calculated for $C_{33}H_{42}N_4O_7$+H: 607.3132; measured: 607.3153

EXAMPLE 7
Synthesis of 14α-acetoxymarcfortine A (Formula 26)

14α-Hydroxymarcfortine A (50 mg) is dissolved in acetonitrile/methylene chloride (4 mL/2mL). This solution is treated with acetic anhydride (50 μL), triethyl amine (50 μL) and 4-dimethylaminopyridine (20 mg). The miture is refluxed for 1 h and cooled to room tempature. It is stirred at room temperature for 16 h, then partitioned between 5% aqueous sodium bicarbonate (3 mL) and methylene chloride (3 mL). The layers are separated and the aqueous layer extracted with methylene chloride (3 mL). The combined extracts are dried with magnesium sulfate, filtered, and evaporated under vacuum. Preparative layer chromatography of the residue on a silica gel plate eluted with 2.5% methanol in methylene chloride affords 14α-acetoxymarcfortine A (30 mg). $^1$H NMR (300 MHz, CDCl$_3$) 8.70 (s, NH), 6.80 (d, J=8.1 Hz, $C_4$—H), 6.68 (d, J=8.1 Hz, $C_5$—H), 6.37 (d, J=7.7 Hz, $C_{24}$—H), 5.44 (t, J=2.5 Hz, $C_{14}$—H), 4.92 (d, J=7.7 Hz, $C_{25}$—H), 3.75 (d, J=11.8 Hz, 1 $C_{12}$—H), 3.12 (s, 3H, N-Me), 3.04 (t, J=10.2 Hz, $C_{20}$—H), 2.6–2.8 (m, 2H), 2.5–2.1 (m, 3H), 2.16 (s, 3H, O-acetyl), 2.0–1.5 (m, 4H), 1.44 (s, 6H, $C_{27}$—H & $C_{28}$—H), 1.12 (s, 3H), 0.88 (s, 3H).

Example 8. Synthesis of 14α-O-ethoxycarbonylaminocarbonylmarcfortine A (Formula 27)

14α-Hydroxymarcfortine A (33 mg) is dissolved in acetonitrile/methylene chloride (2 mL/1 mL). This solution is treated with ethoxycarbonyl isocyanate (30 μL). The mixture is stirred at room temperature for 1 h, then concentrated. Preparative layer chromatography of the residue on a silica gel plate eluted with 5% methanol in methylene chloride affords 14α-ehtoxycarbonylaminocarbonylmarcfortine A (25 mg). $^1$H NMR (300 MHz, CDCl$_3$) 8.80 (br, 1H, NH), 7.50 (s, NH), 6.80 (d, J=8.1 Hz, $C_4$—H), 6.68 (d, J=8.1 Hz, $C_5$—H), 6.37 (d, J=7.7 Hz, $C_{24}$—H), 5.42 (t, J=2.5 Hz, $C_{14}$—H), 4.92 (d, J=7.7 Hz, $C_{25}$—H), 4.24 (q, 2H, J=7.1 Hz, O-CH$_2$), 3.72 (d, J=11.8 Hz, 1 $C_{12}$—H), 3.13 (s, 3H, N-Me), 3.08 (t, J=10.2 Hz, $C_{20}$—H), 2.6–2.8 (m, 2H), 2.5–2.1 (m, 5H), 2.0–1.5 (m, 5H), 1.44 (s, 6H, $C_{27}$—H & $C_{28}$—H), 1.28 (t, 3H, J=7.1 Hz, OCH$_2$-CH$_3$), 1.12 (s, 3H), 0.88 (s, 3H).

EXAMPLE 9
Synthesis of 14α-hydroxy-N(1)-acetylmarcfortine A (Formula 28)

Potassium hydride (70 mg of a 50% oil dispersion) is added to a solution of 14α-hydroxymarcfortine A (40 mg) in 3 mL of dry tetrahydrofuran. The solution is stirred at room temperature for 1 h then actic anhydride (50 μL) is added. The mixture is stirred at room temperature for 1 h then partitioned between 5% aqueous sodium bicarbonate (3 mL) and methylene chloride (3 mL). The layers are separated and the aqueous layer extracted with methylene chloride (3 mL). The combined extracts are dried with magnesium sulfate, filtered, and evaporated under vacuum. Preparative layer chromatography of the residue on a silica gel plate eluted with 5% methanol in methylene chloride affords 14α-hydroxy-N(1)-acetylmarcfortine A (10 mg). $^1$H NMR (300 MHz, CDCl$_3$) δ 6.88 (q, J 8.1 Hz, $C_4$—H & $C_5$—H), 6.37 (d, J=7.7 Hz, $C_{24}$—H), 4.09 (br, $C_{14}$—H), 4.86 (d, J =7.7 Hz, $C_{25}$—H), 3.23 (d, J =11.3 Hz, 1 $C_{12}$—H), 3.11 (s, 3H, N-Me), 3.0–1.5 (m, 12H), 2.61 (s, 3H, N-acetyl), 1.44 & 1.46 (2s, 6H, $C_{27}$—H & $C_{28}$—H), 1.08 (s, 3H), 0.82 (s, 3H).

EXAMPLE 10
Synthesis of 14α-O-(10-undecenoyl)marcfortine A (Formula 29)

14α-Hydroxymarcfortine A (33 mg) is dissolved in acetonitrile/methylene chloride (4 mL/2mL). This solution is treated with 10-undecenoyl chloride (40 μL), triethyl amine (40 μL) and 4-dimethylaminopyridine (18 mg). The miture is refluxed for 16 h and cooled to room tempature. It is then partitioned between 5% aqueous sodium bicarbonate (3 mL) and methylene chloride (3 mL). The layers are separated and the aqueous layer extracted with methylene chloride (3 mL). The combined extracts are dried with magnesium sulfate, filtered, and evaporated under vacuum. Preparative layer chromatography of the residue on a silica gel plate eluted with 5% methanol in methylene chloride affords 14α-O-(10-undecenoyl)marcfortine A (7 mg). $^1$H NMR (300 MHz, CDCl$_3$) δ 8 8.42 (s, NH), 6.80 (d, J=8.1 Hz, $C_4$—H), 6.68 (d, J=8.1 Hz, $C_5$—H), 6.35 (d, J=7.7 Hz, $C_{24}$—H), 5.78 (m, 1H), 5.44 (br, $C_{14}$—H), 4.89–5.0 (m, 3H), 3.74 (d, J=11.8 Hz, 1 $C_{12}$—H), 3.12 (s, 3H, N—Me), 3.05 (t, J=10.2 Hz, $C_{20}$—H), 2.6–2.8 (m, 2H), 2.9–1.2 (m, 28H), 1.44 (s, 6H, $C_{27}$—H & $C_{28}$—H), 1.11 (s, 3H), 0.82 (s, 3H).

EXAMPLE 11
Preparation of 14α-hydroxy-14β-vinylmarcfortine A (Formula 30)

A solution of 14-ketomarcfortine A (200 mg, 0.4 mmol) in THF (5 mL) at −78° is treated with a solution of vinylmagnesium bromide (1M, 4.0 mL, 4 mmol) in THF at −78°. The resulting mixture is stirred for 2 h at −78° and warmed to room temperature. It is stirred at room temperature for 2h. The reaction is quenched by adding 10% Na$_2$CO$_3$ (3 mL). The mixture was diluted with CH$_2$Cl$_2$ (30 mL), washed with saturated ammonium chloride solution, dried (MgSO$_4$), and concentrated. The residue is subjected to silica gel chromatography (6:4 hexane:acetone) to give 14α-hydroxy-14β-vinylmarcfortine A (120 mg, 60%, R$_f$=0.45) as a white solid. $^1$H NMR (300 MHz, CDCl$_3$) δ 7.86 (s, NH), 6.78 & 6.67 (d, J=8.1 Hz, $C_4$—H & $C_5$—H), 6.32 (d, J=7.7 Hz, $C_{24}$—H), 6.58 (dd, J=17.4, 10.9 Hz, 1H, vinyl), 5.43 (d, J=17.4 Hz, 1H, vinyl), 5.18 (d, J=10.9 Hz, 1H, vinyl), 4.89 (d, J=7.7 Hz, $C_{25}$—H), 3.7 (br, 1H), 3.11 (s, 3H, N—Me), 2.95 (t, 1H, $C_{20}$—H), 2.8–1.5 (m, 12H), 1.44 (s, 6H, $C_{27}$—H & $C_{28}$—H), 1.08 (s, 3H), 0.82 (s, 3H). MS (FAB) M/Z [M+H]: 520

EXAMPLE 12
Synthesis of 14α-O-morpholinocarbonyl-N(1)-morpholinocarbonylmarcfortine A (Formula 31)

Potassium hydride (50 mg of a 50% oil dispersion) is added to a solution of 14α-hydroxymarcfortine A (25 mg) in 3 mL of dry tetrahydrofuran. The solution is stirred at room temperature for 1 h then actic anhydride (30 μL) is added. The mixture is stirred at room temperature for 3 h then partitioned between 5% aqueous sodium bicarbonate (3 mL) and methylene chloride (3 mL). The layers are separated and the aqueous layer extracted with methylene chloride (3 mL). The combined extracts are dried with magnesium sulfate, filtered, and evaporated under vacuum. Preparative layer chromatography of the residue on a silica gel plate eluted with 5% methanol in methylene chloride affords 14α-O-morpholninocarbonyl-N(1)-morpholinocarbonylmarcfortine A (17 mg). $^1$H NMR (300 MHz, CDCl$_3$) δ 6.84 (q, J=8.1 Hz, C$_4$—H & C$_5$—H), 6.41 (d, J=7.7 Hz, C$_{24}$—H), 3.8–3.2 (m, 17H), 2.98 (s, 3H, N—Me), 3.0–1.5 (m, 13H), 1.45 (s, 6H, C$_{27}$—H & C$_{28}$—H), 1.41 (s, 3H, C$_{14}$—Me), 1.18 (s, 3H), 0.83 (s, 3H).

EXAMPLE 13

Preparation of 14α-hydroxy-14β-methylmarcfortine A N-oxide (Formula 32)

A solution of 14α-hydroxymarcfortine A (30 mg) in CH$_2$Cl$_2$ (3 mL) is treated with m-chloroperoxybenzoic acid (20 mg) at 0°. After the mixture is stirred for 0.5 h, then partitioned between 5% aqueous sodium bicarbonate (10 mL) and methylene chloride (20 mL). The layers are separated and the aqueous layer extracted with methylene chloride (10 mL). The combined extracts are dried with magnesium sulfate, filtered, and evaporated under vacuum at 0°, treated with triethyl amine (30 μL) and concentrated to produce the title compound as a solid (20 mg). $^1$H NMR (300 MHz, CD$_3$OD) δ 6.91 & 6.70 (d, J=8.1 Hz, C$_4$—H & C$_5$—H), 6.36 (d, J=7.7 Hz, C$_{24}$—H), 4.91 (d, J=7.7 Hz, C$_{25}$—H), 4.08 & 3.76 (AB q, J=12.9 Hz, 2H, C$_{12}$—H), 3.5–3.1 (m, 4H), 3.12 (s, 3H, N—Me), 2.8–1.6 (m, 7H), 1.46 & 1.44 (2s, 6H, C$_{27}$—H & C$_{28}$—H), 1.50 (s, 3H, C$_{14}$—Me), 1.20 (s, 3H), 0.93 (s, 3H).

EXAMPLE 14

Synthesis of 14α-hydroxy-14β-methyl-N(1)-acetylmarcfortine A (Formula 33)

Potassium hydride (50 mg of a 50% oil dispersion) is added to a solution of 14α-hydroxy-14β-methylmarcfortine A (25 mg) in 3 mL of dry tetrahydrofuran. The solution is stirred at room temperature for 1 h then actic anhydride (50 μL) is added. The mixture is stirred at room temperature for 1 h then partitioned between 5% aqueous sodium bicarbonate (3 mL) and methylene chloride (3 mL). The layers are separated and the aqueous layer extracted with methylene chloride (3 mL). The combined extracts are dried with magnesium sulfate, filtered, and evaporated under vacuum. Preparative layer chromatography of the residue on a silica gel plate eluted with 5% methanol in methylene chloride affords 14α-hydroxy-14β-methyl-N(1)-acetylmarcfortine A (20 mg). $^1$H NMR (300 MHz, CDCl$_3$) δ 6.88 (q, J=8.1 Hz, C$_4$—H & C$_5$—H), 6.37 (d, J=7.7 Hz, C$_{24}$—H), 4.86 (d, J=7.7 Hz, C$_{25}$—H), 3.68 (d, 1 C$_{12}$—H), 3.11 (s, 3H, N—Me), 2.9–2.7 (m, 2H), 2.61 (s, 3H, N-acetyl), 2.5–1.5 (m, 10H), 1.47 & 1.46 (2s, 6H, C$_{27}$—H & C$_{28}$—H), 1.50 (s, 3H, C$_{14}$—Me), 1.08 (s, 3H), 0.82 (s, 3H).

Preparation of 14α-hydroxy-15α-methyl-17-ketomarcfortine A (Formula 34)

A solution of 14α-hydroxy-15,16-dehydro-17-ketomarcfortine A (Formula 9a, 300 mg) in THF (12 mL) is treated with a solution of methylmagnesium bromide (3M, 1.0 mL, 5 equiv.) at room temperature. The resulting mixture is refluxed for 1.5 h then cooled to room temperature. The reaction is quenched by adding saturated ammonium chloride (3 mL). The mixture was diluted with CH$_2$Cl$_2$ (30 mL), washed with saturated ammonium chloride solution, dried (MgSO$_4$), and concentrated. The residue is subjected to silica gel chromatography (1:20 meOH:methylene chloride) to give 14α-hydroxy-15α-methylmarcfortine A (90 mg, 30%) as a white solid. $^1$H NMR (300 MHz, CDCl$_3$) δ 7.90 (s, NH), 6.80 & 6.70 (d, J=8.1 Hz, C$_4$—H & C$_5$—H), 6.32 (d, J=7.7 Hz, C$_{24}$—H), 4.89 (d, J=7.7 Hz, C$_{25}$—H), 4.36 (br, 1H, C$_{14}$—H), 3.74 (br, 2H, C$_{12}$—H), 3.20 (t, 1H, C$_{20}$—H), 3.06 (s, 3H, N—Me), 2.78 & 2.10 (d, 2H, J=15.8 Hz, C$_{10}$—H), 2.5–1.8 (m, 5H), 1.46 & 1.44 (2s, 6H, C$_{27}$—H & C$_{28}$—H), 1.13 (d, 3H, C$_{15}$—Me), 1.12 (s, 3H), 0.88 (s, 3H).

Alternatively, the title compound can be prepared by using lithium dimethyl cuprate reagent. To copper iodide (0.4 g, 0.002 mol) in THF at 0° C. is added methyl lithium (1.4M, 9 mL, 0.013 mol) dropwise. The resulting pale yellow mixture is stirred for 15 minuties then treated dropwise with 14α-hydroxy-15,16-dehydro-17-ketomarcfortine A (Formula 9a, 0.5 g, 0.001 mol) in THF (12 mL) at 0° C. Following 15 minutes of stirring the turbid orange mixture is quenched with saturated ammonium chloride (25 mL) and extracted into EtOAc (30 ML). The organic extract was dried (MgSO4), filtered, and concentrated to give crude material which was purified by a chromatotron (4 mm plate, 4% MeOH/CH$_2$Cl$_2$) to yield product (0.23 g, 44%) as a white solid.

EXAMPLE 15

Preparation of 14α-hydroxy-15α-methylmarcfortine A (Formula 35)

14α-Hydroxy-15α-methyl-17-ketomarcfortine A (90 mg, 0.18 mmol) is dissolved in THF (10 mL) and treated with borane dimethyl sulfide complex (12M, 0.18 mL) at 0°. The mixture is stirred for 2 h at 0°, then MeOH (0.4 mL) is added and stirred for an additional 1 h. After the solvent is evaporated, the residue is subjected to silica gel chromatography (30:70 acetone:methylene chloride) to give 14α-hydroxy-15α-methylmarcfortine A (20 mg) as a solid. $^1$H NMR (300 MHz, CDCl$_3$) δ 8.39 (s, NH), 6.79 & 6.70 (d, J=8.1 Hz, C$_4$—H & C$_5$—H), 6.36 (d, J=7.7 Hz, C$_{24}$—H), 4.91 (d, J=7.7 Hz, C$_{25}$—H), 3.81 (br, 1H, C$_{14}$—H), 3.67 (d, 1H, J=11.7 Hz, C$_{12}$—H), 3.03 (t, 1H, C$_{20}$—H), 3.11 (s, 3H, N—Me), 2.68 & 1.86 (d, 2H, J=15.7 Hz, C$_{10}$—H), 2.7–1.2 (m, 8H), 1.44 (2s, 6H, C$_{27}$—H & C$_{28}$—H), 1.02 (d, 3H, J=6.8 Hz, C$_{15}$—Me), 1.11 (s, 3H), 0.85 (s, 3H). HRMS (FAB) M/Z [M+H] calculated for C$_{29}$H$_{37}$N$_3$O$_5$+H: 508.2811; measured: 508.2840

Preparation of 14,17-diketo-15α-methylmarcfortine A (Formula 36)

A solution of oxalyl chloride (40 μL) in anhydrous CH$_2$Cl$_2$ (5 mL) is treated with DMSO (45 μL) at −78°. The mixture is stirred for 1 h at −78°. A solution of 14α-hydroxy-15α-methyl-17-ketomarcfortine A (27 mg) in CH$_2$Cl$_2$ (2 mL) is added dropwise. The reaction mixture is stirred 20 min at −78°. Triethylamine (0.3 mL) is added to the reaction mixture which is allowed to warm to room temperature during 20 min. The mixture is partitioned between 10% Na$_2$CO$_3$ (10 mL) and CH$_2$Cl$_2$ (10 mL). The organic layer is dried (MgSO$_4$) and concentrated. The residue is subjected to silica gel chromatography (1:20 MeOH:CH$_2$Cl$_2$) to give 14,17-Diketomarcfortine A (22 mg, 80%) as a white solid. The structure of the product can be confirmed by NMR spectroscopy and mass spectrometry. HRMS (FAB) M/Z [M+H] calculated for C$_{28}$H$_{31}$N$_3$O$_6$+H: 506.2291; measured: 506.2280.

Preparation of 14α-hydroxy-14β-methyl-15α-methyl-17-ketomarcfortine A (Formula 37)

A solution of 14,17-Diketo-15α-methylmarcfortine A (25 mg, 0.05 mmol) in CH$_2$Cl$_2$ (5 mL) at −78° is treated with a solution of methylmagnesium bromide (3 M, 0.2 mL, 0.6 mmol) in Et$_2$O at −78°. The resulting mixture is stirred for 0.5 h at −78°. The reaction is quenched by adding 10% Na$_2$CO$_3$ (a few drops). The mixture was diluted with CH$_2$Cl$_2$ (10 mL), dried (MgSO$_4$), and concentrated. The residue is subjected to silica gel chromatography (1:25 MeOH:CH$_2$Cl$_2$) to give 14α-hydroxy-14β-methyl-15α-methyl-17-ketomarcfortine A (16 mg, 62%) as a white solid.

¹H NMR (300 MHz, CDCl₃) δ 8.13 (s, 1H), 6.78 (d, 1H), 6.70 (d, 1H), 6.33 (d, 1H), 4.91 (d, 1H), 3.75 (q, 2H), 3.16 (t, 1H), 3.05 (s, 3H), 2.78 (d, 1H), 2.68–2.57 (m, 1H), 2.42–2.0 (m, 6H), 1.64 (s, 3H), 1.45 (s, 3H), 1.44 (s, 3H), 1.11 (s, 3H), 1.04 (d, 3H), 0.92 (d, 3H).

EXAMPLE 16

Preparation of 14α-hydroxy-14β-methyl-15α-methylmarcfortine A (Formula 38)

14α-Hydroxy-14β-methyl-15α-methyl-17-ketomarcfortine A (15 mg, 0.028 mmol) is dissolved in THF (10 mL) and treated with borane dimethyl sulfide complex (10M, 0.02 mL) at 0°. The mixture is stirred for 2 h at 0°, then MeOH (0.4 mL) is added and stirred for an additional 1 h. After the solvent is evaporated, the residue is subjected to silica gel chromatography (30:70 acetone: methylene chloride) to give 14α-hydroxy-14β-methyl-15α-methylmarcfortine A (4 mg, 29%) as a solid. ¹H NMR (300 MHz, CDCl₃) δ 7.82 (s, 1H), 6.79 (d, 1H), 6.67 (d, 1H), 6.33 (d, 1H), 4.90 (d, 1H), 3.65 (d, 1H), 3.09 (s, 3H), 2.98 (t, 1H), 2.69 (d, 1H), 2.60–2..22 (m, 7H), 2.06 (dd, 1H), 1.87 (d, 1H), 1.85–1.75 (m, 1H), 1.44 (s, 6H), 1.43 (s, 3H), 1.10 (s, 3H), 0.94 (d, 3H), 0.86 (s,3H).

Suitable C-24, C-25, N-1 and N-18a substituted marcfortine A, B, C, and D derivatives for starting materials in the above sequence of reactions are readily prepared by the procedures given in U.S. Pat. No. 4,923,867. The reactions are conducted in a suitable inert solvent such as pyridine, collidine, toluene (preferred), xylene, dioxane, tetrahydrofuran, and the like, at temperatures from 10° to 180° preferably 80° to 140°.

Alternatively, the C-24, C-25 and N-1 derivatives can be prepared from the marcfortines. For example, a large series of marcfortine analogs can be prepared by alkylation of N-1 of the N-18a substituted marcfortines. These derivatives may be easily prepared by sequential treatment of a solution of marcfortine A, N-18a-substituted marcfortine B, or N-18a-substituted marcfortine C in an aprotic organic solvent such as tetrahydrofuran, ether, benzene and the like with an excess of a strong base such as potassium hydride (preferred), sodium hydride, butyllithium, potassium tert-butoxide, and the like followed by a suitable alkylating agent at temperatures ranging from 0° C. to 50° C. for 0.25 to 48 hours. Suitable alkylating agents include alkyl bromides, alkyl iodides, alkyl sulfonates, alkenyl iodides, alkynyl bromides, alkoxyalkyl chlorides, and the like.

An additional series of derivatives can be generated by modification of the C24-C25 double bond of marcfortines A, B and C. The 24,25-dihydro analogs are readily prepared by stirring a solution of the appropriate marcfortine in an alcoholic solvent such as methanol, ethanol, propanol and the like with a catalyst such as palladium, platinum, tris (triphenylphosphine)-chlororhodium and the like in the presence of hydrogen gas. The product, which is a 24,25-dihydromarcfortine analog, can be isolated and purified by using techniques known to those skilled in the art. Note that the reactions described above for modification of other portions of the marcfortine structure may also be applied to 24,25-dihydro marcfortine analogs to prepare the corresponding 24,25-dihydro analogs. Additional G ring modified analogs of the marcfortines may be prepared via the 24,25-dibromide which is easily prepared by treating a solution of a marcfortine in a halogenated solvent such as dichloromethane, chloroform, carbon tetrachloride and the like with 1 molar equivalent of bromine at temperatures ranging from −20° C. to 25° C. for 0.25 to 8 hours. This process affords the corresponding 24,25-dibromo 24,25-dihydromarcfortine derivative which can be isolated and purified by using techniques known to those skilled in the art. Note that the 24,25-dichloro analog may be prepared by substituting chlorine for bromine in the process described above. The 24,25-dibromo-24,25-dihydro-marcfortine analogs described above are useful intermediates for the preparation of additional derivatives. Thus, treatment of a solution of the dibromide in an alcoholic solvent such as methanol, ethanol, propanol, and the like with a strong base such as 1,8-diazabicyclo[5.4.0]undec-7-ene (DBU) at temperatures ranging from 0° C. to 30° C. for 0.25 to 24 hours affords 24-alkoxy-25 bromo-24,25 dihydro-marcfortine analogs which can be isolated and purified by using techniques known to those skilled in the art. These 24-alkoxy, 25-bromo derivatives can be debrominated by treatment of a solution of the compound in an aprotic organic solvent such as benzene, toluene, hexane, and the like with a tin hydride reducing agent such as tributyltin hydride, triphenyltin hydride and the like with or without the addition of a initiator radical such as azobis-isobutyronitrile (AIBN) at temperatures ranging from 25° C. to 120° C. for 0.5 to 48 hours. This process affords the corresponding 24-alkoxymarcfortine derivatives ($R_{24}$=lower alkoxy in the general structure) which can be isolated and purified by using techniques known to those skilled in the art.

*Haemonchus contortus/Trichostrongylus colubriformis/* Jird Assay

This in vivo assay utilizes jirds infected with two important target parasites of ruminants, *H. contortus* and *T. colubriformis* (anthelmintic-sensitive or -resistant worms can be used). Initially, activity is assessed only against *H. contortus* as described in G. A. Conder et al., J. Parasitol. 76, 168–170 (1990), while follow-up studies examine activity against both species of parasites using the techniques outlined in G. A. Conder et al., J. Parasitol. 77, 621–623 (1991). The activity of 14α-hydroxymarcfortine A, 14α-hydroxy-14β-methylmarcfortine A, 14β-hydroxymarcfortine A, 14α-hydroxymarcfortine A N-oxide, and marcfortine D is set forth in Table I.

TABLE I

Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.

| Compound | Purity | Dose (mg/jird) | n (survived to necropsy) | Percentage Clearance | |
|---|---|---|---|---|---|
| | | | | *H. contortus* | *T. colubriformis* |
| marcfortine A | 100 % | 0.33 | 3(3) | 97–100 | 99–100 |
| marcfortine D | 100% | 1.0 | 3(3) | 0 | 72 |

TABLE I-continued

Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.

| Example 1. | 100% | 0.11 | 3(3) | 99–100 | 99–100 |
|---|---|---|---|---|---|
| Example 2. | 100% | 0.33 | 3(3) | 100 | 100 |
| Example 3. | 100% | 1.0 | 3(3) | 54 | 41 |
| Example 4. | 100% | 0.33 | 3(3) | 100 | 99 |
| Example 5. | 100% | 0.33 | 3(3) | 88–99 | 99–100 |
| Example 6. | 100% | 0.33 | 3(3) | 100 | 100 |
| Example 7. | 100% | 0.11 | 3(3) | 100 | 100 |
| Example 8. | 100% | 0.33 | 3(3) | 98–99 | 100 |
| Example 9. | 100% | 0.11 | 3(3) | 100 | 99 |
| Example 10. | 100% | 0.11 | 3(3) | 98–99 | 100 |
| Example 11. | 100% | 0.33 | 3(3) | 92–98 | 94–96 |
| Example 12. | 100% | 0.33 | 3(3) | 100 | 99 |
| Example 13. | 100% | 0.33 | 3(3) | 98–100 | 97–99 |
| Example 14. | 100% | 0.33 | 3(3) | 99–100 | 100 |
| Example 15. | 100% | 0.11 | 3(3) | 98 | 99 |
| Example 16. | 100% | 0.33 | 3(3) | 80 | 100 |

CHART A

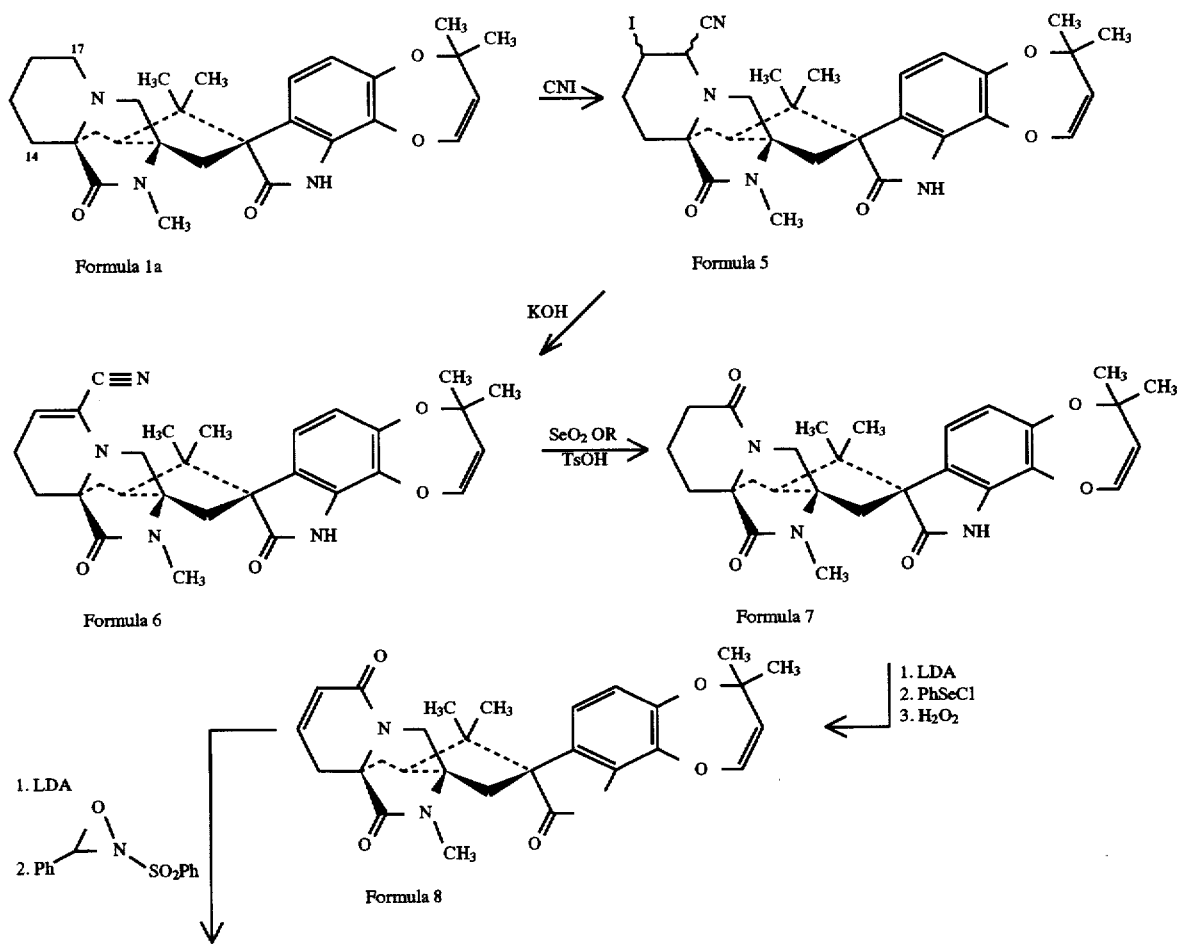

TABLE I-continued
Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.
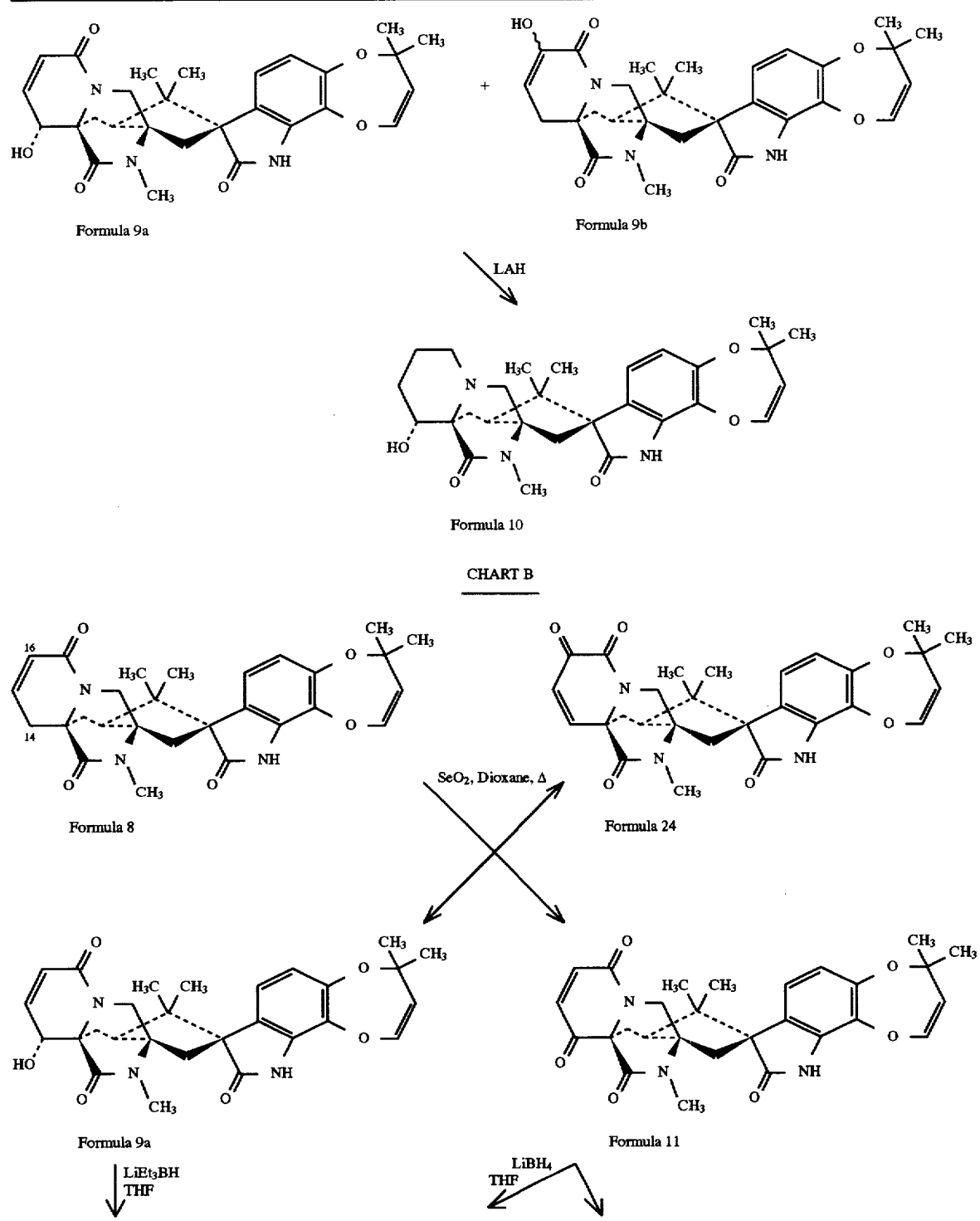

TABLE I-continued
Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.
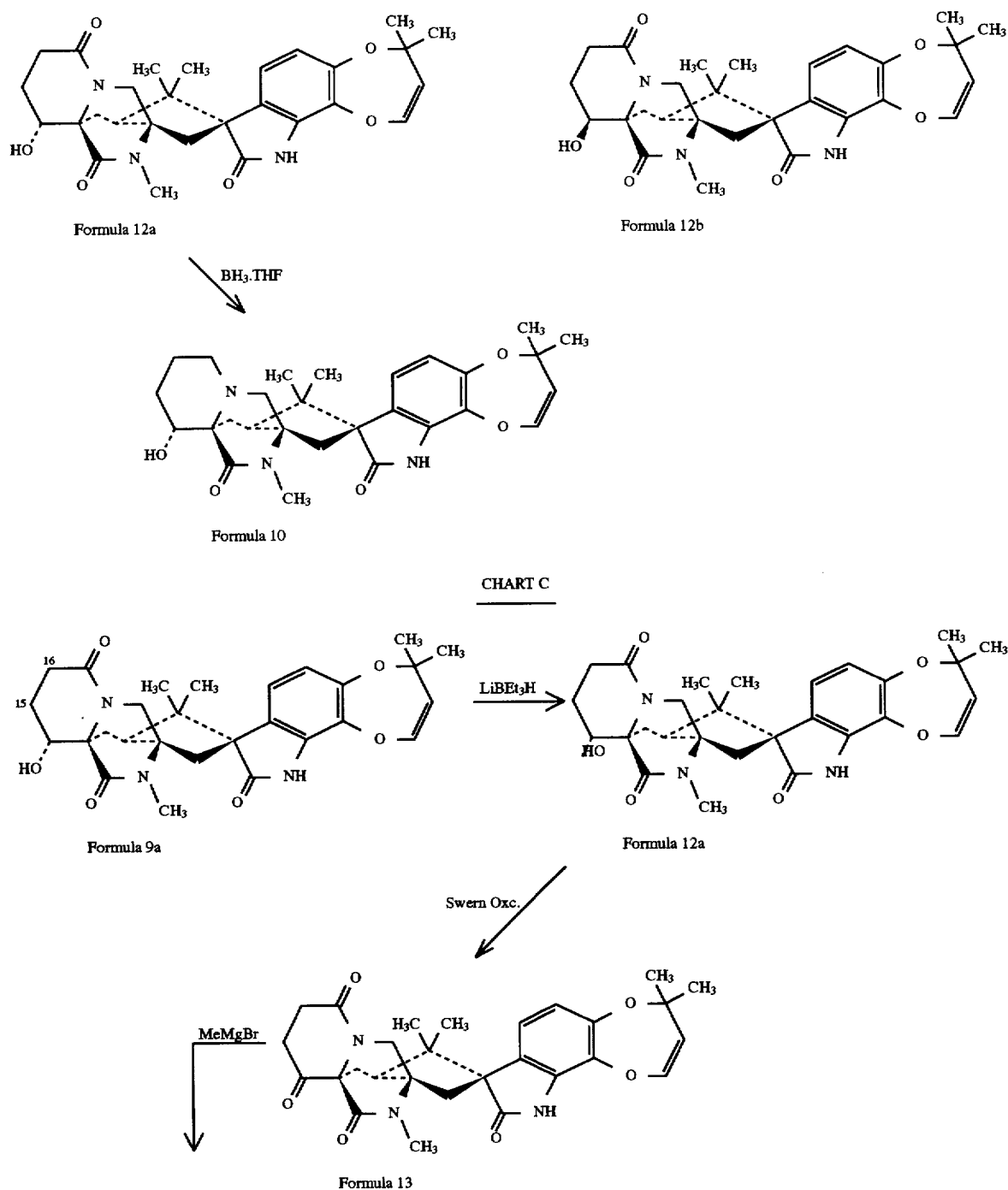

TABLE I-continued
Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.
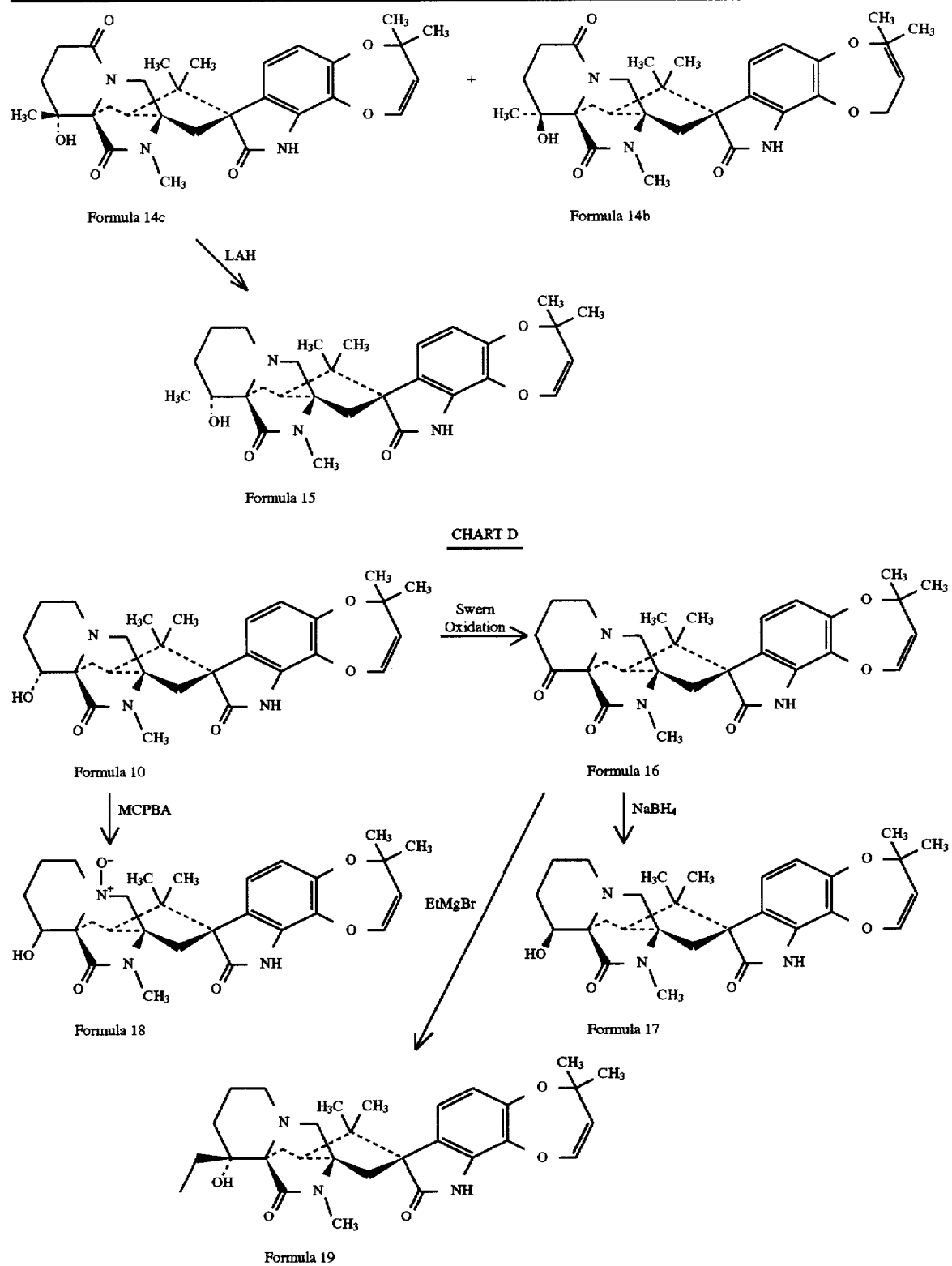
CHART D TABLE I-continued
Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.
CHART E
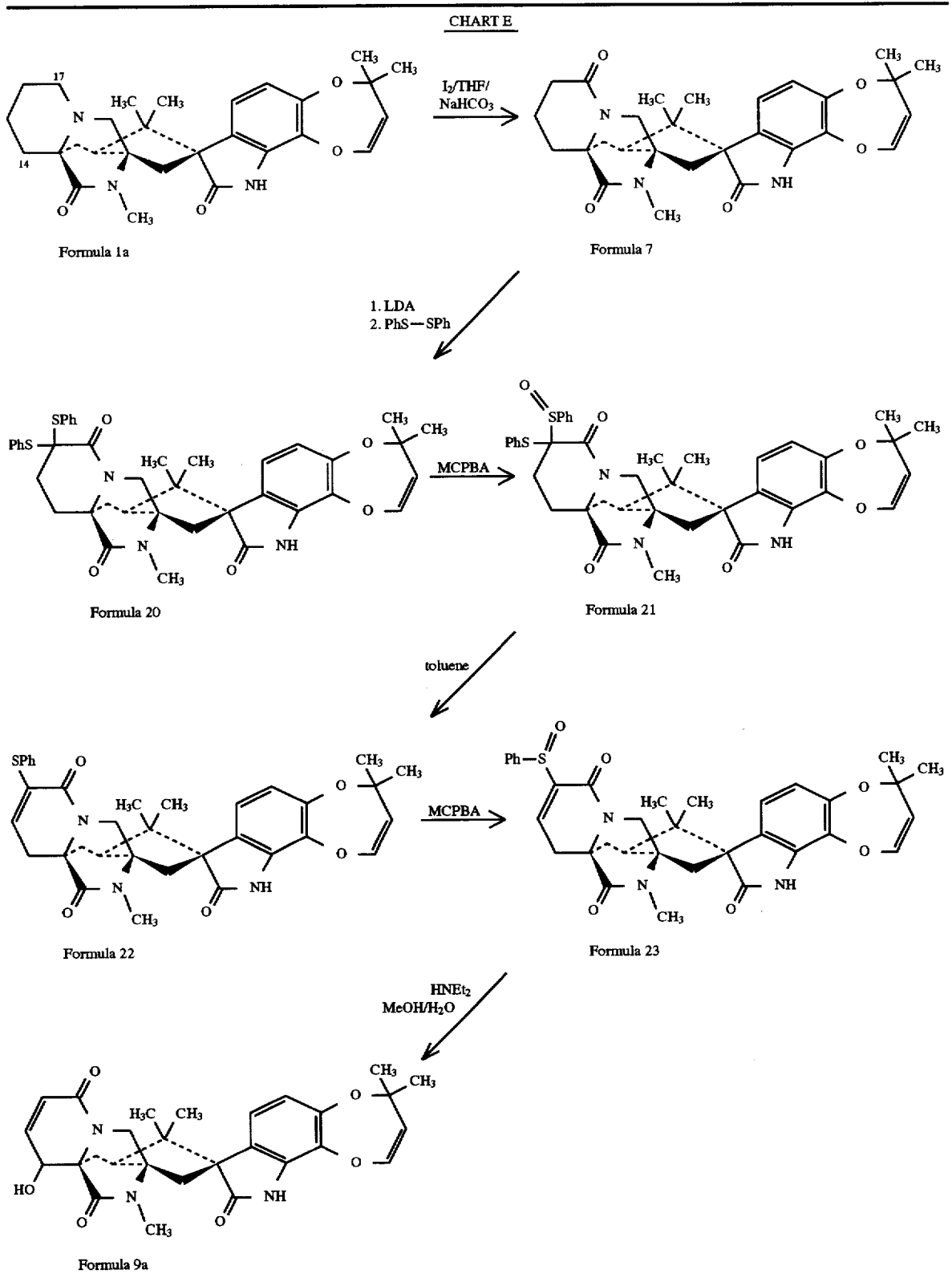

TABLE I-continued
Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.
CHART F
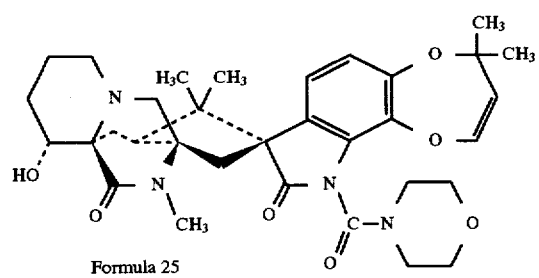
Formula 25
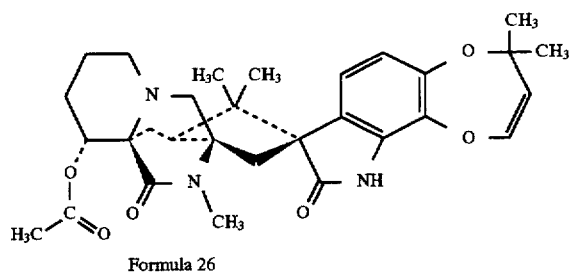
Formula 26
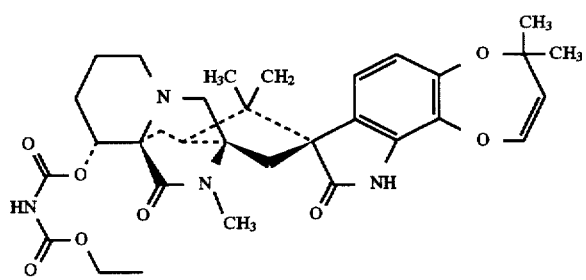
Formula 27
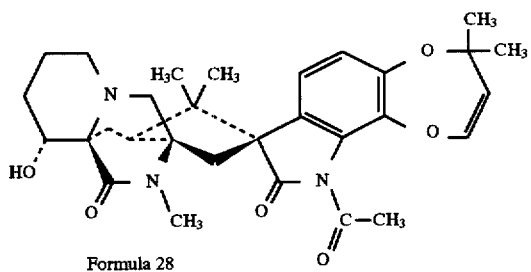
Formula 28
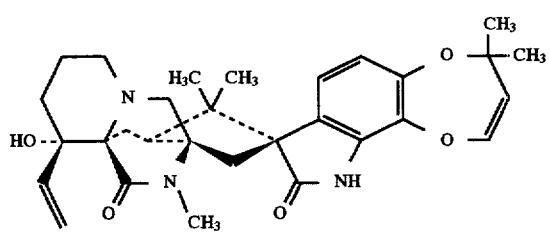
Formula 29
Formula 30

TABLE I-continued
Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.
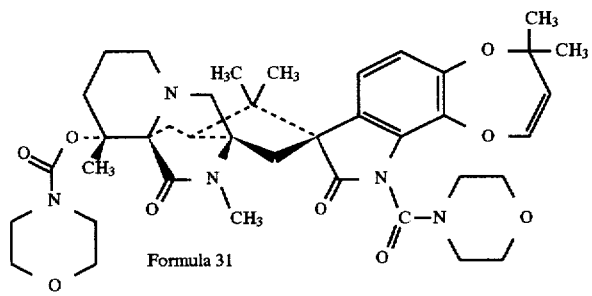
Formula 31
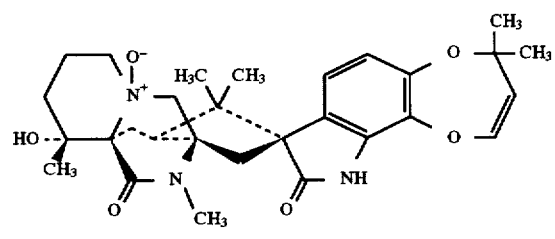
Formula 32
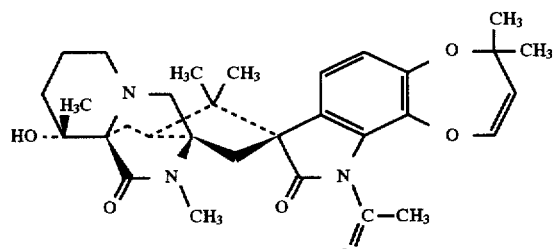
Formula 33
CHART G
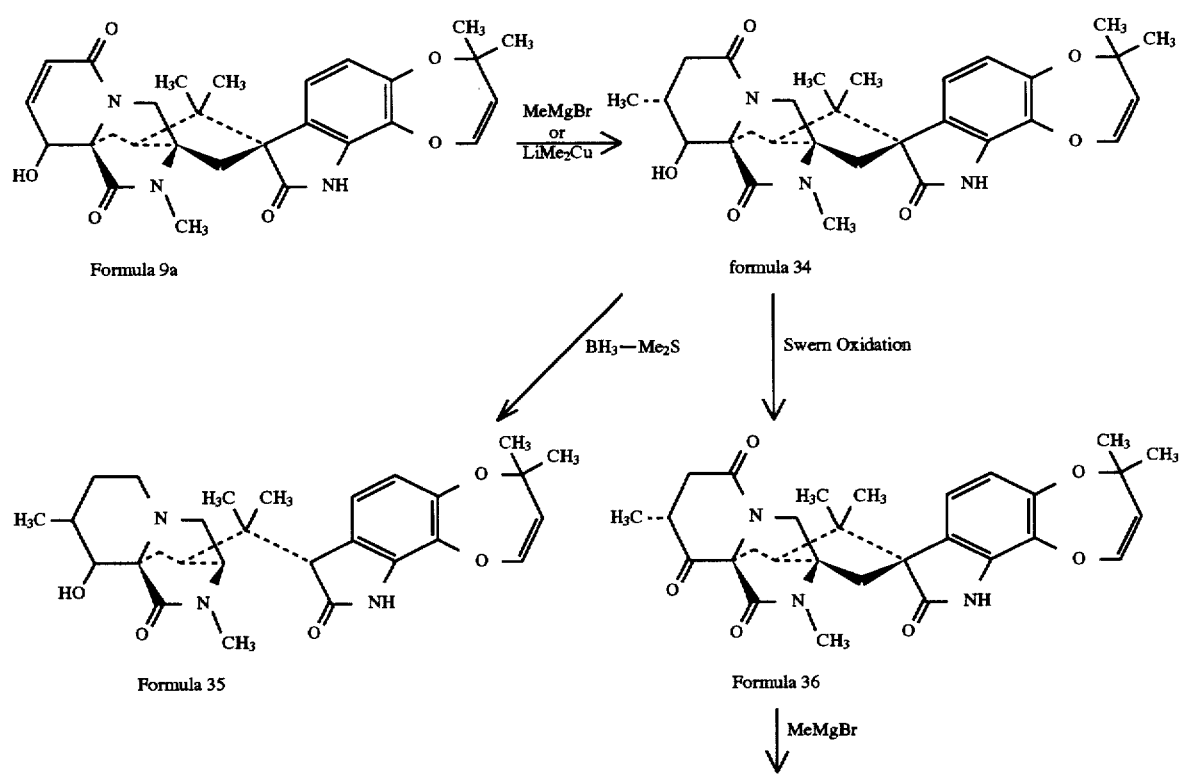

TABLE I-continued

Percentage Clearance of *Haemonchus contortus* and *Trichostrongylus colubriformis* from jirds inoculated per os with ~1,000 exsheathed, infective larvae of each parasite, treated per os with testing compounds on day 10 postinoculation (PI) and necropsied on day 13 post inoculation.

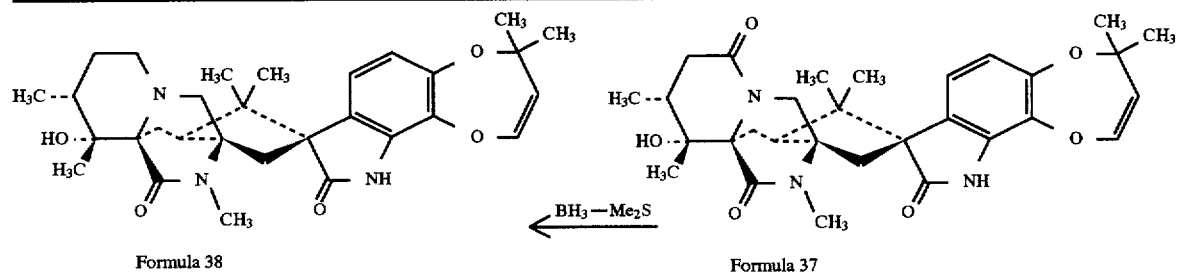

Formula 38          Formula 37

I claim:
1. A compound of Formula I

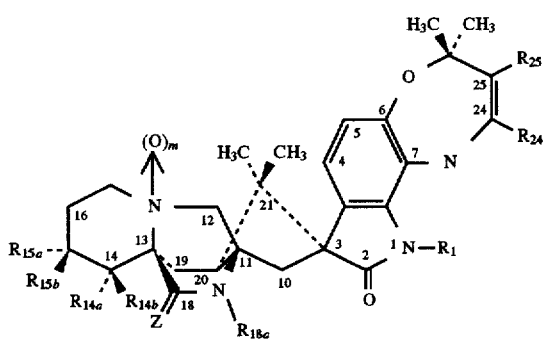

or a pharmaceutically acceptable salt, or 12α-N-oxide thereof;
wherein:
m is 0 or 1;
Z is O or S;
R$_1$ is hydrogen, C$_1$–C$_7$ alkyl, cyclo C$_3$–C$_8$alkyl, benzyl, C$_2$–C$_7$ alkanoyl (—C(O)C$_2$—C$_7$alkyl) {optionally substituted with carboxy (—COOH), C$_1$–C$_7$ alkanoyl, carboC$_1$–C$_7$alkoxy (—C(O)OC$_1$–C$_7$alkyl), —NR$_4$R$_5$, aminocarbonyl (—C(O)NR$_4$R$_5$)}, C$_{10}$–C$_{24}$alkanoyl (—C(O)C$_{10}$–C$_{24}$alkyl, cyclo C$_3$–C$_8$alkanoyl {optionally substituted with carboxy, C$_1$–C$_7$ alkanoyl, carboC$_1$–C$_7$alkoxy, —NR$_4$R$_5$, aminocarbonyl}, alkanoyloxymethylene (—CH$_2$OC(O)-C$_{2-C7}$alkyl), benzoyloxymethlene (—CH$_2$OC(O)phenyl) {optionally substituted with 1 or 2 groups selected from halogen, C$_1$–C$_4$ alkyl, haloC$_1$–C$_7$alkyl, nitro, cyano and C$_1$–C$_7$alkoxy }, C$_{10}$–C$_{24}$alkenoyl (—C(O)C$_9$–C$_{23}$alkenyl), benzenesulfonyl (—SO$_2$CH$_2$phenyl) {optionally substituted with 1 or 2 groups selected from halogen, C$_1$–C$_4$ alkyl, haloC$_1$–C$_7$alkyl, nitro, cyano and C$_1$–C$_7$alkoxy}, C$_1$–C$_4$alkylaminocarbonyl (—C(O)N(C$_1$–C$_4$alkyl)$_2$), C$_1$–C$_4$alkylaminothiocarbonyl (—C(S)N(C$_1$–C$_4$alkyl)$_2$), C$_1$–C$_7$ alkoxycarbonyl, phenoxycarbonyl {optionally substituted with 1 or 2 groups selected from halogen, C$_1$–C$_4$ alkyl, haloC$_1$–C$_7$alkyl, nitro, cyano and C$_1$–C$_7$alkoxy}, —C(O)NR'$_4$R'$_5$, —P(=X)(R$_2$)(R$_3$), —SR$_6$, —SO$_2$NR$_4$R5, benzoyl substituted at the 3 or 4 position with —CH$_2$NR$_4$R$_5$ or bicycloC$_8$–C$_{12}$alkanoyl;
R$_4$ and R$_5$, being the same or different, are selected from hydrogen, C$_1$–C$_7$ alkyl, phenyl {optionally substituted with 1 or 2 groups selected from halogen, C$_{1-4}$ alkyl, haloC$_1$–C$_7$alkyl, nitro, cyano and C$_1$–C$_7$alkoxy};
R'$_4$ and R'$_5$, being the same or different, are selected from C$_1$–C$_7$ alkyl, cyclo(C$_3$–C$_8$)alkyl, phenyl {optionally substituted with 1 or 2 groups selected from halogen, C$_{1-4}$ alkyl, haloC$_1$–C$_7$alkyl, nitro, cyano and C$_1$–C$_7$alkoxy};
X is O or S;
R$_2$ and R$_3$, being the same or different, are selected from C$_1$–C$_7$ alkyl, phenyl {optionally substituted with 1 or 2 groups selected from halogen, C$_{1-4}$ alkyl, haloC$_1$–C$_7$alkyl, nitro, cyano and C$_1$–C$_7$alkoxy}, C$_1$–C$_7$ alkoxy, thio(C$_1$–C$_7$)alkoxy, phenoxy, thiophenoxy, —NR$_7$R$_8$ {where R$_7$ and R$_8$, being the same or different, are selected from H or C$_1$–C$_7$ alkyl;
R$_6$ is C$_1$–C$_7$ alkyl, haloC$_1$–C$_7$alkyl, carboC$_1$–C$_7$alkoxy, —NR$_9$R$_{10}$ o where R$_9$ and R$_{10}$, being the same or different, are C$_1$–C$_7$ alkyl or phenyl (optionally substituted with 1 or 2 groups selected from halo, lower alkyl, haloC$_1$–C$_7$alkyl, nitro, cyano, C$_1$–C$_7$ alkoxy);
R$_{24}$ is hydrogen, halogen or C$_1$–C$_7$ alkoxy;
R$_{25}$ is hydrogen or halogen;
R18a is hydrogen, C$_1$–C$_7$ alkyl, C$_2$–C$_8$ alkoxyalkyl, C$_2$–C$_8$ alkenyl, C$_2$–C$_8$ alkynyl or benzyl;
R14a is hydroxyl, hydrogen, C$_1$–C$_7$ alkyl, C$_2$–C$_8$ alkoxyalkyl, cyclo(C$_3$–C$_8$)alkyl or benzyl (optionally substituted with 1 or 2 groups selected from halo, lower alkyl, haloC$_1$–C$_7$alkyl, nitro, cyano, C$_1$–C$_7$ alkoxy);
R$_{14b}$is hydroxyl, hydrogen, C$_1$–C$_7$ alkoxy, cyclo(C$_3$–C$_8$) alkyl or benzoxyl (optionally substituted with 1 or 2 groups selected from halo, lower alkyl, haloC$_1$–C$_7$alkyl, nitro, cyano, C$_1$–C$_7$ alkoxy);
R$_{15}$a and R$_{15b}$ are both hydrogen, with the provisio that when one of R$_{14a}$ or R$_{14b}$ is hydroxyl and the other is hydrogen or methyl, R$_{15a}$ and R$_{15b}$ can be hydrogen or methyl; and with the overall proviso that R$_{14a}$ and R$_{14b}$ are not both hydrogen.

2. A compound according to claim 1 where m is 0.
3. A compound according to claim 2 where R$_{24}$ and R$_{25}$ are hydrogen; and R$_{18a}$ is hydrogen, C$_1$–C$_7$ alkyl, C$_1$–C$_8$ alkoxymethyl, C$_2$–C$_8$ alkenyl or benzyl.
4. A compound according to claim 1 where Z is an oxygen atom.
5. A compound according to claim 4 where R$_{24}$ and R$_{25}$ are hydrogen; and R$_{18a}$ is hydrogen, C$_1$–C$_7$ alkyl, C$_1$–C$_8$ alkoxymethyl, C$_2$–C$_8$ alkenyl or benzyl.
6. A compound according to claim 1 where Z is a sulfur atom.

7. A compound according to claim 6 where $R_{24}$ and $R_{25}$ are hydrogen; and $R_{18a}$ is hydrogen, $C_1$–$C_7$ alkyl, $C_1$–$C_8$ alkoxymethyl, $C_2$–$C_8$ alkenyl or benzyl.

8. A compound which is selected from the group consisting of 1-acetoxymethyl-14α-hydroxymarcfortine A;
1-diethoxyphosphoryl-14α-hydroxymarcfortine A;
1-dimethylsulfamoyl-14α-hydroxymarcfortine A;
1-cyclopropylcarbonyl-14α-hydroxymarcfortine A;
2-bicyclo[2.2.1]heptanoyl-14α-hydroxymarcfortine A;
1-succinoyl-14α-hydroxymarcfortine A;
1-(2,4-dinitrobenzenesulfenyl)-14α-hydroxymarcfortine A;
1-(p-toluenesulfonyl)-14α-hydroxymarcfortine A;
1-acetyl-14α-hydroxymarcfortine A;
1-methyl-14α-hydroxymarcfortine A;
1-benzyl-14α-hydroxymarcfortine A;
1-dimethylcarbamoyl-14α-hydroxymarcfortine A;
1-methoxycarbonyl-14α-hydroxymarcfortine A;
14α-hydroxymarcfortine B;
1-(p-toluenesulfonyl)-14α-hydroxymarcfortine B;
1-ethyl-14α-hydroxymarcfortine B;
1-benzyl-14α-hydroxymarcfortine B;
18a-ethyl-14α-hydroxymarcfortine B;
18a-benzyl-14α-hydroxymarcfortine B;
18a-methoxyethoxymethyl-14α-hydroxymarcfortine B;
18a-allyl-14α-hydroxymarcfortine B;
18a-propargyl-14α-hydroxymarcfortine B;
1,18a-bis-ethyl-14α-hydroxymarcfortine B;
1,18a-bis-benzyl-1 4-hydroxymarcfortine B;
18a-ethyl-24-methoxy-14α-hydroxymarcfortine B;
1-palmitoyl-14α-hydroxymarcfortine A;
1-acetoxymethyl-14α-hydroxy-14β-methylmarcfortine A;
1-diethoxyphosphoryl-14α-hydroxy-14β-methylmarcfortine A;
1-dimethylsulfamoyl-14α-hydroxy-14β-methylmarcfortine A;
1-cyclopropylcarbonyl-14α-hydroxy-14β-methylmarcfortine A;
2-bicyclo [2.2.1]heptanoyl-14α-hydroxy-14β-methylmarcfortine A;
1-succinoyl-14α-hydroxy-14β-methylmarcfortine A;
1-(2,4-dinitrobenzenesulfenyl)-14α-hydroxy-14β-methylmarcfortine A;
1-(p-toluenesulfonyl)-14α-hydroxy-14β-methylmarcfortine A;
1-acetyl-14α-hydroxy-14β-methylmarcfortine A;
1-methyl-14α-hydroxy-14β-methylmarcfortine A;
1-benzyl-14α-hydroxy-14β-methylmarcfortine A;
1-dimethylcarbamoyl-14α-hydroxy-14β-methylmarcfortine A;
1-methoxycarbonyl-14α-hydroxy-14β-methylmarcfortine A;
14α-hydroxy-14β-methylmarcfortine B;
1-(p-toluenesulfonyl)-14α-hydroxy-14β-methylmarcfortine B;
1-ethyl-14α-hydroxy-14β-methylmarcfortine B;
1-benzyl-14α-hydroxy-14β-methylmarcfortine B;
18a-ethyl-14α-hydroxy-14β-methylmarcfortine B;
18a-benzyl-14α-hydroxy-14β-methylmarcfortine B;
18a-methoxyethoxymethyl-14α-hydroxy-14β-methylmarcfortine B;
18α-allyl-14α-hydroxy-14β-methylmarcfortine B;
18a-propargyl-14α-hydroxy-14β-methylmarcfortine B;
1,18a-bis-ethyl-14α-hydroxy-14β-methylmarcfortine B;
1,18a-bis-benzyl-14α-hydroxy-14β-methylmarcfortine B;
18a-ethyl-24-methoxy-14α-hydroxy-14β-methylmarcfortine B;
1-palmitoyl-14α-hydroxy-1 4β-methylmarcfortine A;
1-acetoxymethyl-14α-hydroxy-14β-ethylmarcfortine A;
1-diethoxyphosphoryl-14α-hydroxy-14β-ethylmarcfortine A;
1-dimethylsulfamoyl-14α-hydroxy-14β-ethylmarcfortine A;
1-cyclopropylcarbonyl-14α-hydroxy-14β-ethylmarcfortine A;
2-bicyclo[2.2.1]heptanoyl-14α-hydroxy-14β-ethylmarcfortine A;
1-succinoyl-14α-hydroxy-14β-ethylmarcfortine A;
1-(2,4-dinitrobenzenesulfenyl)-14α-hydroxy-14β-ethylmarcfortine A;
1-(p-toluenesulfonyl)-14α-hydroxy-14β-ethylmarcfortine A;
1-acetyl-14α-hydroxy-14β-ethylmarcfortine A;
1-methyl-14α-hydroxy-14β-ethylmarcfortine A;
1-benzyl-14α-hydroxy-14β-ethylmarcfortine A;
1-dimethylcarbamoyl-14α-hydroxy-14β-ethylmarcfortine A;
1-methoxycarbonyl-14α-hydroxy-14β-ethylmarcfortine A;
14α-hydroxy-14β-ethylmarcfortine B;
1-(p-toluenesulfonyl)-14α-hydroxy-14β-ethylmarcfortine B;
1-ethyl-14α-hydroxy-14β-ethylmarcfortine B;
1-benzyl-14α-hydroxy-14β-ethylmarcfortine B;
18a-ethyl-14α-hydroxy-14β-ethylmarcfortine B;
18a-benzyl-14α-hydroxy-14β-ethylmarcfortine B;
18a-methoxyethoxymethyl-14α-hydroxy-14β-ethylmarcfortine B;
18a-allyl-14α-hydroxy-14β-ethylmarcfortine B;
18a-propargyl-14α-hydroxy-14β-ethylmarcfortine B;
1,18a-bis-ethyl-14α-hydroxy-14β-ethylmarcfortine B;
1,18a-bis-benzyl-14α-hydroxy-14β-ethylmarcfortine B;
18a-ethyl-24-methoxy-14α-hydroxy-14β-ethylmarcfortine B;
1-palmitoyl-14α-hydroxy-14β-ethylmarcfortine A;
1-acetoxymethyl-14β-methylmarcfortine A;
1-diethoxyphosphoryl-14β-methylmarcfortine A;
1-dimethylsulfamoyl-14β-methylmarcfortine A;
1-cyclopropylcarbonyl-14β-methylmarcfortine A;
2-bicyclo[2.2.1]heptanoyl-14β-methylmarcfortine A;
1-succinoyl-14β-methylmarcfortine A;
1-(2,4-dinitrobenzenesulfenyl)-14β-methylmarcfortine A;
1-(p-toluenesulfonyl)-14β-methylmarcfortine A;
1-acetyl-14β-methylmarcfortine A;

1-methyl-14β-methylmarcfortine A;
1-benzyl-14β-methylmarcfortine A;
1-dimethylcarbamoyl-14β-methylmarcfortine A;
1-methoxycarbonyl-14β-methylmarcfortine A;
14β-methylmarcfortine B;
1-(p-toluenesulfonyl)-14β-methylmarcfortine B;
1-ethyl-14β-methylmarcfortine B;
1-benzyl-14β-methylmarcfortine B;
18a-ethyl-14β-methylmarcfortine B;
18a-benzyl-14β-methylmarcfortine B;
18a-methoxyethoxymethyl-14β-methylmarcfortine B;
18a-allyl-14β-methylmarcfortine B;
18a-propargyl-14β-methylmarcfortine B;
1,18a-bis-ethyl-14β-methylmarcfortine B;
1,18a-bis-benzyl-14β-methylmarcfortine B;
18a-ethyl-24-methoxy-14β-methylmarcfortine B;
1-palmitoyl-14β-methylmarcfortine A;
1-acetoxymethyl-14β-ethylmarcfortine A;
1-diethoxyphosphoryl-14β-ethylmarcfortine A;
1-dimethylsulfamoyl-14β-ethylmarcfortine A;
1-cyclopropylcarbonyl-14β-ethylmarcfortine A;
2-bicyclo[2.2.1]heptanoyl-14β-ethylmarcfortine A;
1-succinoyl-14β-ethylmarcfortine A;
1-(2,4-dinitrobenzenesulfenyl)-14β-ethylmarcfortine A;
1-(p-toluenesulfonyl)-14β-ethylmarcfortine A;
1-acetyl-14β-ethylmarcfortine A;
1-methyl-14β-ethylmarcfortine A;
1-benzyl-14β-ethylmarcfortine A;
1-dimethylcarbamoyl-14β-ethylmarcfortine A;
1-methoxycarbonyl-14β-ethylmarcfortine A;
14β-ethylmarcfortine B;
1-(p-toluenesulfonyl)-14β-ethylmarcfortine B;
1-ethyl-14β-ethylmarcfortine B;
1-benzyl-14β-ethylmarcfortine B;
18α-ethyl-14β-ethylmarcfortine B;
18a-benzyl-14β-ethylmarcfortine B;
18a-methoxyethoxymethyl-14β-ethylmarcfortine B;
18a-allyl-14β-ethylmarcfortine B;
18a-propargyl-14β-ethylmarcfortine B;
1,18a-bis-ethyl-14β-ethylmarcfortine B;
1,18a-bis-benzyl-14β-ethylmarcfortine B;
18a-ethyl-24-methoxy-14β-ethylmarcfortine B;
1-palmitoyl-14β-ethylmarcfortine A;
1-acetoxymethyl-14α-O-methylmarcfortine A;
14α-O-methylmarcfortine A;
14α-O-methyl-14α-methylmarcfortine A;
14α-O-methyl-14α-ethylmarcfortine A;
1-diethoxyphosphoryl-14α-O-methylmarcfortine A;
1-dimethylsulfamoyl-14α-O-methylmarcfortine A;
1-cyclopropylcarbonyl-14α-O-methylmarcfortine A;
2-bicyclo[2.2.1]heptanoyl-14α-O-methylmarcfortine A;
1-succinoyl-14α-O-methylmarcfortine A;
1-(2,4-dinitrobenzenesulfenyl)-14α-O-methylmarcfortine A;
1-(p-toluenesulfonyl)-14α-O-methylmarcfortine A;
1-acetyl-14α-O-methylmarcfortine A;
1-methyl-14α-O-methylmarcfortine A;
1-benzyl-14α-O-mehtylmarcfortine A;
1-dimethylcarbamoyl-14α-O-methylmarcfortine A;
1-methoxycarbonyl-14α-O-methylmarcfortine A;
14α-O-methylmarcfortine B;
1-(p-toluenesulfonyl)-14α-O-methylmarcfortine B;
1-ethyl-14α-O-methylmarcfortine B;
1-benzyl-14α-O-methylmarcfortine B;
18a-ethyl-14α-O-methylmarcfortine B;
18a-benzyl-14α-O-methylmarcfortine B;
18a-methoxyethoxymethyl-14α-O-methylmarcfortine B;
18a-allyl-14α-O-methylmarcfortine B;
18a-propargyl-14α-O-methylmarcfortine B;
1,18a-bis-ethyl-14α-O-methylmarcfortine B;
1,18a-bis-benzyl-14α-O-methylmarcfortine B;
18a-ethyl-24-methoxy-14α-O-methylmarcfortine B;
1-palmitoyl-14α-O-methylmarcfortine A;
1-acetoxymethyl-14α-O-methyl-14β-methylmarcfortine A;
1-diethoxyphosphoryl-14α-O-methyl-14β-methylmarcfortine A;
1-dimethylsulfamoyl-14α-O-methyl-14β-methylmarcfortine A;
1-cyclopropylcarbonyl-14α-O-methyl-14β-methylmarcfortine A;
2-bicyclo[2.2.1]heptanoyl-14α-O-methyl-14β-methylmarcfortine A;
1-succinoyl-14α-O-methyl-14β-methylmarcfortine A;
1-(2,4-dinitrobenzenesulfenyl)-14α-O-methyl-14β-methylmarcfortine A;
1-(p-toluenesulfonyl)-14α-O-methyl-14β-methylmarcfortine A;
1-acetyl-14α-O-methyl-14β-methylmarcfortine A;
1-methyl-14α-O-methyl-14β-methylmarcfortine A;
1-benzyl-14α-O-methyl-14β-methylmarcfortine A;
1-dimethylcarbamoyl-14α-O-methyl-14β-methylmarcfortine A;
1-methoxycarbonyl-14α-O-methyl-14β-methylmarcfortine A;
14α-O-methyl-14β-methylmarcfortine B;
1-(p-toluenesulfonyl)-14α-O-methyl-14β-methylmarcfortine B;
1-ethyl-14α-O-methyl-14β-methylmarcfortine B;
1-benzyl-14α-O-methyl-14β-methylmarcfortine B;
18a-ethyl-14α-O-methyl-14β-methylmarcfortine B;
18a-benzyl-14α-O-methyl-14β-methylmarcfortine B;
18a-methoxyethoxymethyl-14α-O-methyl-14β-methylmarcfortine B;
18a-allyl-14α-O-methyl-14β-methylmarcfortine B;
18a-propargyl-14α-O-methyl-14β-methylmarcfortine B;
1,18a-bis-ethyl-14α-O-methyl-14β-methylmarcfortine B;
1,18a-bis-benzyl-14α-O-methyl-14β-methylmarcfortine B;
1,18a-ethyl-24-methoxy-14α-O-methyl-14β-methylmarcfortine B;
1-palmitoyl-14α-O-methyl-14β-methylmarcfortine A;
1-acetoxymethyl-14α-O-methyl-14β-ethylmarcfortine A;
1-diethoxyphosphoryl-14α-O-methyl-14β-ethylmarcfortine A;
1-dimethylsulfamoyl-14α-O-methyl-14β-ethylmarcfortine A;

1-cyclopropylcarbonyl-14α-O-methyl-14β-ethylmarcfortine A;
2-bicyclo[2.2.1]heptanoyl-14α-O-methyl-14β-ethylmarcfortine A;
1-succinoyl-14αα-O-methyl-14β-ethylmarcfortine A;
1-(2,4-dinitrobenzenesulfenyl)-14α-O-methyl-14β-ethylmarcfortine A;
1-(p-toluenesulfonyl)-14α-O-methyl-14β-ethylmarcfortine A;
1-acetyl-14α-O-methyl-14β-ethylmarcfortine A;
1-methyl-14α-O-methyl-14β-ethylmarcfortine A;
1-benzyl-14α-O-methyl-14β-ethylmarcfortine A;
1-dimethylcarbamoyl-14α-O-methl-14β-ethylmarcfortine A;
1-methoxycarbonyl-14α-O-methyl-14β-ethylmarcfortine A;
14α-O-methyl-14β-ethylmarcfortine B;
1-(p-toluenesulfonyl)-14α-O-methyl-14β-ethylmarcfortine B;
1-ethyl-14α-O-methyl-14β-ethylmarcfortine B;
1-benzyl-14α-O-methyl-14β-ethylmarcfortine B;
18a-ethyl-14α-O-methyl-14β-ethylmarcfortine B;
18a-benzyl-14α-O-methyl-14β-ethylmarcfortine B;
18a-methoxyethoxymethyl-14α-O-methyl-14β-ethylmarcfortine B;
18a-allyl-14α-O-methyl-14β-ethylmarcfortine B;
18a-propargyl-14α-O-methyl-14β-ethylmarcfortine B;
1,18a-bis-ethyl-14α-O-methyl-14β-ethylmarcfortine B;
1,18a-bis-benzyl-14α-O-methyl-14β-ethylmarcfortine B;
18a-ethyl-24-methoxy-14α-O-methyl-14β-ethylmarcfortine B;
1-palmitoyl-14α-O-methyl-14β-ethylmarcfortine A;
1-acetoxymethyl-14α-O-allylmarcfortine A;
14α-O-allylmarcfortine A;
14α-O-allyl-14β-methylmarcfortine A;
14α-O-allyl-14β-ethylmarcfortine A;
1-diethoxyphosphoryl-14α-O-allylmarcfortine A;
1-dimethylsulfamoyl-14α-O-allylmarcfortine A;
1-cyclopropylcarbonyl-14α-O-allylmarcfortine A;
2-bicyclo[2.2.1]heptanoyl-14α-O-allylmarcfortine A;
1-succinoyl-14α-O-allylmarcfortine A;

1-(2,4-dinitrobenzenesulfenyl)-14α-O-allylmarcfortine A;

1-(p-toluenesulfonyl)-14α-O-allylmarcfortine A;

1-acetyl-14α-O-allylmarcfortine A;

1-methyl-14α-O-allylmarcfortine A;

1-benzyl-14α-O-allylmarcfortine A;

1-dimethylcarbamoyl-14α-O-allylmarcfortine A;

1 -methoxycarbonyl-14α-O-allylmarcfortine A;

14α-O-allylmarcfortine B;

1-(p-toluenesulfonyl)-14α-O-allylmarcfortine B;

1-ethyl-14α-O-allylmarcfortine B;

1-benzyl-14α-O-allylmarcfortine B;

18a-ethyl-14α-O-allylmarcfortine B;

18a-benzyl-14α-O-allylmarcfortine B;

18a-methoxyethoxymethyl-14α-O-allylmarcfortine B;

18a-allyl-14α-O-allylmarcfortine B;

18a-propargyl-14α-O-allylmarcfortine B;

1,18a-bis-ethyl-14α-O-allylmarcfortine B;

1,18a-bis-benzyl-14α-O-allylmarcfortine B;

18a-ethyl-24-methoxy-14α-O-allylmarcfortine B;

1-palmitoyl-14α-O-allylmarcfortine A;

1-acetoxymethyl-14α-O-allyl-14β-methylmarcfortine A;

1-diethoxyphosphoryl-14α-O-allyl-14β-methylmarcfortine A;

1-dimethylsulfamoyl-14α-O-allyl-14β-methylmarcfortine A;

1-cyclopropylcarbonyl-14α-O-allyl-14β-methylmarcfortine A;

2-bicyclo[2.2.1]heptanoyl-14α-O-allyl-14β-methylmarcfortine A;

1-succinoyl-14α-O-allyl-14β-methylmarcfortine A;

1-(2,4-dinitrobenzenesulfenyl)-14α-O-allyl-14β-methylmarcfortine A;

1-(p-toluenesulfonyl)-14α-O-allyl-14β-methylmarcfortine A;

1-acetyl-14α-O-allyl-14β-methylmarcfortine A;

1-methyl-14α-O-allyl-14β-methylmarcfortine A;

1-benzyl-14α-O-allyl-14β-methylmarcfortine A;

1-dimethylcarbamoyl-14α-O-allyl-14β-methylmarcfortine A;

1-methoxycarbonyl-14α-O-allyl-14β-methylmarcfortine A;

14α-O-allyl-14β-methylmarcfortine B;

1-(p-toluenesulfonyl)-14α-O-allyl-14β-methylmarcfortine B;

1-ethyl-14α-O-allyl-14β-methylmarcfortine B;

1 -benzyl-14α-O-allyl-14β-methylmarcfortine B;

18a-ethyl-14α-O-allyl-14β-methylmarcfortine B;

18a-benzyl-14α-allyl-14β-methylmarcfortine B;

18a-methoxyethoxymethyl-14α-allyl-14β-methylmarcfotine B;

18a-allyl-14α-allyl-14β-methylmarcfortine B;

18a-propargyl-14α-O-allyl-14β-methylmarcfortine B;

1,18a-bis-ethyl-14α-O-allyl-14β-methylmarcfortine B;

1,18a-bis-benzyl-14α-O-allyl-14β-methylmarcfortine B;

18a-ethyl-24-methoxy-14α-O-allyl-14β-methylmarcfortine B;

1-palmitoyl-14α-O-allyl-14β-methylmarcfortine A;

1-acetoxymethyl-14α-O-allyl-14β-ethylmarcfortine A;

1-diethoxyphosphoryl-14α-O-allyl-14β-ethylmarcfortine A;

1-dimethylsulfamoyl-14α-O-allyl-14β-ethylmarcfortine A;

1-cyclopropylcarbonyl-14α-O-allyl-14β-ethylmarcfortine A;

2-bicyclo[2.2.1]heptanoyl-14α-O-allyl-14β-ethylmarcfortine A;

1-succinoyl-14α-O-allyl-14β-ethylmarcfortine A;

1-(2,4-dinitrobenzenesulfenyl)-14α-O-allyl-14β-ethylmarcfortine A;

1-(p-toluenesulfonyl)-14α-O-allyl-14β-ethylmarcfortine A;

1-acetyl-14αα-O-allyl-14β-ethylmarcfortine A;

1-methyl-14α-O-allyl-14β-ethylmarcfortine A;

1-benzyl-14α-O-allyl-14β-ethylmarcfortine A;

1-dimethylcarbamoyl-14α-O-allyl-14β-ethylmarcfortine A;

1-methoxycarbonyl-14α-O-allyl-14β-ethylmarcfortine A;
14α-O-allyl-14β-ethylmarcfortine B;
1-(p-toluenesulfonyl)-14α-O-allyl-14β-ethylmarcfortine B;
1-ethyl-14α-O-allyl-14β-ethylmarcfortine B;
1-benzyl-14α-O-allyl-14β-ethylmarcfortine B;
18a-ethyl-14α-O-allyl-14β-ethylmarcfortine B;
18α-benzyl-14α-O-allyl-14β-ethylmarcfortine B;
18α-methoxyethoxymethyl-14α-O-allyl-14β-ethylmarcfortine B;
18α-allyl-14α-O-allyl-14β-ethylmarcfortine B;
18a-propargyl-14α-O-allyl-14β-ethylmarcfortine B;
1,18a -bis-ethyl-14α-O-allyl-14β-ethylmarcfortine B;
1,18a-bis-benzyl-14α-O-allyl-14β-ethylmarcfortine B;
18a-ethyl-24-methoxy-14α-O-allyl-14β-ethylmarcfortine B;
1-palmitoyl-14α-O-allyl-14β-ethylmarcfortine A;
14α-hydroxy-14β-methyl-1 5α-methylmarcfortine A;
1-acetoxymethyl-14α-hydroxy-14β-methyl-15α-methylmarcfortine A;
1-diethoxyphosphoryl-14α-hydroxy-14β-methyl-15α-methylxymarcfortine A;
1-dimethylsulfamoyl-14α-hydroxy-14β-methyl-15α-methylmarcfortine A;
1-cyclopropylcarbonyl-14α-hydroxy-14β-methyl-15α-methylmarcfortine A;
2-bicyclo[2.2.1]heptanoyl-14α-hydroxy-14β-methyl-15α-methylmarcfortine A;
1-succinoyl-14αα-hydroxy-14β-methyl-15α-methylmarcfortine A;
1-(2,4-dinitrobenzenesulfenyl)-14α-hydroxy-14β-methyl-15α-methylmarcfortine A;
1-(p-toluenesulfonyl)-14α-hydroxy-14β-methyl-15α-methylmarcfortine A;
1-acetyl-14α-hydroxy-14β-methyl-15α-methylmarcfortine A;
1-methyl-14α-hydroxy-14β-methyl-15α-methylmarcfortine A;
1-benzyl-14α-hydroxy-14β-methyl-15α-methylmarcfortine A;
1-dimethylcarbamoyl-14α-hydroxy-14β-methyl-15α-methylmarcfortine A;
1-methoxycarbonyl-14α-hydroxy-14β-methyl-15α-methylmarcfortine A;
14α-hydroxy-14β-methyl-15α-methylmarcfortine B;
1-(p-toluenesulfonyl)-14α-hydroxy-14β-methyl-15α-methylmarcfortine B;
1-ethyl-14α-hydroxy-14β-methyl-15α-methylmarcfortine B;
1-benzyl-14α-hydroxy-14β-methyl-15α-methylmarcfortine B;
18a-ethyl-14α-hydroxy-14β-methyl-15α-methylmarcfortine B;
18a-benzyl-14α-hydroxy-14β-methyl-15α-methylmarcfortine B;
18a-methoxyethoxymethyl-14-hydroxy-14β-methyl-15α-methylmarcfortine B;
18a-allyl-14α-hydroxy-14β-methyl-15α-methylmarcfortine B;
18a-propargyl-14α-hydroxy-14β-methyl-15α-methylmarcfortine B;
1,18α-bis-ethyl-14α-hydroxy-14β-methyl-15α-methylmarcfortine B;
1,18α-bis-benzyl-14α-hydroxy-14β-methyl-15α-methylmarcfortine B;
18a-ethyl-24-methoxy-14-hydroxy-14β-methyl-15α-methylmarcfortine B;
1-palmitoyl-14α-hydroxy-14β-methyl-15α-methylmarcfortine A;
14α-hydroxy-15α-methylmarcfortine A;
1-acetoxymethyl-14α-hydroxy-15α-methylmarcfortine A;
1-diethoxyphosphoryl-14α-hydroxy-15α-methylxymarcfortine A;
1-dimethylsulfamoyl-14α-hydroxy-15α-methylmarcfortine A;
1-cyclopropylcarbonyl-14α-hydroxy-15α-methylmarcfortine A;
2-bicyclo[2.2.1]heptanoyl-14α-hydroxy-15α-methylmarcfortine A;
1-succinoyl-14α-hydroxy-15α-methylmarcfortine A;
1-(2,4-dinitrobenzenesulfenyl)-14α-hydroxy-15α-methylmarcfortine A;
1-(p-toluenesulfonyl)-14α-hydroxy-15c-methylmarcfortine A;
1-acetyl-14α-hydroxy-15α-methylmarcfortine A;
1-methyl-14α-hydroxy-15α-methylmarcfortine A;
1-benzyl-14α-hydroxy-15α-methylmarcfortine A;
1-dimethylcarbamoyl-14α-hydroxy-15α-methylmarcfortine A;
1-methoxycarbonyl-14α-hydroxy-15α-methylmarcfortine A;
14α-hydroxy-15α-methylmarcfortine B;
1-(p-toluenesulfonyl)-14α-hydroxy-15α-methylmarcfortine B;
1-ethyl-14α-hydroxy-15α-methylmarcfortine B;
1-benzyl-14α-hydroxy-15α-methylmarcfortine B;
18a-ethyl-14α-hydroxy-15α-methylmarcfortine B;
18a-benzyl-14α-hydroxy-15α-methylmarcfortine B;
18a-methoxyethoxymethyl-14α-hydroxy-15α-methylmarcfortine B;
18a-allyl-14α-hydroxy-15α-methylmarcfortine B;
18a-propargyl-14α-hydroxy-15α-methylmarcfortine B;
1,18a-bis-ethyl-14α-hydroxy-15α-methylmarcfortine B;
1,18a-bis-benzyl-14α-hydroxy-15α-methylmarcfortine B;
18a-ethyl-24-methoxy-14α-hydroxy-15α-methylmarcfortine B;
1-palmitoyl-14α-hydroxy-15α-methylmarcfortine A.

9. A compound according to claim 1 selected from the group consisting of
14α-hydroxy-14β-ethylmarcfortine A;
14α-hydroxy-14β-methylmarcfortine A; or
14α-hydroxy-14α-methyl-15α-methylmarcfortine A.

10. A compound according to claim 1, which is 14α-hydroxymarcfortine A.

11. A compound according to claim 1, which is 14α-hydroxy-15α-methylmarcfortine A.

12. A compound according to claim 1, which is 14α-hydroxy-14β-methylmarcfortine A.

13. A method for the treatment or prevention of helminth or arthropod infections in domesticated animals which comprises treating such animals with an effective amount of a compound of claim 11.

14. A method for the treatment of insect or nematode pests of plants which comprises treating said plants or the soil in which they grow with an effective amount of a compound of claim 1.

15. A composition useful for the treatment and prevention of helminth or arthropod infections of domesticated animals which is comprised of an inert carrier and a compound of claim 1.

16. A composition useful for the prevention and treatment of insect or nematode pests of plants which is comprised of an inert carrier and a compound of claim 1.

17. A compound selected from the group consisiting of:

16-iodo-17-cyanomarcfortine A;
1-acetoxymethyl-16-iodo-17-cyanomarcfortine A;
1-diethoxyphosphoryl-16-iodo-17-cyanomarcfortine A;
1-dimethylsulfamoyl-16-iodo-17-cyanomarcfortine A;
1-cyclopropylcarbonyl-16-iodo-17-cyanomarcfortine A;
2-bicyclo[2.2.1]heptanoyl-16-iodo-17-cyanomarcfortine A;
1-succinoyl-16-iodo-17-cyanomarcfortine A;
1-(2,4-dinitrobenzenesulfenyl)-16-iodo-17-cyanomarcfortine A;
1-(p-toluenesulfonyl)-16-iodo-17-cyanomarcfortine A;
1-acetyl-16-iodo-17-cyanomarcfortine A;
1-methyl-16-iodo-17-cyanomarcfortine A;
1-benzyl-16-iodo-17-cyanomarcfortine A;
1-dimethylcarbamoyl-16-iodo-17-cyanomarcfortine A;
1-methoxycarbonyl-16-iodo-17-cyanomarcfortine A;
16-iodo-17-cyanomarcfortine B;
1-(p-toluenesulfonyl)-16-iodo-17-cyanomarcfortine B;
1-ethyl-16-iodo-17-cyanomarcfortine B;
1-benzyl-16-iodo-17-cyanomarcfortine B;
18a-ethyl-16-iodo-17-cyanomarcfortine B;
18a-benzyl-16-iodo-17-cyanomarcfortine B;
18a-methoxyethoxymethyl-16-iodo-17-cyanomarcfortine B;
18a-allyl-16-iodo-17-cyanomarcfortine B;
18a-propargyl-16-iodo-17-cyanomarcfortine B;
18a-ethyl-24-methoxy-24,25-dihydro-16-iodo-17-cyanomarcfortine B;
1,18a-bis-ethyl-16-iodo-17-cyanomarcfortine B;
1,18a-bis-benzyl-16-iodo-17-cyanomarcfortine B;
18a-ethyl-24-methoxy-16-iodo-17-cyanomarcfortine B;
1-palmitoyl-16-iodo-17-cyanomarcfortine A;
16,17-dehydro-17-cyanomarcfortine A;
1-acetoxymethyl-16,17-dehydro-17-cyanomarcfortine A;
1-diethoxyphosphoryl-16,17-dehydro-17-cyanomarcfortine A;
1-dimethylsulfamoyl-16,17-dehydro-17-cyanomarcfortine A;
1-cyclopropylcarbonyl-16,17-dehydro-17-cyanomarcfortine A;
2-bicyclo[2.2.1]heptanoyl-16,17-dehydro-17-cyanomarcfortine A;
1-succinoyl-16,17-dehydro-17-cyanomarcfortine A;
1-(2,4-dinitrobenzenesulfenyl)-16,17-dehydro-17-cyanomarcfortine A;
1-(p-toluenesulfonyl)-16,17-dehydro-17-cyanomarcfortine A;
1-acetyl-16,17-dehydro-17-cyanomarcfortine A;
1-methyl-16,17-dehydro-17-cyanomarcfortine A;
1-benzyl-16,17-dehydro-17-cyanomarcfortine A;
1-dimethylcarbamoyl-16,17-dehydro-17-cyanomarcfortine A;
1-methoxycarbonyl-16,17-dehydro-17-cyanomarcfortine A;
16,17-dehydro-17-cyanomarcfortine B;
1-(p-toluenesulfonyl)-16,17-dehydro-17-cyanomarcfortine B;
1-ethyl-16,17-dehydro-17-cyanomarcfortine B;
1-benzyl-16,17-dehydro-17-cyanomarcfortine B;
18a-ethyl-16,17-dehydro-17-cyanomarcfortine B;
18a-benzyl-16,17-dehydro-17-cyanomarcfortine B;
18a-methoxyethoxymethyl-16,17-dehydro-17-cyanomarcfortine B;
18a-allyl-16,17-dehydro-17-cyanomarcfortine B;
18a-propargyl-16,17-dehydro-17-cyanomarcfortine B;
18a-ethyl-24-methoxy-24,25-dihydro-16,17-dehydro-17-cyanomarcfortine B;
1,18a-bis-ethyl-16,17-dehydro-17-cyanomarcfortine B;
1,18a-bis-benzyl-16,17-dehydro-17-cyanomarcfortine B;
18a-ethyl-24-methoxy-16,17-dehydro-17-cyanomarcfortine B;
1-palmitoyl-16,17-dehydro-17-cyanomarcfortine A;
17-ketomarcfortine A;
1-acetoxymethyl-17-ketomarcfortine A;
1-diethoxyphosphoryl-17-ketoxymarcfortine A;
1-dimethylsulfamoyl-17-ketomarcfortine A;
1-cyclopropylcarbonyl-17-ketomarcfortine A;
2-bicyclo[2.2.1]heptanoyl-17-ketomarcfortine A;
1-succinoyl-17-ketomarcfortine A;
1-(2,4-dinitrobenzenesulfenyl)-17-ketomarcfortine A;
1-(p-toluenesulfonyl)-17-ketomarcfortine A;
1-acetyl-17-ketomarofortine A;
1-methyl-17-ketomarcfortine A;
1-benzyl-17-ketomarcfortine A;
1-dimethylcarbamoyl-17-ketomarcfortine A;
1-methoxycarbonyl-17-ketomarcfortine A;
17-ketomarcfortine B;
1-(p-toluenesulfonyl)-17-ketomarcfortine B;
1-ethyl-17-ketomarcfortine B;
1-benzyl-17-ketomarcfortine B;
18a-ethyl-17-ketomarcfortine B;
18a-benzyl-17-ketomarcfortine B;
18a-methoxyethoxymethyl-17-ketomarcfortine B;
18a-allyl-17-ketomarcfortine B;
18a-propargyl-17-ketomarcfortine B;
1,18a-bis-ethyl-17-ketomarcfortine B;
1,18a-bis-benzyl-17-ketomarcfortine B;
18a-ethyl-24-methoxy-17-ketomarcfortine B;
1-palmitoyl-17-ketomarcfortine A;
15,16-dehydro-17-ketomarcfortine A;
1-acetoxymethyl-15,16-dehydro-17-ketomarcfortine A;
1-diethoxyphosphoryl-15,16-dehydro-17-ketoxymarcfortine A;
1-dimethylsulfamoyl-15,16-dehydro-17-ketomarcfortine A;

1-cyclopropylcarbonyl-15,16-dehydro-17-ketomarcfortine A;
2-bicyclo[2.2.1]heptanoyl-15,16-dehydro-17-ketomarcfortine A;
1-succinoyl-15,16-dehydro-17-ketomarcfortine A;
1-(2,4-dinitrobenzenesulfenyl)-15,16-dehydro-17-ketomarcfortine A;
1-(p-toluenesulfonyl)-15,16-dehydro-17-ketomarcfortine A;
1-acetyl-15,16-dehydro-17-ketomarcfortine A;
1-methyl-15,16-dehydro-17-ketomarcfortine A;
1-benzyl-15,16-dehydro-17-ketomarcfortine A;
1-dimethylcarbamoyl-15,16-dehydro-17-ketomarcfortine A;
1-methoxycarbonyl-15,16-dehydro-17-ketomarcfortine A;
15,16-dehydro-17-ketomarcfortine B;
1-(p-toluenesulfonyl)-15,16-dehydro-17-ketomarcfortine B;
1-ethyl-15,16-dehydro-17-ketomarcfortine B;
1-benzyl-15,16-dehydro-17-ketomarcfortine B;
18a-ethyl-15,16-dehydro-17-ketomarcfortine B;
18a-benzyl-15,16-dehydro-17-ketomarcfortine B;
18a-methoxyethoxymethyl-15,16-dehydro-17-ketomarcfortine B;
18a-allyl-15,16-dehydro-17-ketomarcfortine B;
18a-propargyl-15,16-dehydro-17-ketomarcfortine B;
1,18a-bis-ethyl-15,16-dehydro-17-ketomarcfortine B;
1,18a-bis-benzyl-15,16-dehydro-17-ketomarcfortine B;
18a-ethyl-24-methoxy-15,16-dehydro-17-ketomarcfortine B;
1-palmitoyl-15,16-dehydro-17-ketomarcfortine A;
14α-hydroxy-15,16-dehydro-17-ketomarcfortine A;
1-acetoxymethyl-14α-hydroxy-15,16-dehydro-17-ketomarcfortine A;
1-diethoxyphosphoryl-14α-hydroxy-15,16-dehydro-17-ketoxymarcfortine A;
1-dimethylsulfamoyl-14α-hydroxy-15,16-dehydro-17-ketomarcfortine A;
1-cyclopropylcarbonyl-14α-hydroxy-15,16-dehydro-17-ketomarcfortine A;
2-bicyclo[2.2.1]heptanoyl-14α-hydroxy-15,16-dehydro-17-ketomarcfortine A;
1-succinoyl-14α-hydroxy-15,16-dehydro-17-ketomarcfortine A;
1-(2,4-dinitrobenzenesulfenyl)-14α-hydroxy-15,16-dehydro-17-ketomarcfortine A;
1-(p-toluenesulfonyl)-14α-hydroxy-15,16-dehydro-17-ketomarcfortine A;
1-acetyl-14α-hydroxy-15,16-dehydro-17-ketomarcfortine A;
1-methyl-14α-hydroxy-15,16-dehydro-17-ketomarcfortine A;
1-benzyl-14α-hydroxy-15,16-dehydro-17-ketomarcfortine A;
1-dimethylcarbamoyl-14α-hydroxy-15,16-dehydro-17-ketomarcfortine A;
1-methoxycarbonyl-14α-hydroxy-15,16-dehydro-17-ketomarcfortine A;
14α-hydroxy-15,16-dehydro-17-ketomarcfortine B;
1-(p-toluenesulfonyl)-14α-hydroxy-15,16-dehydro-17-ketomarcfortine B;
1-ethyl-14α-hydroxy-15,16-dehydro-17-ketomarcfortine B;
1-benzyl-14α-hydroxy-15,16-dehydro-17-ketomarcfortine B;
18a-ethyl-14α-hydroxy-15,16-dehydro-17-ketomarcfortine B;
18a-benzyl-14α-hydroxy-15,16-dehydro-17-ketomarcfortine B;
18a-methoxyethoxymethyl-14α-hydroxy-15,16-dehydro-17-ketomarcfortine B;
18a-allyl-14αα-hydroxy-15,16-dehydro-17-ketomarcfortine B;
18a-propargyl-14α-hydroxy-15,16-dehydro-17-ketomarcfortine B;
1,18a-bis-ethyl-14α-hydroxy-15,16-dehydro-17-ketomarcfortine B;
1,18a-bis-benzyl-14o-hydroxy-15,16-dehydro-17-ketomarcfortine B;
18a-ethyl-24-methoxy-14α-hydroxy-15,16-dehydro-17-ketomarcfortine B;
1-palmitoyl-14α-hydroxy-15,16-dehydro-17-ketomarcfortine A;
14α-hydroxy-17-ketomarcfortine A;
1-acetoxymethyl-14α-hydroxy-17-ketomarcfortine A;
1-diethoxyphosphoryl-14α-hydroxy-17-ketoxymarcfortine A;
1-dimethylsulfamoyl-14α-hydroxy-17-ketomarcfortine A;
1-cyclopropylcarbonyl-14α-hydroxy-17-ketomarcfortine A;
2-bicyclo[2.2.1]heptanoyl-14α-hydroxy-17-ketomarcfortine A;
1-succinoyl-14α-hydroxy-17-ketomarcfortine A;
1-(2,4-dinitrobenzenesulfenyl)-14α-hydroxy-17-ketomarcfortine A;
1-(p-toluenesulfonyl)-14α-hydroxy-17-ketomarcfortine A;
1-acetyl-14α-hydroxy-17-ketomarcfortine A;
1-methyl-14α-hydroxy-17-ketomarcfortine A;
1-benzyl-14α-hydroxy-17-ketomarcfortine A;
1-dimethylcarbamoyl-14α-hydroxy-17-ketomarcfortine A;
1-methoxycarbonyl-14α-hydroxy-17-ketomarcfortine A;
14α-hydroxy-17-ketomarcfortine B;
1-(p-toluenesulfonyl)-14α-hydroxy-17-ketomarcfortine B;
1-ethyl-14α-hydroxy-17-ketomarcfortine B;
1-benzyl-14α-hydroxy-17-ketomarcfortine B;
18a-ethyl-14α-hydroxy-17-ketomarcfortine B;
18a-benzyl-14α-hydroxy-17-ketomarcfortine B;
18a-methoxyethoxymethyl-14α-hydroxy-17-ketomarcfortine B;
18a-allyl-14α-hydroxy-17-ketomarcfortine B;
18a-propargyl-14α-hydroxy-17-ketomarcfortine B;
1,18a-bis-ethyl-14α-hydroxy-17-ketomarcfortine B;
1,18a-bis-benzyl-14α-hydroxy-17-ketomarcfortine B;
18a-ethyl-24-methoxy-14α-hydroxy-17-ketomarcfortine B;

1-palmitoyl-14α-hydroxy-17-ketomarcfortine A;
14,17-diketomarcfortine A;
1-acetoxymethyl-14,17-diketomarcfortine A;
1-diethoxyphosphoryl-14,17-diketoxymarcfortine A;
1-dimethylsulfamoyl-14,17-diketomarcfortine A;
1-cyclopropylcarbonyl-14,17-diketomarcfortine A;
2-bicyclo[2.2.1]heptanoyl-14,17-diketomarcfortine A;
1-succinoyl-14,17-diketomarcfortine A;
1-(2,4-dinitrobenzenesulfenyl)-14,17-diketomarcfortine A;
1-(p-toluenesulfonyl)-14,17-diketomarcfortine A;
1-acetyl-14,17-diketomarcfortine A;
1-methyl-14,17-diketomarcfortine A;
1-benzyl-14,17-diketomarcfortine A;
1-dimethylcarbamoyl-14,17-diketomarcfortine A;
1-methoxycarbonyl-14,17-diketomarcfortine A;
14,17-diketomarcfortine B;
1-(p-toluenesulfonyl)-14,17-diketomarcfortine B;
1-ethyl-14,17-diketomarcfortine B;
1-benzyl-14,17-diketomarcfortine B;
18α-ethyl-14,17-diketomarcfortine B;
18a-benzyl-14,17-diketomarcfortine B;
18a-methoxyethoxymethyl-14,17-diketomarcfortine B;
18a-allyl-14,17-diketomarcfortine B;
18a-propargyl-14,17-diketomarcfortine B;
1,18a-bis-ethyl-14,17-diketomarcfortine B;
1,18a-bis-benzyl-14,17-diketomarcfortine B;
18a-ethyl-24-methoxy-14,17-diketomarcfortine B;
1-palmitoyl-14,17-diketomarcfortine A;
15,16-dehydro-14,17-diketomarcfortine A;
1-acetoxymethyl-15,16-dehydro-14,17-diketomarcfortine A;
1-diethoxyphosphoryl-15,16-dehydro-14,17-diketoxymarcfortine A;
1-dimethylsulfamoyl-15,16-dehydro-14,17-diketomarcfortine A;
1-cyclopropylcarbonyl-15,16-dehydro-14,17-diketomarcfortine A;
2-bicyclo[2.2.1]heptanoyl-15,16-dehydro-14,17-diketomarcfortine A;
1-succinoyl-15,16-dehydro-14,17-diketomarcfortine A;
1-(2,4-dinitrobenzenesulfenyl)-15,16-dehydro-14,17-diketomarcfortine A;
1-(p-toluenesulfonyl)-15,16-dehydro-14,17-diketomarcfortine A;
1-acetyl-15,16-dehydro-14,17-diketomarcfortine A;
1-methyl-15,16-dehydro-14,17-diketomarcfortine A;
1-benzyl-15,16-dehydro-14,17-diketomarcfortine A;
1-dimethylcarbamoyl-15,16-dehydro-14,17-diketomarcfortine A;
1-methoxycarbonyl-15,16-dehydro-14,17-diketomarcfortine A;
15,16-dehydro-14,17-diketomarcfortine B;
1-(p-toluenesulfonyl)-15,16-dehydro-14,17-diketomarcfortine B;
1-ethyl-15,16-dehydro-14,17-diketomarcfortine B;
1-benzyl-15,16-dehydro-14, 17-diketomarcfortine B;
18a-ethyl-15,16-dehydro-14,17-diketomarcfortine B;
18a-benzyl-15,16-dehydro-14,17-diketomarcfortine B;
18a-methoxyethoxymethyl-15,16-dehydro-14,17-diketomarcfortine B;
18a-allyl-15,16-dehydro-14,17-diketomarcfortine B;
18a-propargyl-15,16-dehydro-14,17-diketomarcfortine B;
1,18a-bis-ethyl-15,16-dehydro-14,17-diketomarcfortine B;
1,18a-bis-benzyl-15,16-dehydro-14,17-diketomarcfortine B;
18a-ethyl-24-methoxy-15,16-dehydro-14,17-diketomarcfortine B;
1-palmitoyl-15,16-dehydro-14,17-diketomarcfortine A;
14α-hydroxy-14α-methyl-17-ketomarcfortine A;
1-acetoxymethyl-14α-hydroxy-14β-methyl-17-ketomarcfortine A;
1-diethoxyphosphoryl-14α-hydroxy-14β-methyl-17-ketoxymarcfortine A;
1-dimethylsulfamoyl-14α-hydroxy-14β-methyl-17-ketomarcfortine A;
1-cyclopropylcarbonyl-14α-hydroxy-14β-methyl-17-ketomarcfortine A;
2-bicyclo[2.2.1]heptanoyl-14α-hydroxy-14β-methyl-17-ketomarcfortine A;
1-succinoyl-14α-hydroxy-14β-methyl-17-ketomarcfortine A;
1-(2,4-dinitrobenzenesulfenyl)-14α-hydroxy-141-methyl-17-ketomarcfortine A;
1-(p-toluenesulfonyl)-14α-hydroxy-14β-methyl-17-ketomarcfortine A;
1-acetyl-14α-hydroxy-14β-methyl-17-ketomarcfortine A;
1-methyl-14α-hydroxy-14β-methyl-17-ketomarcfortine A;
1-benzyl-14α-hydroxy-14β-methyl-17-ketomarcfortine A;
1-dimethylcarbamoyl-14α-hydroxy-14β-methyl-17-ketomarcfortine A;
1-methoxycarbonyl-14α-hydroxy-14β-methyl-17-ketomarcfortine A;
14α-hydroxy-14β-methyl-17-ketomarcfortine B;
1-(p-toluenesulfonyl)-14α-hydroxy-14β-methyl-17-ketomarofortine B;
1-ethyl-14α-hydroxy-14β-methyl-17-ketomarcfortine B;
1-benzyl-14α-hydroxy-14β-methyl-17-ketomarcfortine B;
18a-ethyl-14α-hydroxy-14β-methyl-17-ketomarcfortine B;
18a-benzyl-14α-hydroxy-14β-methyl-17-ketomarcfortine B;
18a-methoxyethoxymethyl-14α-hydroxy-14β-methyl-17-ketomarcfortine B;
18a-allyl-14x-hydroxy-14β-methyl-17-ketomarcfortine B;.
18a-propargyl-14α-hydroxy-14β-methyl-17-ketomarcfortine B;
1,18a-bis-ethyl-14α-hydroxy-14β-methyl-17-ketomarcfortine B;
1,18α-bis-benzyl-14α-hydroxy-14β-methyl-17-ketomarcfortine B;
18α-ethyl-24-methoxy-14α-hydroxy-14β-methyl-17-ketomarcfortine B;

1-palmitoyl-14α-hydroxy-14β-methyl-17-ketomarcfortine A;
14-ketomarcfortine A;
1-acetoxymethyl-14-ketomarcfortine A;
1-diethoxyphosphoryl-14-ketoxymarcfortine A;
1-dimethylsulfamoyl-14-ketomarcfortine A;
1-cyclopropylcarbonyl-14-ketomarcfortine A;
2-bicyclo [2.2.1]heptanoyl-14-ketomarcfortine A;
1-succinoyl-14-ketomarcfortine A;
1-(2,4-dinitrobenzenesulfenyl)-14-ketomarcfortine A;
1-(p-toluenesulfonyl)-14-ketomarcfortine A;
1-acetyl-14-ketomarcfortine A;
1-methyl-14-ketomarcfortine A;
1-benzyl-14-ketomarcfortine A;
1-dimethylcarbamoyl-14-ketomarcfortine A;
1-methoxycarbonyl-14-ketomarcfortine A;
14-ketomarcfortine B;
1-(p-toluenesulfonyl)-14-ketomarcfortine B;
1-ethyl-14-ketomarcfortine B;
1-benzyl-14-ketomarcfortine B;
18a-ethyl-14-ketomarcfortine B;
18a-benzyl-14-ketomarcfortine B;
18a-methoxyethoxymethyl-14-ketomarcfortine B;
18a-allyl-14-ketomarcfortine B;
18a-propargyl-14-ketomarcfortine B;
1,18a-bis-ethyl-14-ketomarcfortine B;
1,18a-bis-benzyl-14-ketomarcfortine B;
18a-ethyl-24-methoxy-14-ketomarcfortine B;
1-palmitoyl-14-ketomarcfortine A;
16-dithio-17-ketomarcfortine A;
1-acetoxymethyl-16-dithio-17-ketomarcfortine A;
1-diethoxyphosphoryl-16-dithio-17-ketoxymarcfortine A;
1-dimethylsulfamoyl-16-dithio-17-ketomarcfortine A;
1-cyclopropylcarbonyl-16-dithio-17-ketomarcfortine A;
2-bicyclo[2.2.1]heptanoyl-16-dithio-17-ketomarcfortine A;
1-succinoyl-16-dithio-17-ketomarcfortine A;
1-(2,4-dinitrobenzenesulfenyl)-16-dithio-17-ketomarofortine A;
1-(p-toluenesulfonyl)-16-dithio-17-ketomarcfortine A;
1-acetyl-16-dithio-17-ketomarcfortine A;
1-methyl-16-dithio-17-ketomarcfortine A;
1-benzyl-16-dithio-17-ketomarcfortine A;
1-dimethylcarbamoyl-16-dithio-17-ketomarcfortine A;
1-methoxycarbonyl-16-dithio-17-ketomarcfortine A;
16-dithio-17-ketomarcfortine B;
1-(p-toluenesulfonyl)-16-dithio-17-ketomarcfortine B;
1-ethyl-16-dithio-17-ketomarcfortine B;
1-benzyl-16-dithio-17-ketomarcfortine B;
18a-ethyl-16-dithio-17-ketomarcfortine B;
18a-benzyl-16-dithio-17-ketomarcfortine B;
18a-methoxyethoxymethyl-16-dithio-17-ketomarcfortine B;
18a-allyl-16-dithio-17-ketomarcfortine B;
18a-propargyl-16-dithio-17-ketomarcfortine B;
1,18a-bis-ethyl-16-dithio-17-ketomarcfortine B;
1,18a-bis-benzyl-16-dithio-17-ketomarcfortine B;
18a-ethyl-24-methoxy-16-dithio-17-ketomarcfortine B;
1-palmitoyl-16-dithio-17-ketomarcfortine A;
16-thiophenyl-15,16-dehydro-17-ketomarcfortine A;
1-acetoxymethyl-16-thiophenyl-15,16-dehydro-17-ketomarcfortine A;
1-diethoxyphosphoryl-16-thiophenyl-15,16-dehydro-17-ketoxymarcfortine A;
1-dimethylsulfamoyl-16-thiophenyl-15,16-dehydro-17-ketomarcfortine A;
1-cyclopropylcarbonyl-16-thiophenyl-15,16-dehydro-17-ketomarcfortine A;
2-bicyclo[2.2.1]heptanoyl-16-thiophenyl-15,16-dehydro-17-ketomarcfortine A;
1-succinoyl-16-thiophenyl-15,16-dehydro-17-ketomarcfortine A;
1-(2,4-dinitrobenzenesulfenyl)-16-thiophenyl-15,16-dehydro-17-ketomarcfortine A;
1-(p-toluenesulfonyl)-16-thiophenyl-15,16-dehydro-17-ketomarcfortine A;
1-acetyl-16-thiophenyl-15,16-dehydro-17-ketomarcfortine A;
1-methyl-16-thiophenyl-15,16-dehydro-17-ketomarcfortine A;
1-benzyl-16-thiophenyl-15,16-dehydro-17-ketomarcfortine A;
1-dimethylcarbamoyl-16-thiophenyl-15,16-dehydro-17-ketomarcfortine A;
1-methoxycarbonyl-16-thiophenyl-15,16-dehydro-17-ketomarcfortine A;
16-thiophenyl-15,16-dehydro-17-ketomarcfortine B;
1-(p-toluenesulfonyl)-16-thiophenyl-15,16-dehydro-17-ketomarcfortine B;
1-ethyl-16-thiophenyl-15,16-dehydro-17-ketomarcfortine B;
1-benzyl-16-thiophenyl-15,16-dehydro-17-ketomarcfortine B;
18a-ethyl-16-thiophenyl-15,16-dehydro-17-ketomarcfortine B;
18a-benzyl-16-thiophenyl-15,16-dehydro-17-ketomarcfortine B;
18a-methoxyethoxymethyl-16-thiophenyl-15,16-dehydro-17-ketomarcfortine B;
18a-allyl-16-thiophenyl-15,16-dehydro-17-ketomarcfortine B;
18a-propargyl-16-thiophenyl-15,16-dehydro-17-ketomarcfortine B;
1,18a-bis-ethyl-16-thiophenyl-15,16-dehydro-17-ketomarcfortine B;
1,18a-bis-benzyl-16-thiophenyl-15,16-dehydro-17-ketomarcfortine B;
18a-ethyl-24-methoxy-16-thiophenyl-15,16-dehydro-17-ketomarcfortine B;
1-palmitoyl-16-thiophenyl-15,16-dehydro-17-ketomarcfortine A;
16-thiophenyl-15,16-dehydro-17-ketomarcfortine A;
1-acetoxymethyl-16-thiophenyl-15,16-dehydro-17-ketomarcfortine A;
1-diethoxyphosphoryl-16-thiophenyl-15,16-dehydro-17-ketoxymarcfortine A;
1-dimethylsulfamoyl-16-thiophenyl-15,16-dehydro-17-ketomarcfortine A;

1-cyclopropylcarbonyl-16-thiophenyl-15,16-dehydro-17-ketomarcfortine A;

2-bicyclo[2.2.1]heptanoyl-16-thiophenyl-15,16-dehydro-17-ketomarcfortine A;

1-succinoyl-16-thiophenyl-15,16-dehydro-17-ketomarcfortine A;

1-(2,4-dinitrobenzenesulfenyl)-16-thiophenyl-15,16-dehydro-17-ketomarcfortine A;

1-(p-toluenesulfonyl)-16-thiophenyl-15,16-dehydro-17-ketomarcfortine A;

1-acetyl-16-thiophenyl-15,16-dehydro-17-ketomarcfortine A;

1-methyl-16-thiophenyl-15,16-dehydro-17-ketomarcfortine A;

1-benzyl-16-thiophenyl-15,16-dehydro-17-ketomarcfortine A;

1-dimethylcarbamoyl-16-thiophenyl-15,16-dehydro-17-ketomarcfortine A;

1-methoxycarbonyl-16-thiophenyl-15,16-dehydro-17-ketomarcfortine A;

16-thiophenyl-15,16-dehydro-17-ketomarcfortine B;

1-(p-toluenesulfonyl)-16-thiophenyl-15,16-dehydro-17-ketomarcfortine B;

1-ethyl-16-thiophenyl-15,16-dehydro-17-ketomarcfortine B;

1-benzyl-16-thiophenyl-15,16-dehydro-17-ketomarcfortine B;

18a-ethyl-16-thiophenyl-15,16-dehydro-17-ketomarcfortine B;

18a-benzyl-16-thiophenyl-15,16-dehydro-17-ketomarcfortine B;

18a-methoxyethoxymethyl-16-thiophenyl-15,16-dehydro-17-ketomarcfortine B;

18a-allyl-16-thiophenyl-15,16-dehydro-17-ketomarcfortine B;

18a-propargyl-16-thiophenyl-15,16-dehydro-17-ketomarcfortine B;

1,18a-bis-ethyl-16-thiophenyl-15,16-dehydro-17-ketomarcfortine B;

1,18a-bis-benzyl-16-thiophenyl-15,16-dehydro-17-ketomarcfortine B;

18a-ethyl-24-methoxy-16-thiophenyl-15,16-dehydro-17-ketomarcfortine B;

1-palmitoyl-16-thiophenyl-15,16-dehydro-17-ketomarcfortine A;

14α-hydroxy-14β-methyl-15α-methyl-17-ketomarcfortine A;

1-acetoxymethyl-14α-hydroxy-14β-methyl-15α-methyl-17-ketomarcfortine A;

1-diethoxyphosphoryl-14α-hydroxy-14β-methyl-15α-methyl-17-ketoxymarcfortine A;

1-dimethylsulfamoyl-14α-hydroxy-14β-methyl-15α-methyl-17-ketomarcfortine A;

1-cyclopropylcarbonyl-14α-hydroxy-14β-methyl-15α-methyl-17-ketomarcfortine A;

2-bicyclo[2.2.1]heptanoyl-14α-hydroxy-14β-methyl-15α-methyl-17-ketomarcfortine A;

1-succinoyl-14α-hydroxy-14β-methyl-15α-methyl-17-ketomarcfortine A;

1-(2,4-dinitrobenzenesulfenyl)-14α-hydroxy-14β-methyl-15α-methyl-17-ketomarcfortine A;

1-(p-toluenesulfonyl)-14α-hydroxy-14β-methyl-15α-methyl-17-ketomarcfortine A;

1-acetyl-14α-hydroxy-14l-methyl-15α-methyl-17-ketomarcfortine A;

1-methyl-14α-hydroxy-14β-methyl-15α-methyl-17-ketomarcfortine A;

1-benzyl-14α-hydroxy-14l-methyl-15α-methyl-17-ketomarcfortine A;

1-dimethylcarbamoyl-14α-hydroxy-14β-methyl-15α-methyl-17-ketomarcfortine A;

1-methoxycarbonyl-14α-hydroxy-14β-methyl-15α-methyl-17-ketomarcfortine A;

14α-hydroxy-14β-methyl-15α-methyl-17-ketomarcfortine B;

1-(p-toluenesulfonyl)-14α-hydroxy-14β-methyl-15α-methyl-17-ketomarcfortine B;

1-ethyl-14α-hydroxy-14β-methyl-15α-methyl-17-ketomarcfortine B;

1-benzyl-14α-hydroxy-14l-methyl-15α-methyl-17-ketomarcfortine B;

18a-ethyl-14α-hydroxy-14β-methyl-15α-methyl-17-ketomarcfortine B;

18a-benzyl-14α-hydroxy-14β-methyl-15α-methyl-17-ketomarcfortine B;

18a-methoxyethoxymethyl-14α-hydroxy-14β-methyl-15α-methyl-17-ketomarcfortine B;

18a-allyl-14α-hydroxy-14β-methyl-15α-methyl-17-ketomarcfortine B;

18a-propargyl-14α-hydroxy-14β-methyl-15α-methyl-17-ketomarcfortine B;

1,18a-bis-ethyl-14α-hydroxy-14β-methyl-15α-methyl-17-ketomarcfortine B;

1,18a-bis-benzyl-14α-hydroxy-14β-methyl- 15α-methyl-17-ketomarcfortine B;

18a-ethyl-24-methoxy-14α-hydroxy-14β-methyl-15α-methyl-17-ketomarcfortine B;

1-palmitoyl-14α-hydroxy-14β-methyl-15α-methyl-17-ketomarcfortine A;

14α-hydroxy-15α-methyl-17-ketomarcfortine A;

1-acetoxymethyl-14α-hydroxy-15α-methyl-17-ketomarcfortine A;

1-diethoxyphosphoryl-14α-hydroxy-15α-methyl-17-ketoxymarcfortine A;

1-dimethylsulfamoyl-14α-hydroxy-15α-methyl-17-ketomarcfortine A;

1-cyclopropylcarbonyl-14α-hydroxy-15α-methyl-17-ketomarcfortine A;

2-bicyclo[2.2.1]heptanoyl-14α-hydroxy-15α-methyl-17-ketomarcfortine A;

1-succinoyl-14α-hydroxy-15α-methyl-17-ketomarcfortine A;

1-(2,4-dinitrobenzenesulfenyl)-14α-hydroxy-15α-methyl-17-ketomarcfortine A;

1-(p-toluenesulfonyl)-14α-hydroxy-15α-methyl-17-ketomarcfortine A;

1-acetyl-14α-hydroxy-15α-methyl-17-ketomarcfortine A;

1-methyl-14α-hydroxy-15α-methyl-17-ketomarcfortine A;

1-benzyl-14α-hydroxy-15α-methyl-17-ketomarcfortine A;

1-dimethylcarbamoyl-14α-hydroxy-15α-methyl-17-ketomarcfortine A;

1-methoxycarbonyl-14α-hydroxy-15α-methyl-17-ketomarcfortine A;

14α-hydroxy-15α-methyl-17-ketomarcfortine B;

1-(p-toluenesulfonyl)-14α-hydroxy-15α-methyl-17-ketomarcfortine B;

1-ethyl-14α-hydroxy-15α-methyl-17-ketomarcfortine B;

1-benzyl-14α-hydroxy-15α-methyl-17-ketomarcfortine B;

18a-ethyl-14α-hydroxy-15α-methyl-17-ketomarcfortine B;

18a-benzyl-14α-hydroxy-15α-methyl-17-ketomarcfortine B;

18a-methoxyethoxymethyl-14α-hydroxy-15α-methyl-17-ketomarcfortine B;

18a-allyl-14α-hydroxy-15α-methyl-17-ketomarcfortine B;

18a-propargyl-14α-hydroxy-15α-methyl-17-ketomarcfortine B;

1,18a-bis-ethyl-14α-hydroxy-15α-methyl-17-ketomarcfortine B;

1,18a-bis-benzyl-14α-hydroxy-15α-methyl-17-ketomarcfortine B;

18a-ethyl-24-methoxy-14α-hydroxy-15α-methyl-17-ketomarcfortine B;

1-palmitoyl-14α-hydroxy-15α-methyl-17-ketomarcfortine A;

15α-methyl-14,17-diketomarcfortine A;

1-acetoxymethyl-15α-methyl-14,17-diketomarcfortine A;

1-diethoxyphosphoryl-15α-methyl-14,17-diketoxymarcfortine A;

1-dimethylsulfamoyl-15α-methyl-14,17-diketomarcfortine A;

1-cyclopropylcarbonyl-15α-methyl-14,17-diketomarcfortine A;

2-bicyclo[2.2.1]heptanoyl-15α-methyl-14,17-diketomarcfortine A;

1-succinoyl-15α-methyl-14,17-diketomarcfortine A;

1-(2,4-dinitrobenzenesulfenyl)-15α-methyl-14,17-diketomarcfortine A;

1-(p-toluenesulfonyl)-15α-methyl-14,17-diketomarcfortine A;

1-acetyl-15α-methyl-14,17-diketomarcfortine A;

1-methyl-15α-methyl-14,17-diketomarcfortine A;

1-benzyl-15α-methyl-14,17-diketomarcfortine A;

1-dimethylcarbamoyl-15α-methyl-14,17-diketomarcfortine A;

1-methoxycarbonyl-15-methyl-14,17-diketomarcfortine A;

15α-methyl-14,17-diketomarcfortine B;

1-(p-toluenesulfonyl)-15α-methyl-14,17-diketomarcfortine B;

1-ethyl-15α-methyl-14,17-diketomarcfortine B;

1-benzyl-15α-methyl-14,17-diketomarcfortine B;

18a-ethyl-15α-methyl-14,17-diketomarcfortine B;

18a-benzyl-15α-methyl-14,17-diketomarcfortine B;

18a-methoxyethoxymethyl-15αα-methyl-14,17-diketomarcfortine B;

18a-allyl-15α-methyl-14,17-diketomarcfortine B;

18a-propargyl-15α-methyl-14,17-diketomarcfortine B;

1,18a-bis-ethyl-15α-methyl-14,17-diketomarcfortine B;

1,18a-bis-benzyl-15α-methyl-14,17-diketomarcfortine B;

18a-ethyl-24-methoxy-15α-methyl-14,17-diketomarcfortine B;

1-palmitoyl-15α-methyl-14,17-diketomarcfortine A;

1-palmitoyl-15α-methyl-14,17-diketomarcfortine D;

14,15-dehydro-16,17-diketomarcfortine A;

1-acetoxymethyl-14,15-dehydro-16,17-diketomarcfortine A;

1-diethoxyphosphoryl-14,15-dehydro-16,17-diketoxymarcfortine A;

1-dimethylsulfamoyl-14,15-dehydro-16,17-diketomarcfortine A;

1-cyclopropylcarbonyl-14,15-dehydro-16,17-diketomarcfortine A;

2-bicyclo[2.2.1]heptanoyl-14,15-dehydro-16,17-diketomarcfortine A;

1-succinoyl-14,15-dehydro-16,17-diketomarcfortine A;

1-(2,4-dinitrobenzenesulfenyl)-14,15-dehydro-16,17-diketomarcfortine A;

24-propoxy-24,25-dihydro-14,15-dehydro-16,17-diketomarcfortine A;

1-(p-toluenesulfonyl)-14,15-dehydro-16,17-diketomarcfortine A;

1-acetyl-14,15-dehydro-16,17-diketomarcfortine A;

1-methyl-14,15-dehydro-16,17-diketomarcfortine A;

1-benzyl-14,15-dehydro-16,17-diketomarcfortine A;

1-dimethylcarbamoyl-14,15-dehydro-16,17-diketomarcfortine A;

1-methoxycarbonyl-14,15-dehydro-16,17-diketomarcfortine A;

14,15-dehydro-16,17-diketomarcfortine B;

1-(p-toluenesulfonyl)-14,15-dehydro-16,17-diketomarcfortine B;

1-ethyl-14,15-dehydro-16,17-diketomarcfortine B;

1-benzyl-14,15-dehydro-16,17-diketomarcfortine B;

18a-ethyl-14,15-dehydro-16,17-diketomarcfortine B;

18a-benzyl-14,15-dehydro-16,17-diketomarcfortine B;

18a-methoxyethoxymethyl-14,15-dehydro-16,17-diketomarcfortine B;

18a-allyl-14,15-dehydro-16,17-diketomarcfortine B;

18a-propargyl-14,15-dehydro-16,17-diketomarcfortine B;

1,18a-bis-ethyl-14,15-dehydro-16,17-diketomarcfortine B;

1,18a-bis-benzyl-14,15-dehydro-16,17-diketomarcfortine B;

18a-ethyl-24-methoxy-14,15-dehydro-16,17-diketomarcfortine B;

1-palmitoyl-14,15-dehydro-16,17-diketomarcfortine A.

* * * * *

UNITED STATES PATENT AND TRADEMARK OFFICE
CERTIFICATE OF CORRECTION

| | |
|---|---|
| PATENT NO. | : 5,750,533 |
| APPLICATION NO. | : 08/557033 |
| DATED | : May 12, 1998 |
| INVENTOR(S) | : Byung H. Lee |

It is certified that error appears in the above-identified patent and that said Letters Patent is hereby corrected as shown below:

On Title Page item 57

Abstract

The compound shown has a "nitrogen" (N) in the position between the carbon numbered at the 7 position and the carbon numbered at the 24 position (right hand side of the compound shown).

The compound shown should have $-Y-$ in the position between the carbon numbered at the 7 position and the carbon numbered at the 24 position, wherein Y is an oxygen atom (---O---) or a bond.

Column 3
Lines 16 – 31 (the Description of Invention section)

The compound shown has a "nitrogen" (N) in the position between the carbon numbered at the 7 position and the carbon numbered at the 24 position (right hand side of the compound shown).

The compound shown should have $-Y-$ in the position between the carbon numbered at the 7 position and the carbon numbered at the 24 position, wherein Y is an oxygen atom (--O--) or a bond.

The corrected compound for the Abstract and Column3, Lines 16-31 appears on page 2.

The correcetd compound for the Abstract and Column3, Lines 16-31 appears below.

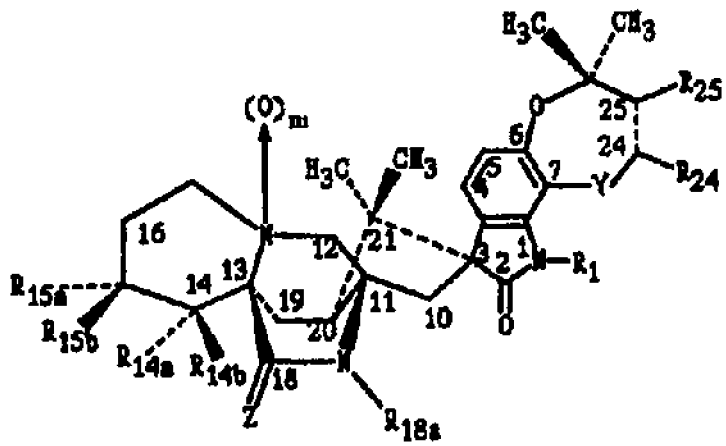

UNITED STATES PATENT AND TRADEMARK OFFICE
CERTIFICATE OF CORRECTION

| | |
|---|---|
| PATENT NO. | : 5,750,533 |
| APPLICATION NO. | : 08/557033 |
| DATED | : May 12, 1998 |
| INVENTOR(S) | : Byung H. Lee |

It is certified that error appears in the above-identified patent and that said Letters Patent is hereby corrected as shown below:

Column 97
Lines 20 – 35 (the Claims section)

The compound shown has a "nitogren" (N) in the position between the carbon numbered at the 7 position and the carbon numbered at the 24 position (right hand side of the compound shown).

The compound shown should have --oxygen-- (O) in the position between the carbon numbered at the 7 position and the carbon numbered at the 24 position.

The corrected compound for Column 97, Lines 20-35 appears below.

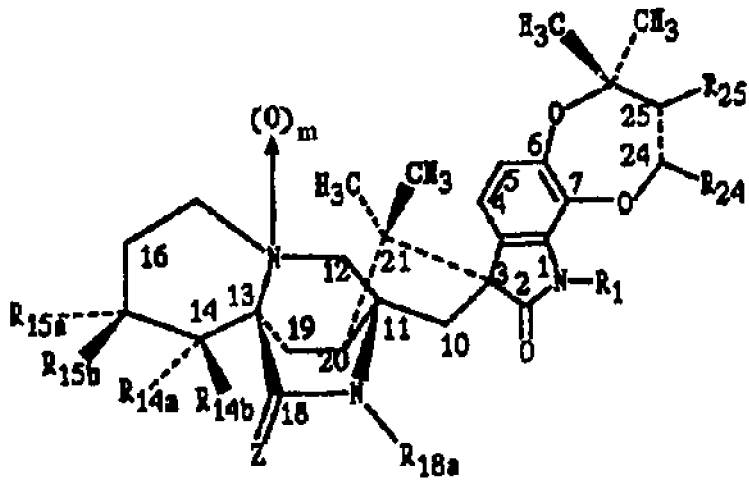

Signed and Sealed this

Twentieth Day of March, 2007

JON W. DUDAS
*Director of the United States Patent and Trademark Office*